United States Patent [19]
Martin

[11] 3,962,307
[45] June 8, 1976

[54] CYANOBENZENEACETONITRILES
[75] Inventor: Elmore Louis Martin, Wilmington, Del.
[73] Assignee: E. I. Du Pont de Nemours and Company, Wilmington, Del.
[22] Filed: Feb. 18, 1975
[21] Appl. No.: 550,853

Related U.S. Application Data
[60] Division of Ser. No. 241,849, April 6, 1972, Pat. No. 3,877,927, which is a continuation-in-part of Ser. No. 201,995, Nov. 24, 1971, abandoned.

[52] U.S. Cl. ............................ 260/465 H; 71/105; 71/125; 71/126; 260/465 G; 260/645; 260/646; 260/651 R
[51] Int. Cl.² ...................................... C07C 121/66
[58] Field of Search .................... 260/465 G, 465 H

[56] References Cited
UNITED STATES PATENTS
3,574,594  4/1971  Gough et al. .................. 260/465 X Primary Examiner—Lewis Gotts
Assistant Examiner—Dolph H. Torrence

[57] ABSTRACT

Certain substituted cyanobenzeneacetonitriles, and their halobenzyl halide intemediates are effective pre-emergence and postemergence herbicides, which control undesired vegetation without injury to crops.

4 Claims, No Drawings

CYANOBENZENEACETONITRILES

CROSS-REFERENCE TO RELATED APPLICATION

This is a division of application Ser. No. 241,849, filed Apr. 6, 1972 now U.S. Pat. No. 3,877,927, which in-turn is a continuation-in-part of my copending application Ser. No. 201,995, filed Nov. 24, 1971 and now abandoned.

BACKGROUND OF THE INVENTION

This invention relates to a class of substituted cyanobenzeneacetonitriles and their halobenzyl halide intermediates, to the use of both classes of compounds as herbicides, and to herbicidal compositions containing them as active ingredients.

U.S. Pat. No. 3,574,594 (to Gough et. al.) discloses that unsubstituted cyanobenzeneacetonitriles and trifluoromethylbenzeneacetonitriles are useful preemergence herbicides. Those compounds appear, however, to be only moderately active and quite nonselective.

Although a large number of herbicides are presently on the market, there is a continual need for more active, more selective, and reasonably priced herbicides that could be used in the presence of commercial crops.

SUMMARY OF THE INVENTION

It has now been discovered that certain cyanobenzeneacetonitriles and intermediate halobenzyl halides

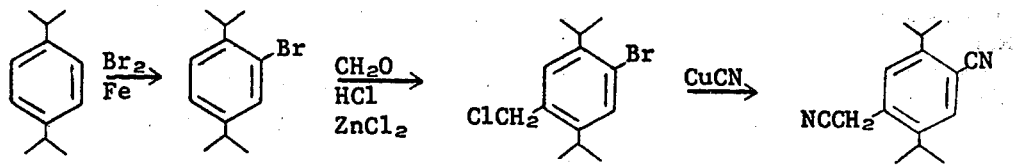

exhibit selective herbicidal activity and can be used in the presence of valuable crops, e.g., soybeans, wheat, corn, and rice. These compounds are represented by Formula (1).

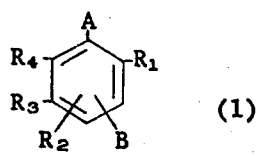

wherein

A and B are different, one being a Z group and the other being a $CR_5R_6Z$ radical; wherein $R_5$ and $R_6$ are each independently hydrogen or methyl, and Z is the cyano group or halogen; and each of $R_1$, $R_2$, $R_3$, and $R_4$ independently is hydrogen, a $C_1$-$C_7$ alkyl, a halogen, or the nitro group;

provided that:
a. at most two of $R_1$, $R_2$, $R_3$, and $R_4$ are nitro groups;
b. at most two of $R_1$, $R_2$, $R_3$, and $R_4$ are halogens;
c. at least one of $R_1$, $R_2$, $R_3$, and $R_4$ hydrogen or halogen;
d. at least one of $R_1$, $R_2$, $R_3$, and $R_4$ is a $C_2$-$C_7$ alkyl;
e. no nitro groups are ortho to each other;
f. no alkyl groups are ortho to each other;
g. each alkyl group has at most three carbon atoms in a straight chain from the point of attachment to the aromatic ring; and
h. when Z is halogen, both $R_5$ and $R_6$ must be hydrogens.

The halobenzyl halide compounds are intermediates in the synthesis of the above cyanobenzeneacetonitriles. Although not as active as the cyanobenzeneacetonitriles, these intermediates also are useful as selective herbicides for control of annual grass weeds in crops.

DETAILED DESCRIPTION OF THE INVENTION

Compounds of Formula (1) can be prepared by many processes based on methods generally well known in the art. Simple cyanobenzeneacetonitriles can be made, for instance, by bromination of the corresponding dialkylbenzenes, chloromethylation of the resulting bromodialkylbenzenes, and replacement of the halogens with cyano groups. This reaction is illustrated by the following equations.

Cyanobenzeneacetonitriles can be nitrated to a mononitro or dinitro compound, e.g.

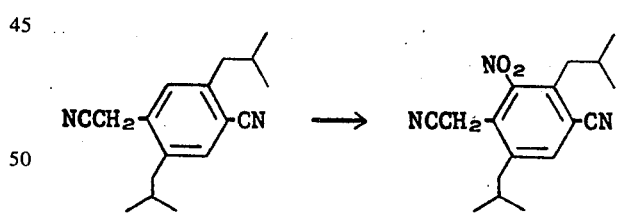

Nitration is carried out by well-known methods, concentrated nitric acid and nitronium tetrafluoroborate being suitable nitrating agents.

Halogenated cyanobenzeneacetonitriles can be obtained from the corresponding 2,4-dihalo-3,6-dialkylbenzyl halides, as shown below:

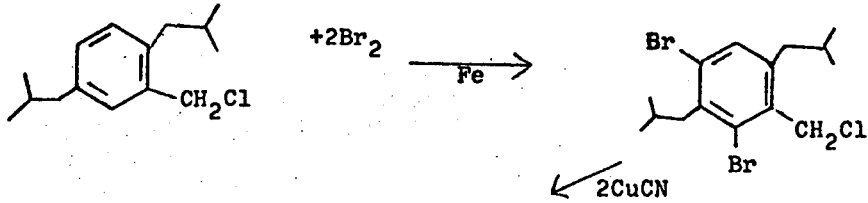

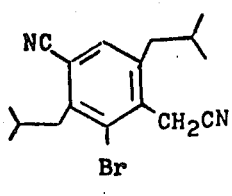

Preferred because of ease of synthesis and high activity are the compounds of formula (2), below:

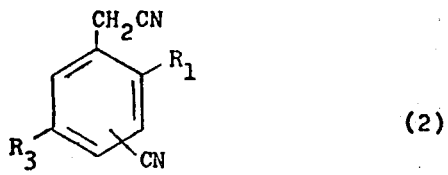

wherein
  $R_1$ and $R_3$ are each independently alkyl of 2–5 carbon atoms, chlorine, bromine, or the nitro group.

It will be noted that the compounds of Formula (2) are those compounds of Formula (1) wherein A is the cyanomethyl group; B is the cyano group; and each of $R_2$ and $R_4$ is hydrogen.

The most active are those compounds of Formula (2) wherein
  $R_1$ is alkyl of 3–5 carbon atoms or the nitro group, and $R_3$ is alkyl of 3–5 carbon atoms.

The same order of preference applies to the corresponding halobenzylhalide intermediates for the same reasons.

The compounds of this invention are useful as selective pre-plant incorporated, preemergence, or postemergence herbicides. They provide control of many weeds with excellent selectivity in such crops as corn, soybeans, wheat, cotton and rice. The compounds are most advantageously applied preemergence at rates of 0.25 to 10 pounds per acre, depending on the crop, the weed to be controlled, the soil and environmental conditions and the particular chemical used. Under certain conditions, such as lack of rainfall for an extended period after application, it is advantageous to lightly incorporate these compounds into the soil. Selected members of this class of compounds have postemergence activity and may be used at rates of 1 to 10 kg./ha. for postemergence weed control, if applied while susceptible weeds are young, preferably in the two-leaf stage of development. Two or more compounds of this invention may be applied simultaneously.

Weeds controlled include crabgrass (Digitaria spp), barnyardgrass (*Echinochloa crusgalli*), junglerice (*Echinochloa colonum*), foxtail (Setaria spp.), witchgrass (*Panicum capillare*), goosegrass (*Eleusine indica*), pigweed (*Amaranthus retroflexus*), wild mustard (Brassica spp), curly dock (*Rumex crispus*), johnsongrass (*Sorghum halepense*) from seed, cheat (*Bromus secalinus*), downy bromo (*Bromus tectorum*) and blackgrass (*Alopucurus mysuroides*).

It is sometimes advantageous to combine a compound of this invention with another herbicide in order to increase the spectrum of weeds controlled and to minimize the chances of injury to the current or subsequent crops. The exact combination which may be used to the best advantage will depend upon the crop, the weeds to be controlled and the environment in which the crop is growing, but can be readily selected by one with ordinary skill in the art. The use of these herbicides in combination with the herbicides of this invention will provide control of a wide variety of broadleaved weeds including ragweed (Ambrosia spp.), lambsquarter (*Chenopodium album*), morningglory (Ipomea spp.), ), sicklepod (*Cassia obtusifolia*), smartweed (*Polyganum spp.*), flower-of-an-hour (*Hibiscus trionum*), cocklebur (Xanthium spp.), and velvetleaf (*Abutilon theophrasti*), as well as grasses.

The herbicidal compositions of this invention containing mixtures with other herbicides can be formulated as such. Alternatively, the compounds of Formula (1) may be tank-mixed with other known herbicides or applied sequentially with other known herbicides.

Among the known herbicides which can be combined with the compounds of Formula (1) are:

SUBSTITUTED UREAS 3-(3,4-dichlorophenyl)-1,1-dimethylurea
3-(4-chlorophenyl)-1,1-dimethylurea
3-phenyl-1,1-dimethylurea
3-(3,4-dichlorophenyl)-3-methoxy-1,1-dimethylurea
3-(4-chlorophenyl)-3-methoxy-1,1-dimethylurea
3-(3,4-dichlorophenyl)-1,-n-butyl-1-methylurea
3-(3,4-dichlorophenyl)-1-methoxy-1-methylurea
3-(4-chlorophenyl)-1-methoxy-1-methylurea
3-(3,4-dichlorophenyl)-1,1,3-trimethylurea
3-(3,4-dichlorophenyl)-1,1-diethylurea
3-(p-chlorophenoxyphenyl)-1,1-dimethylurea
N-cyclooctyl-N'-dimethylurea
3-(4-chlorophenyl)-1-methyl-1-(1-methyl-2-propynyl)urea
3-(4-bromo-3-chlorophenyl)-1-methoxy-1-methylurea
3-[p-(p-chlorophenoxy)phenyl]-1,1-dimethylurea
3-(4-trifluoromethylphenyl)-1,1-dimethylurea
3-(4-bromophenyl)-1-methoxy-1-methylurea
3-(hexahydro-4,7-methanoindan-5-yl)-1,1-dimethylurea
1-(2-methylcyclohexyl)-3-phenylurea
3-(p-cumenyl)-1,1-dimethylurea These ureas can be mixed with the compounds of Formula (1) in weight proportions of from 1:40 to 10:1, the preferred ratio being 1:12 to 4:1.

SUBSTITUTED TRIAZINES 2-chloro-4,6-bis(ethylamino)-s-triazine
2-chloro-4-ethylamino-6-isopropylamino-s-triazine
2-chloro-4,6-bis(methoxypropylamino)-s-triazine
2-methoxy-4,6-bis(isopropylamino)-s-triazine
2-diethylamino-4-isopropylacetamido-6-methoxy-s-triazine
2-isopropylamino-4-methoxyethylamino-6-methylmercapto-s-triazine
2-methylmercapto-4,6-bis(isopropylamino)-s-triazine
2-methylmercapto-4,6-bis(ethylamino)-s-triazine
2-methylmercapto-4-ethylamino-6-isopropylamino-s-triazine
2-methoxy-4,6-bis(ethylamino)-s-triazine 2-methoxy-4-ethylamino-6-isopropylamino-s-triazine
2-chloro-4,6-bis(isopropylamino)-s-triazine
2-methoxy-4,6-bis(isopropylamino)-s-triazine
2-ethylamino-4-isopropylamino-6-methylmercapto-s-triazine
2-chloro-4-chloropropylamino-6-isopropylamino-1,3,5-triazine
2,4-bis(isopropylamino)-6-methylmercapto-s-triazine
2-tert-butylamino-4-ethylamino-6-methylthio-s-triazine These triazines can be mixed with the compounds of this invention in the weight proportions of from 1:40 to 10:1, the preferred ratio being 1:12 to 4:1.

PHENOLS 3,5-dinitro-o-cresol
4,6-dinitro-o-sec-butylphenol and its salts
4,6-dinitro-o-sec-amylphenol
pentachlorophenol and its salts These phenols can be mixed with the compounds of this invention in the weight proportions of from 1:10 to 10:1, the preferred ratio being 1:5 to 5:1.

SUBSTITUTED URACILS 3-isopropyl-5-bromo-6-methyluracil
5-bromo-3-sec-butyl-6-methyluracil
3-tert-butyl-5-chloro-6-methyluracil
5-chloro-6-methyl-3-neopentyluracil
3-tert-butyl-5-bromo-6-methyluracil
3-isopropyl-5-chloro-6-methyluracil
3-tert-butyl-5-chloro-6-ethyluracil
3-tert-butyl-5-chloro-6-chloromethyluracil
3-cyclohexyl-6-methyluracil
3-cyclohexyl-6-ethyluracil
3-cyclohexyl-6-sec-butyluracil
3-norbornyl-6-methyluracil
3-cyclopentyl-6-methyluracil
3-cyclohexyl-6-isopropyluracil
3-cyclohexyl-5,6-trimethyleneuracil
3-sec-butyl-5,6-trimethyleneuracil
3-isopropyl-5,6-trimethyleneuracil
3-isopropyl-5,6-tetramethyleneuracil
3-isopropyl-5,6-pentamethyleneuracil
3-cyclohexyl-5-bromouracil
3-cyclohexyl-5-chlorouracil
3-isopropyl-5-bromouracil
3-sec-butyl-5-bromouracil
3-sec-butyl-5-chlorouracil
3-isopropyl-1-trichloromethylthio-5-bromo-6-methyluracil
3-cyclohexyl-1-trichloromethylthio-5-bromo-6-methyluracil
3-sec-butyl-1-acetyl-5-bromo-6-methyluracil
3-isopropyl-1-acetyl-5-bromo-6-methyluracil
3-isopropyl-1-trichloromethylthio-5-chloro-6-methyluracil These substituted uracils can be mixed with the compounds of this invention in the weight proportions of from 1:80 to 10:1, the preferred ratio being from 1:20 to 4:1

CARBOXYLIC ACIDS AND DERIVATIVES

The following carboxylic acids and derivatives can be mixed with the compounds of this invention in the listed weight proportions:

A.
2,3,6-trichlorobenzoic acid and its salts
2,3,5,6-tetrachlorobenzoic acid and its salts
2-methoxy-3,5,6-trichlorobenzoic acid and its salts
2-methoxy-3,6-dichlorobenzoic acid and its salts
2-methoxy-3,5,6-trichlorobenzoic acid
3-amino-2,5-dichlorobenzoic acid and its salts
3-nitro-2,5-dichlorobenzoic acid and its salts
2-methyl-3,6-dichlorobenzoic acid and its salts
4-chlorophenoxyacetic acid and its salts and esters
2,4-dichlorophenoxyacetic acid and its salts and esters
2,4-dichlorophenoxyethylsulfate
2,4,5-trichlorophenoxyacetic acid and its salts and esters
(2-methyl-4-chlorophenoxy)acetic acid and its salts and esters
(2-methyl-4-chlorophenoxy)propionic acid and its salts and esters
2-(2,4,5-trichlorophenoxy)propionic acid and its salts and esters
2-(2,4,5-trichlorophenoxy)ethyl-2,2-dichloropropionate
4-(2,4-dichlorophenoxy)butyric acid and its salts and esters
4-(2-methyl-4-chlorophenoxy)butyric acid and its salts and esters
2,3,6-trichlorobenzyloxypropanol
tris(2,4-dichlorophenoxyethyl)phosphite
Mixed in a 1:80 to 8:1 ratio, preferably a 1:20 to 2:1 ratio.

B.
2,6-dichlorobenzonitrile
3,5-dibromo-4-hydroxybenzonitrile
Mixed in a 1:40 to 4:1 ratio, preferably a 1:16 to 3:1 ratio.

C.
trichloroacetic acid and its salts
Mixed in a 1:8 to 8:1 ratio, preferably a 1:4 to 4:1 ratio.

D.
2,2-dichloropropionic acid and its salts
2-(α-naphthoxy)-N,N-diethylpropionamide
2-(4-chloro-6-ethylamino-2-ylamino)methylpropionitrile
Mixed in a 1:8 to 8:1 ratio, preferably a 1:4 to 4:1 ratio.

E
N,N-di(n-propyl)thiolcarbamic acid, ethyl ester
N,N-di(n-propyl)thiolcarbamic acid, n-propyl ester
N-ethyl-N-(n-butyl)thiolcarbamic acid, ethyl ester
N-ethyl-N-(n-butyl)thiolcarbamic acid, n-propyl ester
S-2,3-dichloroallyl-N,N-diisopropylthiolcarbamate
S-2,3,3-trichlorally-N,N-di-isopropylthiolcarbamate
S-propyl-n-butylethylthiocarbamic acid
2-chloroallyldithiocarbamate
S-ethyl diisobutylthiocarbamate
2-chloroallyldiethyldithiocarbamate
S-ethyl-N-ethylthiocyclohexanecarbamate
Mixed in a 1:4 to 4:1 ratio, preferably a 1:2 to 2:1 ratio.

F.
N-phenylcarbamic acid, isopropyl ester
N-(m-chlorophenyl)carbamic acid, isopropyl ester
N-(m-chlorophenyl)carbamic acid, 4-chloro-2-butynyl ester
N-(3,4-dichlorophenyl) carbamic acid, methyl ester
N-(3,3-dimethylureido)phenyl-tert-butylcarbamate
2,6-di-tert-butyl-p-tolylmethylcarbamate Mixed in a 1:8 to 8:1 ratio, preferably a 1:4 to 4:1 ratio.

G. 2,3,6-trichlorophenylacetic acid and its salts

Mixed in a 1:4 to 8:1 ratio, preferably a 1:4 to 4:1 ratio.

H.
2-chloro-N,N-diallylacetamide maleic hydrazide
1,2-dihydropyridazine-3,6-dione
3',4'-dichloro-2-methacrylanilide
2-chloro-2', 6'-diethyl-N-(methoxymethyl)acetanilide
N-(butoxymethyl)-2-chloro-2',6'-diethylacetanilide
3,5-dinitro-N',N'-dipropylsulfanilamide
2-chloro-N-isopropylacetanilide
3',4'-dichloropropionanilide Mixed in a 1:8 to 10:1 ratio, preferably a 1:4 to 5:1 ratio.

I.
4-amino-3,5,6-trichloropicolinic acid

Mixed in a 1:100 to 4:1 ratio, preferably a 1:20 to 2:1 ratio.

INORGANIC AND MIXED INORGANIC-ORGANIC SALTS

The following salts can be mixed with the compounds of this invention in the listed weight proportions:

A.
monoammonium methanearsonate
calcium methylarsonate
calcium propylarsonate
disodium monomethylarsonate
octyl-dodecylammoniummethylarsonate
dimethylarsinic acid
hydroxydimethylarsine oxide Mixed in a 1:8 to 4:1 ratio, preferably a 1:4 to 2:1 ratio.

B.
sodium arsenite
potassium cyanate

Mixed in a 1:10 to 20:1 ratio, preferably a 1:5 to 10:1 ratio.

C.
lead arsenate
calcium arsenate

Mixed in a 10:1 to 100:1 ratio, preferably a 20:1 to 50:1 ratio.

D.
sodium tetraborate hydrated, granulated
sodium metaborate
sodium pentaborate
polyborchlorate
unrefined borate ore such as borascu Mixed in a 10:1 to 600:1 ratio, preferably a 20:1 to 400:1 ratio.

E.
ammonium thiocyanate

Mixed in a 1:10 to 10:1 ratio, preferably a 1:5 to 5:1 ratio.

F.
sodium chlorate

Mixed in a 10:1 to 200:1 ratio, preferably a 15:1 to 100:1 ratio.

G.
ammonium sulfamate

Mixed in a 1:1 to 200:1 ratio, preferably a 2:1 to 100:1 ratio.

OTHER ORGANIC HERBICIDES

These organic herbicides can be mixed with compounds of this invention in the listed weight proportions:

A.
6,7-dihydrodipyrido[1,2-a;2',1'-c]pyrazinediium ion
1,1'-dimethyl-4,4'-bipyridinium ion Mixed in a 1:20 to 10:1 ratio, preferably a 1:10 to 5:1 ratio.

B.
3-amino-1,2,4-triazole

Mixed in a 1:20 to 20:1 ratio, preferably a 1:10 to 10:1 ratio.

C.
3,6-endoxohexahydrophthalic acid

Mixed in a 1:10 to 20:1 ratio, preferably a 1:4 to 10:1 ratio.

D.
hexachloroacetone

Mixed in a 1:8 to 16:1 ratio, preferably a 1:4 to 8:1 ratio.

E.
diphenylacetonitrile
N,N-dimethyl-$\alpha,\alpha$-diphenylacetamide
N,N-di-n-propyl-2,6-dinitro-4-trifluoromethylaniline
N,N-di-n-propyl-2,6-dinitro-4-methylaniline
2,6-dinitro-N,N-di(2-chloroethyl)-p-toluidine
4-(methylsulfonyl)-2,6-dinitro-N,N-dipropylaniline
N-sec-butyl-4-tert-butyl-2,6-dinitroaniline
4-isopropyl-2,6-dinitro-N,N-dipropylaniline Mixed in a 1:10 to 10:1 ratio, preferably a 1:5 to 5:1 ratio.

F.
0-(2,4-dichlorophenyl)-O-methylisopropylphosphoramidothiate
0,0-diisopropylphosphorodithioate-S-ester with N-(2-mercaptoethyl)benzenesulfonamide
S-ethylhexahydro-1-H-azepine-1-carbothioate
2,3,5,6,-tetrachloroterephthalic acid, dimethyl ester Mixed in a 1:20 to 20:1 ratio, preferably a 1:10 to 10:1 ratio.

G.
2,4-dichlorophenyl-4'-nitrodiphenyl ether
2,4-dinitro-4-trifluoromethyldiphenylether Mixed in a 1:20 to 10:1 ratio, preferably a 1:10 to 5:1 ratio.

H.
N-1-naphthylphthalamic acid and its salts

Mixed in a 1:8 to 20:1 ratio, preferably a 1:4 to 10:1 ratio.

I.
3'-chloro-2-methyl-p-valerotoluidide
2-chloro-N-(ethoxymethyl)-6'-ethyl-O-acetotoluidide
N-butyl-N-ethyl-$\alpha,\alpha$, $\alpha$-trifluoro-2,6-dinitro-p-toluidine Mixed in a 1:10 to 10:1 ratio, preferably a 1:5 to 5:1 ratio.

J.
3,3a-dihydro-2-(p-methoxyphenyl)-8H-pyrazolo(5-,1A)-isoindol-8-one
2-[3-(4-methoxyphenyl)-5-pyrazolyl)benzoic acid
2-(3-phenyl-5-pyrazolyl)benzoic acid Mixed in a 1:20 to 8:1 ratio, preferably a 1:10 to 4:1 ratio.

The preparation of representative halobenzyl halides and cyanobenzeneacetonitriles is illustrated in the following examples, wherein all parts, proportions, and percentages are per weight unless indicated otherwise.

EXAMPLE 1

3-Bromo-4-isopropylbenzyl Chloride
3-Bromo-2-isopropylbenzyl Chloride, and
4-Bromo-3-isopropylbenzyl Chloride Into a mechanically stirred mixture of 99 parts of 2-bromoisopropylbenzene, 20 parts of paraformaldehyde, and 10 parts of zinc chloride is passed a rapid stream of dry hydrogen chloride at 50°–60°C. The mixture is stirred for 3 hours at 50°–60°C, then cooled and diluted with methylene chloride. The methylene chloride mixture is filtered. The filtrate is washed with dilute hydrochloric acid and dilute sodium bicarbonate until neutral, dried and concentrated. The residue is chromatographed on Floirsil or alumina and 3-bromo-4-isopropylbenzyl chloride, 3-bromo-2-isopropylbenzyl chloride, and 4-bromo-3-isopropylbenzyl chloride are isolated as three of the fractions.

The following benzyl chlorides are prepared from the listed alkylhalobenzenes by the method described in the above example. Where isomeric mixtures are formed, the isomers are separated by chromatography or fractional distillation.

TABLE I

| Starting Material | Product |
| --- | --- |
| 2-bromoethylbenzene | 3-bromo-4-ethylbenzyl chloride |
|  | 3-bromo-2-ethylbenzyl chloride |
|  | 4-bromo-3-ethylbenzyl chloride |
| 2-bromoisopropylbenzene | 3-bromo-4-isopropylbenzyl chloride |
|  | 3-bromo-2-isopropylbenzyl chloride |
|  | 4-bromo-3-isopropylbenzyl chloride |
| 2-bromo-sec-butylbenzene | 3-bromo-4-sec-butylbenzyl chloride |
|  | 3-bromo-2-sec-butylbenzyl chloride |
|  | 4-bromo-3-sec-butylbenzyl chloride |
| 2-bromo-tert-butylbenzene | 3-bromo-4-tert-butylbenzyl chloride |
|  | 3-bromo-2-tert-butylbenzyl chloride |
|  | 4-bromo-3-tert-butylbenzyl chloride |
| 2-bromoisobutylbenzene | 3-bromo-4-isobutylbenzyl chloride |
|  | 3-bromo-2-isobutylbenzyl chloride |
|  | 4-bromo-3-isobutylbenzyl chloride |
| 3-bromoethylbenzene | 2-bromo-4-ethylbenzyl chloride |
|  | 4-bromo-2-ethylbenzyl chloride |
|  | 3-bromo-5-ethylbenzyl chloride |
| 3-bromo-(1,1,2,2-tetramethylpropyl)benzene | 2-bromo-4-(1,1,2,2-tetramethylpropyl)benzyl chloride |
|  | 4-bromo-2-(1,1,2,2-tetramethylpropyl)benzyl chloride |
|  | 3-bromo-5-(1,1,2,2-tetramethylpropyl)benzyl chloride |
| 3-bromoisopropylbenzene | 2-bromo-4-isopropylbenzyl chloride |
|  | 4-bromo-2-isopropylbenzyl chloride |
|  | 3-bromo-5-isopropylbenzyl chloride |
| 3-bromo-sec-butylbenzene | 2-bromo-4-sec-butylbenzyl chloride |
|  | 4-bromo-2-sec-butylbenzyl chloride |
|  | 3-bromo-5-sec-butylbenzyl chloride |
| 3-bromo-tert-butylbenzene | 2-bromo-4-tert-butylbenzyl chloride |
|  | 4-bromo-2-tert-butylbenzyl chloride |
|  | 3-bromo-5-tert-butylbenzyl chloride |
| 3-bromoisobutylbenzene | 2-bromo-4-isobutylbenzyl chloride |
|  | 4-bromo-2-isobutylbenzyl chloride |
|  | 3-bromo-5-isobutylbenzyl chloride |
| 4-bromoethylbenzene | 5-bromo-2-ethylbenzyl chloride |
|  | 2-bromo-5-ethylbenzyl chloride |
| 4-bromoisopropylbenzene | 5-bromo-2-isopropylbenzyl chloride |
|  | 2-bromo-5-isopropylbenzyl chloride |
| 4-bromo-sec-butylbenzene | 5-bromo-2-sec-butylbenzyl chloride |
|  | 2-bromo-5-sec-butylbenzyl chloride |
| 4-bromo-tert-butylbenzene | 5-bromo-2-tert-butylbenzyl chloride |
|  | 2-bromo-5-tert-butylbenzyl chloride |
| 4-bromoisobutylbenzene | 5-bromo-2-isobutylbenzyl chloride |
|  | 2-bromo-5-isobutylbenzyl chloride |
| 4-bromo-(1,1,2,2-tetramethylpropyl)benzene | 5-bromo-2-(1,1,2,2-tetramethylpropyl)benzyl chloride |
|  | 2-bromo-5-(1,1,2,2-tetramethylpropyl)benzyl chloride |
| 2-bromo-(1,1,2,2-tetramethylpropyl)benzene | 3-bromo-4-(1,1,2,2-tetramethylpropyl)benzyl chloride |
|  | 3-bromo-2-(1,1,2,2-tetramethylpropyl)benzyl chloride |
|  | 4-bromo-3-(1,1,2,2-tetramethylpropyl)benzyl chloride |
| 2-iodoisopropylbenzene | 3-iodo-4-isopropylbenzyl chloride |
|  | 3-iodo-2-isopropylbenzyl chloride |
|  | 4-iodo-3-isopropylbenzyl chloride |
| 2-fluoroisobutylbenzene | 3-fluoro-4-isobutylbenzyl chloride |
|  | 3-fluoro-2-isobutylbenzyl chloride |
|  | 4-fluoro-3-isobutylbenzyl chloride |
| 3-ethyliodobenzene | 2-ethyl-4-iodobenzyl chloride |
|  | 4-ethyl-2-iodobenzyl chloride |
|  | 3-ethyl-5-iodobenzyl chloride |
| 3-sec-butylfluorobenzene | 2-sec-butyl-4-fluorobenzyl chloride |
|  | 4-sec-butyl-2-fluorobenzyl chloride |
|  | 3-sec-butyl-5-fluorobenzyl chloride |
| 4-tert-butyliodobenzene | 2-tert-butyl-5-iodobenzyl chloride |
|  | 5-tert-butyl-2-iodobenzyl chloride |
| 4-fluoropropylbenzene | 5-fluoro-2-propylbenzyl chloride |
|  | 2-fluoro-5-propylbenzyl chloride |
| 2-chloroisopropylbenzene | 3-chloro-4-isopropylbenzyl chloride |
|  | 3-chloro-2-isopropylbenzyl chloride |
|  | 4-chloro-3-isopropylbenzyl chloride |
| 3-chloroisobutylbenzyl chloride | 4-chloro-2-isobutylbenzyl chloride |
|  | 2-chloro-4-isobutylbenzyl chloride |
|  | 3-chloro-5-isobutylbenzyl chloride |
| 4-chloro-(1,1,2,2-tetramethylpropyl)benzyl chloride | 5-chloro-2-(1,1,2,2-tetramethylpropyl)benzyl chloride |

TABLE I-continued

| Starting Material | Product |
| --- | --- |
| | 2-chloro-5-(1,1,2,2-tetramethylpropyl)benzyl chloride |

EXAMPLE 2

4-Cyano-3-isopropylbenzeneacetonitrile

To a mechanically stirred mixture of 25 parts of 4-bromo-3-isopropylbenzyl chloride and 50 parts of N-methylpyrrolidone is added 22 parts of cuprous cyanide. The mixture is rapidly heated to 200°C and kept at 205°–210°C for 1 hour, then cooled and transferred to a beaker containing ice and water. The mixture is stirred in a Waring blender, collected on a filter and washed with cold water. The thick paste is suspended in water, and 100 parts of methylene chloride is added. Eleven grams of chlorine is slowly passed in under the surface at 15°C. The methylene chloride solution is separated, washed with dilute hydrochloric acid, then with 5% sodium bicarbonate and water, dried and concentrated. The residue is chromatographed and 4-cyano-3-isopropylbenzeneacetonitrile is isolated as one of the fractions.

The following cyanobenzeneacetonitriles are prepared from the listed benzyl chlorides by the above procedure.

EXAMPLE 3

4-Bromo-2-chloro-5-ethylbenzyl Chloride, 4-Bromo-2-chloro-3-ethylbenzyl Chloride, and 4-Bromo-3-chloro-5-ethylbenzyl Chloride To a solution of 46 parts of 4-bromo-3-ethylbenzyl chloride and 3 parts of iodine in 300 parts of chloroform is added 16 parts of chlorine. The solution is refluxed in the absence of light for 6 hours, then cooled and extracted with water and dilute sodium bisulfite solution. The organic phase is separated, dried and concentrated. The residue is chromatographed on Florisil or alumina and 4-bromo-2-chloro-5-ethylbenzyl chloride, 4-bromo-2-chloro-3-ethylbenzyl chloride, and a small amount of 4-bromo-3-chloro-5-ethylbenzyl chloride are isolated as three of the fractions.

The following alkyldihalobenzyl chlorides are prepared from the appropriate alkylmonohalobenzyl chlorides by the above method. Where isomeric mixtures are obtained, the isomers are separated by chromatography.

TABLE II

| Starting Material | Product |
| --- | --- |
| 3-bromo-4-isopropylbenzyl chloride | 3-cyano-4-isopropylbenzeneacetonitrile |
| 3-bromo-4-sec-butylbenzyl chloride | 4-sec-butyl-3-cyanobenzeneacetonitrile |
| 3-bromo-4-tert-butylbenzyl chloride | 4-tert-butyl-3-cyanobenzeneacetonitrile, m.p. 75–76.5°C |
| 3-bromo-4-isobutylbenzyl chloride | 3-cyano-4-isobutylbenzeneacetonitrile |
| 3-bromo-4-ethylbenzyl chloride | 3-cyano-4-ethylbenzeneacetonitrile |
| 3-bromo-2-propylbenzyl chloride | 3-cyano-2-propylbenzeneacetonitrile |
| 3-bromo-2-sec-butylbenzyl chloride | 2-sec-butyl-3-cyanobenzeneacetonitrile |
| 3-bromo-2-tert-butylbenzyl chloride | 2-tert-butyl-3-cyanobenzeneacetonitrile |
| 3-bromo-2-isobutylbenzyl chloride | 3-cyano-2-isobutylbenzeneacetonitrile |
| 3-bromo-2-isopropylbenzyl chloride | 3-cyano-2-isopropylbenzeneacetonitrile |
| 4-bromo-3-isopropylbenzyl chloride | 4-cyano-3-isopropylbenzeneacetonitrile |
| 4-bromo-3-(1,1,2,2-tetramethylpropyl)benzyl chloride | 4-cyano-3-(1,1,2,2-tetramethylpropyl)benzeneacetonitrile |
| 4-bromo-3-sec-butylbenzyl chloride | 3-sec-butyl-4-cyanobenzeneacetonitrile |
| 4-bromo-3-tert-butylbenzyl chloride | 3-tert-butyl-4-cyanobenzeneacetonitrile |
| 4-bromo-3-isobutylbenzyl chloride | 4-cyano-3-isobutylbenzeneacetonitrile |
| 4-bromo-2-ethylbenzyl chloride | 4-cyano-2-ethylbenzeneacetonitrile |
| 4-bromo-2-isopropylbenzyl chloride | 4-cyano-2-isopropylbenzeneacetonitrile |
| 4-bromo-2-sec-butylbenzyl chloride | 2-sec-butyl-4-cyanobenzeneacetonitrile |
| 4-bromo-2-tert-butylbenzyl chloride | 2-tert-butyl-4-cyanobenzeneacetonitrile |
| 4-bromo-2-isobutylbenzyl chloride | 4-cyano-2-isobutylbenzeneacetonitrile |
| 5-bromo-2-isopropylbenzyl chloride | 5-cyano-2-isopropylbenzeneacetonitrile |
| 5-bromo-2-sec-butylbenzyl chloride | 2-sec-butyl-5-cyanobenzeneacetonitrile |
| 5-bromo-2-tert-butylbenzyl chloride | 2-tert-butyl-5-cyanobenzeneacetonitrile |
| 5-bromo-2-isobutylbenzyl chloride | 5-cyano-2-isobutylbenzeneacetonitrile |
| 5-bromo-2-propylbenzyl chloride | 5-cyano-2-propylbenzeneacetonitrile |
| 3-bromo-5-(1,1,2,2-tetramethylpropyl)benzyl chloride | 3-cyano-5-(1,1,2,2-tetramethylpropyl)benzeneacetonitrile |

TABLE III

| Starting Material | Product |
| --- | --- |
| 4-bromo-3-isopropylbenzyl chloride | 4-bromo-3-chloro-5-isopropylbenzyl chloride |
| | 4-bromo-2-chloro-5-isopropylbenzyl chloride |
| | 4-bromo-2-chloro-3-isopropylbenzyl chloride |
| 4-bromo-3-isobutylbenzyl chloride | 4-bromo-3-chloro-5-isobutylbenzyl chloride |
| | 4-bromo-2-chloro-5-isobutylbenzyl chloride |
| | 4-bromo-2-chloro-3-isobutylbenzyl chloride |
| 4-bromo-3-sec-butylbenzyl chloride | 4-bromo-3-sec-butyl-5-chlorobenzyl chloride |
| | 4-bromo-5-sec-butyl-2-chlorobenzyl chloride |
| | 4-bromo-3-sec-butyl-2-chlorobenzyl chloride |
| 4-bromo-2-tert-butylbenzyl chloride | 4-bromo-2-tert-butyl-6-chlorobenzyl chloride |
| | 4-bromo-2-tert-butyl-5-chlorobenzyl chloride |
| | 4-bromo-2-tert-butyl-3-chlorobenzyl chloride |
| 4-bromo-2-ethylbenzyl chloride | 4-bromo-2-chloro-6-ethylbenzyl chloride |
| | 4-bromo-5-chloro-2-ethylbenzyl chloride |

TABLE III-continued

| Starting Material | Product |
|---|---|
| 4-bromo-2-(1,1,2,2-tetramethylpropyl)-benzyl chloride | 4-bromo-3-chloro-2-ethylbenzyl chloride<br>4-bromo-2-chloro-6-(1,1,2,2-tetramethylpropyl)-benzyl chloride<br>4-bromo-5-chloro-2-(1,1,2,2-tetramethylpropyl)-benzyl chloride<br>4-bromo-3-chloro-2-(1,1,2,2-tetramethylpropyl)-benzyl chloride |
| 3-bromo-2-isopropylbenzyl chloride | 3-bromo-6-chloro-2-isopropylbenzyl chloride<br>3-bromo-5-chloro-2-isopropylbenzyl chloride<br>3-bromo-4-chloro-2-isopropylbenzyl chloride |
| 3-bromo-2-sec-butylbenzyl chloride | 3-bromo-2-sec-butyl-6-chlorobenzyl chloride<br>3-bromo-2-sec-butyl-5-chlorobenzyl chloride<br>3-bromo-2-sec-butyl-4-chlorobenzyl chloride |
| 3-bromo-2-ethylbenzyl chloride | 3-bromo-6-chloro-2-ethylbenzyl chloride<br>3-bromo-5-chloro-2-ethylbenzyl chloride<br>3-bromo-4-chloro-2-ethylbenzyl chloride |
| 3-bromo-5-(1,1,2,2-tetramethylpropyl)-benzyl chloride | 5-bromo-2-chloro-3-(1,1,2,2-tetramethylpropyl)-benzyl chloride<br>3-bromo-2-chloro-5-(1,1,2,2-tetramethylpropyl)-benzyl chloride<br>3-bromo-4-chloro-5-(1,1,2,2-tetramethylpropyl)-benzyl chloride |
| 3-bromo-5-tert-butylbenzyl chloride | 5-bromo-3-tert-butyl-2-chlorobenzyl chloride<br>3-bromo-5-tert-butyl-2-chlorobenzyl chloride<br>3-bromo-5-tert-butyl-4-chlorobenzyl chloride |
| 3-bromo-5-isopropylbenzyl chloride | 5-bromo-2-chloro-3-isopropylbenzyl chloride<br>3-bromo-2-chloro-5-isopropylbenzyl chloride<br>3-bromo-4-chloro-5-isopropylbenzyl chloride |
| 5-bromo-2-ethylbenzyl chloride | 3-bromo-2-chloro-6-ethylbenzyl chloride<br>3-bromo-4-chloro-6-ethylbenzyl chloride<br>5-bromo-3-chloro-2-ethylbenzyl chloride |
| 5-bromo-2-tert-butylbenzyl chloride | 3-bromo-6-tert-butyl-2-chlorobenzyl chloride<br>5-bromo-2-tert-butyl-4-chlorobenzyl chloride<br>5-bromo-2-tert-butyl-3-chlorobenzyl chloride |
| 5-bromo-2-sec-butylbenzyl chloride | 3-bromo-6-sec-butyl-2-chlorobenzyl chloride<br>5-bromo-2-sec-butyl-4-chlorobenzyl chloride<br>5-bromo-2-sec-butyl-3-chlorobenzyl chloride |
| 3-bromo-4-isobutylbenzyl chloride | 3-bromo-2-chloro-4-isobutylbenzyl chloride<br>5-bromo-2-chloro-4-isobutylbenzyl chloride<br>3-bromo-5-chloro-4-isobutylbenzyl chloride |
| 3-bromo-4-isopropylbenzyl chloride | 3-bromo-2-chloro-4-isopropylbenzyl chloride<br>5-bromo-2-chloro-4-isopropylbenzyl chloride<br>3-bromo-5-chloro-4-isopropylbenzyl chloride |
| 3-bromo-4-sec-butylbenzyl chloride | 3-bromo-4-sec-butyl-2-chlorobenzyl chloride<br>5-bromo-4-sec-butyl-2-chlorobenzyl chloride<br>3-bromo-4-sec-butyl-5-chlorobenzyl chloride |
| 3-iodo-4-isopropylbenzyl chloride | 2-bromo-3-iodo-4-isopropylbenzyl chloride<br>3-bromo-5-iodo-4-isopropylbenzyl chloride<br>2-bromo-5-iodo-4-isopropylbenzyl chloride |
| 2-iodo-4-(1,1,2,2-tetramethylpropyl)-benzyl chloride | 3-bromo-2-iodo-4-(1,1,2,2-tetramethylpropyl)-benzyl chloride<br>5-bromo-2-iodo-4-(1,1,2,2-tetramethylpropyl)-benzyl chloride<br>2-bromo-6-iodo-4-(1,1,2,2-tetramethylpropyl)-benzyl chloride |
| 5-iodo-6-isobutylbenzyl chloride | 2-bromo-3-iodo-6-isobutylbenzyl chloride<br>4-bromo-5-iodo-2-isobutylbenzyl chloride<br>3-bromo-5-iodo-2-isobutylbenzyl chloride |
| 4-fluoro-3-isopropylbenzyl chloride | 2-bromo-4-fluoro-3-isopropylbenzyl chloride<br>3-bromo-4-fluoro-5-isopropylbenzyl chloride<br>2-bromo-4-fluoro-5-isopropylbenzyl chloride |
| 3-tert-butyl-5-fluorobenzyl chloride | 2-bromo-3-tert-butyl-5-fluorobenzyl chloride<br>4-bromo-3-tert-butyl-5-fluorobenzyl chloride<br>2-bromo-5-tert-butyl-3-fluorobenzyl chloride |
| 2-ethyl-3-fluorobenzyl chloride | 6-bromo-2-ethyl-3-fluorobenzyl chloride<br>5-bromo-2-ethyl-3-fluorobenzyl chloride<br>4-bromo-2-ethyl-3-fluorobenzyl chloride |
| 3-bromo-5-(1,1,2,2-tetramethylpropyl)-benzyl chloride | 2,3-dibromo-5-(1,1,2,2-tetramethylpropyl)-benzyl chloride<br>3,4-dibromo-5-(1,1,2,2-tetramethylpropyl)-benzyl chloride<br>2,5-dibromo-3-(1,1,2,2-tetramethylpropyl)-benzyl chloride |
| 3-bromo-4-isobutylbenzyl chloride | 2,3-dibromo-4-isobutylbenzyl chloride<br>3,5-dibromo-4-isobutylbenzyl chloride<br>2,5-dibromo-4-isobutylbenzyl chloride |
| 4-bromo-2-sec-butylbenzyl chloride | 3,5-dibromo-2-sec-butylbenzyl chloride<br>4,5-dibromo-2-sec-butylbenzyl chloride<br>2,3-dibromo-6-sec-butylbenzyl chloride |

EXAMPLE 4

2-Chloro-4-cyano-5-ethylbenzeneacetonitrile

To a mechanically stirred mixture of 26 parts of 4-bromo-2-chloro-5-ethylbenzyl chloride and 50 parts of N-methylpyrrolidinone is added 22 parts of cuprous cyanide. The mixture is rapidly heated to 200°C and kept at 205°–210°C for 1 hour, then cooled, and the mixture is transferred to a beaker containing ice and water. The mixture is stirred in a Waring blender, collected on a filter and washed with cold water. The thick paste is suspended in water and 150 parts of methylene chloride is added. Eleven grams of chloride is slowly passed in under the surface at 15°C, the methylene chloride solution is separated, washed twice with dilute hydrochloric acid, then with 5% sodium bicarbonate solution, and with water. The solution is dried, filtered and concentrated. The residue is chromatographed and 4-cyano-2-chloro-5-ethylbenzeneacetonitrile is isolated as one of the isomers.

The following benzeneacetonitriles are prepared from the listed benzyl chlorides by the above method.

treated with chlorine in the absence of light until there is no additional gain in weight, then cooled and diluted with methylene chloride. The mixture is filtered, and the filtrate is washed with water and dilute sodium bisulfite, then dried and concentrated. The residue is chromatographed and 3-bromo-2,5-dichloro-4-ethylbenzyl chloride and a small amount of 3-bromo-2,6-dichloro-4-ethylbenzyl chloride are isolated as two of the fractions.

The following alkyltrihalobenzyl chlorides are pre-

TABLE IV

| Starting Material | Product |
| --- | --- |
| 4-bromo-2-chloro-5-isopropylbenzyl chloride | 2-chloro-4-cyano-5-isopropylbenzeneacetonitrile |
| 4-bromo-2-chloro-5-isobutylbenzyl chloride | 2-chloro-4-cyano-5-isobutylbenzeneacetonitrile |
| 4-bromo-3-sec-butyl-2-chlorobenzyl chloride | 3-sec-butyl-2-chloro-4-cyanobenzeneacetonitrile |
| 4-bromo-3-tert-butyl-2-chlorobenzyl chloride | 3-tert-butyl-2-chloro-4-cyanobenzeneacetonitrile |
| 4-bromo-3-chloro-5-isobutylbenzyl chloride | 3-chloro-4-cyano-5-isobutylbenzeneacetonitrile |
| 4-bromo-3-chloro-5-(1,1,2,2-tetramethylpropyl)-benzyl chloride | 3-chloro-4-cyano-5-(1,1,2,2-tetramethylpropyl)-benzeneacetonitrile |
| 4-bromo-5-chloro-2-isobutylbenzyl chloride | 5-chloro-4-cyano-2-isobutylbenzeneacetonitrile |
| 4-bromo-5-chloro-2-ethylbenzyl chloride | 5-chloro-4-cyano-2-ethylbenzeneacetonitrile |
| 4-bromo-3-chloro-2-isopropylbenzyl chloride | 3-chloro-4-cyano-2-isopropylbenzeneacetonitrile |
| 4-bromo-2-sec-butyl-3-chlorobenzyl chloride | 2-sec-butyl-3-chloro-4-cyanobenzeneacetonitrile |
| 4-bromo-2-chloro-6-isopropylbenzyl chloride | 2-chloro-4-cyano-6-isopropylbenzeneacetonitrile |
| 4-bromo-2-chloro-6-ethylbenzyl chloride | 2-chloro-4-cyano-6-ethylbenzeneacetonitrile |
| 3-bromo-5-chloro-2-isopropylbenzyl chloride | 5-chloro-3-cyano-2-isopropylbenzeneacetonitrile |
| 3-bromo-2-sec-butyl-5-chlorobenzyl chloride | 2-sec-butyl-5-chloro-3-cyanobenzeneacetonitrile |
| 3-bromo-4-chloro-2-propylbenzyl chloride | 4-chloro-3-cyano-2-propylbenzeneacetonitrile |
| 3-bromo-4-chloro-2-isopropylbenzyl chloride | 4-chloro-3-cyano-2-isopropylbenzeneacetonitrile |
| 3-bromo-6-chloro-2-ethylbenzyl chloride | 6-chloro-3-cyano-2-ethylbenzeneacetonitrile |
| 3-bromo-6-chloro-2-isobutylbenzyl chloride | 6-chloro-3-cyano-2-isobutylbenzeneacetonitrile |
| 5-bromo-3-tert-butyl-2-chlorobenzyl chloride | 3-tert-butyl-2-chloro-5-cyanobenzeneacetonitrile |
| 5-bromo-3-sec-butyl-2-chlorobenzyl chloride | 3-sec-butyl-2-chloro-5-cyanobenzeneacetonitrile |
| 3-bromo-5-tert-butyl-4-chlorobenzyl chloride | 5-tert-butyl-4-chloro-3-cyanobenzeneacetonitrile |
| 3-bromo-4-chloro-5-isobutylbenzyl chloride | 4-chloro-3-cyano-5-isobutylbenzeneacetonitrile |
| 3-bromo-2-chloro-5-isopropylbenzyl chloride | 2-chloro-3-cyano-5-isopropylbenzeneacetonitrile |
| 3-bromo-2-chloro-5-propylbenzyl chloride | 2-chloro-3-cyano-5-propylbenzeneacetonitrile |
| 5-bromo-3-chloro-2-isobutylbenzyl chloride | 3-chloro-5-cyano-2-isobutylbenzeneacetonitrile |
| 5-bromo-2-sec-butyl-3-chlorobenzyl chloride | 2-sec-butyl-3-chloro-5-cyanobenzeneacetonitrile |
| 3-bromo-4-chloro-6-ethylbenzyl chloride | 4-chloro-3-cyano-6-ethylbenzeneacetonitrile |
| 3-bromo-4-chloro-6-propylbenzyl chloride | 4-chloro-3-cyano-6-propylbenzeneacetonitrile |
| 3-bromo-6-sec-butyl-2-chlorobenzyl chloride | 6-sec-butyl-2-chloro-3-cyanobenzeneacetonitrile |
| 3-bromo-2-chloro-6-isobutylbenzyl chloride | 2-chloro-3-cyano-6-isobutylbenzeneacetonitrile |
| 3-bromo-4-sec-butyl-5-chlorobenzyl chloride | 4-sec-butyl-5-chloro-3-cyanobenzeneacetonitrile |
| 3-bromo-5-chloro-4-(1,1,2,2-tetramethylpropyl)-benzyl chloride | 5-chloro-3-cyano-4-(1,1,2,2-tetramethylpropyl)-benzeneacetonitrile |
| 5-bromo-4-tert-butyl-2-chlorobenzyl chloride | 4-tert-butyl-2-chloro-5-cyanobenzeneacetonitrile |
| 5-bromo-2-chloro-4-ethylbenzyl chloride | 2-chloro-5-cyano-4-ethylbenzeneacetonitrile |
| 3-bromo-2-chloro-4-isobutylbenzyl chloride | 2-chloro-3-cyano-4-isobutylbenzeneacetonitrile |
| 3-bromo-4-tert-butyl-2-chlorobenzyl chloride | 2-chloro-3-cyano-4-isobutylbenzeneacetonitrile |
| 2-bromo-3-iodo-4-isopropylbenzyl chloride | 3-cyano-5-iodo-4-isopropylbenzeneacetonitrile |
| 4-bromo-5-iodo-2-isobutylbenzyl chloride | 4-cyano-5-iodo-2-isobutylbenzeneacetonitrile |
| 3-bromo-4-fluoro-5-ispropylbenzyl chloride | 3-cyano-4-fluoro-5-isopropylbenzeneacetonitrile |
| 5-bromo-2-ethyl-3-fluorobenzyl chloride | 5-cyano-2-ethyl-3-fluorobenzenediacetonitrile |
| 3,5-dibromo-4-isobutylbenzyl chloride | 3-bromo-5-cyano-4-isobutylbenzeneacetonitrile |
| 4,5-dibromo-2-sec-butylbenzyl chloride | 5-bromo-2-sec-butyl-4-cyanobenzeneacetonitrile |
|  | 4-bromo-2-sec-butyl-5-cyanobenzeneacetonitrile |

EXAMPLE 5

3-Bromo-2,5-dichloro-4-ethylbenzyl Chloride and 3-Bromo-2,6-dichloro-4-ethylbenzyl Chloride A mixture of 54 parts of 3-bromo-2-chloro-4-ethylbenzyl chloride and 3 parts of iron filings at 90°–95°C is pared from the listed alkyldihalobenzyl chlorides by the above method. Where isomeric mixtures are formed, the isomers are separated by chromatography.

TABLE V

| Starting Material | Product |
| --- | --- |
| 5-bromo-2-chloro-4-isopropylbenzyl chloride | 5-bromo-2,3-dichloro-4-isopropylbenzyl chloride |
| 5-bromo-2-chloro-4-isobutylbenzyl chloride | 5-bromo-2,3-dichloro-4-isobutylbenzyl chloride |
| 5-bromo-4-sec-butyl-2-chlorobenzyl chloride | 5-bromo-4-sec-butyl-2,3-dichlorobenzyl chloride |
| 3-bromo-2-chloro-4-ethylbenzyl chloride | 3-bromo-2,5-dichloro-4-ethylbenzyl chloride |
|  | 3-bromo-2,6-dichloro-4-ethylbenzyl chloride |
| 3-bromo-4-sec-butyl-2-chlorobenzyl chloride | 3-bromo-4-sec-butyl-2,5-dichlorobenzyl chloride |
|  | 3-bromo-4-sec-butyl-2,6-dichlorobenzyl chloride |
| 3-bromo-2-chloro-6-propylbenzyl chloride | 3-bromo-2,5-dichloro-6-propylbenzyl chloride |
|  | 3-bromo-2,4-dichloro-6-propylbenzyl chloride |
| 3-bromo-2-chloro-6-isobutylbenzyl chloride | 3-bromo-2,5-dichloro-6-isobutylbenzyl chloride |
|  | 3-bromo-2,4-dichloro-6-isobutylbenzyl chloride |
| 5-bromo-2-tert-butyl-4-chlorobenzyl chloride | 5-bromo-2-tert-butyl-3,4-dichlorobenzyl chloride |
| 5-bromo-4-chloro-2-(1,1,2,2-tetramethylpropyl)-benzyl chloride | 5-bromo-3,4-dichloro-2-(1,1,2,2-tetramethylpropyl)-benzyl chloride |
| 4-bromo-2-chloro-6-isopropylbenzyl chloride | 4-bromo-3,6-dichloro-2-isopropylbenzyl chloride |

TABLE V-continued

| Starting Material | Product |
| --- | --- |
| 4-bromo-2-chloro-6-isobutylbenzyl chloride | 4-bromo-2,3-dichloro-6-isopropylbenzyl chloride<br>4-bromo-3,6-dichloro-2-isobutylbenzyl chloride<br>4-bromo-2,3-dichloro-6-isobutylbenzyl chloride |
| 4-bromo-2-sec-butyl-3-chlorobenzyl chloride | 4-bromo-2-sec-butyl-3,5-dichlorobenzyl chloride |
| 4-bromo-2-tert-butyl-3-chlorobenzyl chloride | 4-bromo-2-tert-butyl-3,5-dichlorobenzyl chloride |
| 4-bromo-3-chloro-5-isobutylbenzyl chloride | 4-bromo-2,5-dichloro-3-isobutylbenzyl chloride<br>4-bromo-2,3-dichloro-5-isobutylbenzyl chloride |
| 4-bromo-3-chloro-5-isopropylbenzyl chloride | 4-bromo-2,5-dichloro-3-isopropylbenzyl chloride<br>4-bromo-2,3-dichloro-5-isopropylbenzyl chloride |
| 4-bromo-2-chloro-3-(1,1,2,2-tetramethylpropyl)-benzyl chloride | 4-bromo-2,6-dichloro-3-(1,1,2,2-tetramethylpropyl)-benzyl chloride |
| 4-bromo-3-tert-butyl-2-chlorobenzyl chloride | 4-bromo-3-tert-butyl-2,6-dichlorobenzyl chloride |
| 3-bromo-6-chloro-2-isobutylbenzyl chloride | 3-bromo-5,6-dichloro-2-isobutylbenzyl chloride<br>5-bromo-2,4-dichloro-6-isobutylbenzyl chloride |
| 3-bromo-6-chloro-2-ethylbenzyl chloride | 3-bromo-5,6-dichloro-2-ethylbenzyl chloride<br>5-bromo-2,4-dichloro-6-ethylbenzyl chloride |
| 5-bromo-3-sec-butyl-2-chlorobenzyl chloride | 5-bromo-3-sec-butyl-2,4-dichlorobenzyl chloride<br>3-bromo-5-sec-butyl-2,6-dichlorobenzyl chloride |
| 5-bromo-3-tert-butyl-2-chlorobenzyl chloride | 5-bromo-3-tert-butyl-2,4-dichlorobenzyl chloride<br>3-bromo-5-tert-butyl-2,6-dichlorobenzyl chloride |
| 5-bromo-3-iodo-4-isobutylbenzyl chloride | 5-bromo-2-chloro-3-iodo-4-isobutylbenzyl chloride<br>3-bromo-2-chloro-5-iodo-4-isobutylbenzyl chloride |
| 5-bromo-3-fluoro-4-isopropylbenzyl chloride | 5-bromo-2-chloro-3-fluoro-4-isopropylbenzyl chloride<br>3-bromo-2-chloro-5-fluoro-4-isopropylbenzyl chloride |
| 3,5-dibromo-4-isopropylbenzyl chloride | 2,3,5-tribromo-4-isopropylbenzyl chloride |
| 3-bromo-4-iodo-5-isobutylbenzyl chloride | 3-bromo-2-chloro-4-iodo-5-isobutylbenzyl chloride<br>5-bromo-2-chloro-4-iodo-3-isobutylbenzyl chloride |
| 3-bromo-4-fluoro-5-isopropylbenzyl chloride | 3-bromo-2-chloro-4-fluoro-5-isopropylbenzyl chloride<br>5-bromo-2-chloro-4-fluoro-5-isopropylbenzyl chloride |
| 3,4-dibromo-5-isopropylbenzyl chloride | 2,3,4-tribromo-5-isopropylbenzyl chloride |
| 3-bromo-2-tert-butyl-4-chlorobenzyl chloride | 3-bromo-2-tert-butyl-4,5-dichlorobenzyl chloride<br>3-bromo-2-tert-butyl-4,6-dichlorobenzyl chloride |
| 3-bromo-2-sec-butyl-4-chlorobenzyl chloride | 3-bromo-2-sec-butyl-4,5-dichlorobenzyl chloride<br>3-bromo-2-sec-butyl-4,6-dichlorobenzyl chloride |
| 3-bromo-4-chloro-2-isopropylbenzyl chloride | 3-bromo-4,5-dichloro-2-isopropylbenzyl chloride<br>3-bromo-4,6-dichloro-2-isopropylbenzyl chloride |
| 3-bromo-5-tert-butyl-2-chlorobenzyl chloride | 3-bromo-5-tert-butyl-2,4-dichlorobenzyl chloride<br>3-bromo-5-tert-butyl-2,6-dichlorobenzyl chloride |
| 3-bromo-5-sec-butyl-2-chlorobenzyl chloride | 3-bromo-5-sec-butyl-2,4-dichlorobenzyl chloride<br>3-bromo-5-sec-butyl-2,6-dichlorobenzyl chloride |
| 3-bromo-2-chloro-5-isopropylbenzyl chloride | 3-bromo-2,4-dichloro-5-isopropylbenzyl chloride<br>3-bromo-2,6-dichloro-5-isopropylbenzyl chloride |

The following cyanobenzeneacetonitriles are prepared from the listed benzyl chlorides by the procedure of Example 4. Where isomeric mixtures are formed, the isomers are separated by chromatography.

TABLE VI

| Starting Material | Product |
| --- | --- |
| 5-bromo-2,3-dichloro-4-isopropylbenzyl chloride | 2,3-dichloro-5-cyano-4-isopropylbenzeneacetonitrile |
| 5-bromo-2,3-dichloro-4-isobutylbenzyl chloride | 2,3-dichloro-5-cyano-4-isobutylbenzeneacetonitrile |
| 3-bromo-2,5-dichloro-4-ethylbenzyl chloride | 2,5-dichloro-3-cyano-4-ethylbenzeneacetonitrile |
| 3-bromo-4-sec-butyl-2,5-dichlorobenzyl chloride | 4-sec-butyl-2,5-dichloro-3-cyanobenzeneacetonitrile |
| 3-bromo-2,6-dichloro-4-ethylbenzyl chloride | 2,6-dichloro-3-cyano-4-ethylbenzeneacetonitrile |
| 3-bromo-4-sec-butyl-2,6-dichlorobenzyl chloride | 4-sec-butyl-2,6-dichloro-3-cyanobenzeneacetonitrile |
| 3-bromo-2,5-dichloro-6-isobutylbenzyl chloride | 2,5-dichloro-3-cyano-6-isobutylbenzeneacetonitrile |
| 3-bromo-2,5-dichloro-6-propylbenzyl chloride | 2,5-dichloro-3-cyano-6-propylbenzeneacetonitrile |
| 3-bromo-2,4-dichloro-6-propylbenzyl chloride | 2,4-dichloro-3-cyano-6-propylbenzeneacetonitrile |
| 3-bromo-2,4-dichloro-6-isobutylbenzyl chloride | 2,4-dichloro-3-cyano-6-isobutylbenzeneacetonitrile |
| 5-bromo-2-tert-butyl-3,4-dichlorobenzyl chloride | 2-tert-butyl-3,4-dichloro-5-cyanobenzeneacetonitrile |
| 5-bromo-3,4-dichloro-2-(1,1,2,2-tetramethylpropyl)benzyl chloride | 3,4-dichloro-5-cyano-2-(1,1,2,2-tetramethylpropyl)-benzeneacetonitrile |
| 4-bromo-3,6-dichloro-2-isopropylbenzyl chloride | 3,6-dichloro-4-cyano-2-isopropylbenzeneacetonitrile |
| 4-bromo-3,6-dichloro-2-isobutylbenzyl chloride | 3,6-dichloro-4-cyano-2-isobutylbenzeneacetonitrile |
| 4-bromo-2,3-dichloro-6-isopropylbenzyl chloride | 2,3-dichloro-4-cyano-6-isopropylbenzeneacetonitrile |
| 4-bromo-2,3-dichloro-6-isobutylbenzyl chloride | 2,3-dichloro-4-cyano-6-isobutylbenzeneacetonitrile |
| 4-bromo-2-sec-butyl-3,5-dichlorobenzyl chloride | 2-sec-butyl-3,5-dichloro-4-cyanobenzeneacetonitrile |
| 4-bromo-2-tert-butyl-3,5-dichlorobenzyl chloride | 2-tert-butyl-3,5-dichloro-4-cyanobenzeneacetonitrile |
| 4-bromo-2,5-dichloro-3-isobutylbenzyl chloride | 2,5-dichloro-4-cyano-3-isobutylbenzeneacetonitrile |
| 4-bromo-2,5-dichloro-3-isopropylbenzyl chloride | 2,5-dichloro-4-cyano-3-isopropylbenzeneacetonitrile |
| 4-bromo-2,3-dichloro-5-isobutylbenzyl chloride | 2,3-dichloro-4-cyano-5-isobutylbenzeneacetonitrile |
| 4-bromo-2,3-dichloro-5-isopropylbenzyl chloride | 2,3-dichloro-4-cyano-5-isopropylbenzeneacetonitrile |
| 4-bromo-2,6-dichloro-3-(1,1,2,2-tetramethylpropyl)benzyl chloride | 2,6-dichloro-4-cyano-3-(1,1,2,2-tetramethylpropyl)benzeneacetonitrile |
| 4-bromo-3-tert-butyl-2,6-dichlorobenzyl chloride | 3-tert-butyl-2,6-dichloro-4-cyanobenzeneacetonitrile |
| 3-bromo-5,6-dichloro-2-isobutylbenzyl chloride | 5,6-dichloro-3-cyano-2-isobutylbenzeneacetonitrile |
| 3-bromo-5,6-dichloro-2-ethylbenzyl chloride | 5,6-dichloro-3-cyano-2-ethylbenzeneacetonitrile |
| 5-bromo-2,4-dichloro-6-isobutylbenzyl chloride | 2,4-dichloro-5-cyano-6-isobutylbenzeneacetonitrile |
| 5-bromo-2,4-dichloro-6-ethylbenzyl chloride | 2,4-dichloro-5-cyano-6-ethylbenzeneacetonitrile |
| 5-bromo-3-sec-butyl-2,4-dichlorobenzyl chloride | 3-sec-butyl-2,4-dichloro-5-cyanobenzeneacetonitrile |
| 5-bromo-3-tert-butyl-2,4-dichlorobenzyl chloride | 3-tert-butyl-2,4-dichloro-5-cyanobenzeneacetonitrile |
| 3-bromo-5-sec-butyl-2,6-dichlorobenzyl chloride | 5-sec-butyl-2,6-dichloro-3-cyanobenzeneacetonitrile |
| 3-bromo-5-tert-butyl-2,6-dichlorobenzyl chloride | 5-tert-butyl-2,6-dichloro-3-cyanobenzeneacetonitrile |
| 5-bromo-2-chloro-3-iodo-4-isobutylbenzyl chloride | 2-chloro-5-cyano-3-iodo-4-isobutylbenzeneacetonitrile |
| 5-bromo-2-chloro-3-fluoro-4-isopropylbenzyl | 2-chloro-5-cyano-3-fluoro-4-isopropylbenzeneaceto- |

TABLE VI-continued

| Starting Material | Product |
|---|---|
| chloride | nitrile |
| 2,3,5-tribromo-4-isopropylbenzyl chloride | 2,5-dibromo-3-cyano-4-isopropylbenzeneacetonitrile |
| | 2,3-dibromo-5-cyano-4-ispropylbenzeneacetonitrile |
| 3-bromo-2-tert-butyl-4,5-dichlorobenzyl chloride | 2-tert-butyl-4,5-dichloro-3-cyanobenzeneacetonitrile |
| 3-bromo-2-sec-butyl-4,5-dichlorobenzyl chloride | 2-sec-butyl-4,5-dichloro-3-cyanobenzeneacetonitrile |
| 3-bromo-4,5-dichloro-2-isopropylbenzyl chloride | 4,5-dichloro-3-cyano-2-isopropylbenzeneacetonitrile |
| 3-bromo-5-tert-butyl-2,4-dichlorobenzyl chloride | 5-tert-butyl-2,4-dichloro-3-cyanobenzeneacetonitrile |
| 3-bromo-5-sec-butyl-2,4-dichlorobenzyl chloride | 5-sec-butyl-2,4-dichloro-3-cyanobenzeneacetonitrile |
| 3-bromo-2,4-dichloro-5-isopropylbenzyl chloride | 2,4-dichloro-3-cyano-5-isopropylbenzeneacetonitrile |

EXAMPLE 6

4-Cyano-5-ethyl-2-nitrobenzeneacetonitrile

A mixture of 146 parts of nitronium tetrafluoroborate and 600 parts of tetramethylene sulfone is stirred at 10°–20°C to produce a homogeneous suspension, and 198 parts of 4-cyano-3-ethylbenzeneacetonitrile is added portionwise in 20–30 minutes. As the reaction proceeds, the salt dissolves and the product separates. The cooling bath is removed and stirring is continued for 15 minutes at 30°–35°C. The mixture is then poured into ice water and the product collected, washed and dried.

In a similar manner, using the appropriate starting materials, one can prepare the compounds shown in the following table.

In many cases nitration yields mixtures of isomers. These need not be separated for the purposes of this invention, but they can be separated by chromatography if desired.

TABLE VII

| Starting Material | Product |
|---|---|
| 4-cyano-3-methylbenzeneacetonitrile | 4-cyano-5-methyl-2-nitrobenzeneacetonitrile |
| 4-cyano-3-isopropylbenzeneacetonitrile | 4-cyano-5-isopropyl-2-nitrobenzeneacetonitrile |
| 4-cyano-3-isobutylbenzeneacetonitrile | 4-cyano-5-isobutyl-2-nitrobenzeneacetonitrile |
| 4-cyano-3-neopentylbenzeneacetonitrile | 4-cyano-5-neopentyl-2-nitrobenzeneacetonitrile |
| 4-cyano-3-(1,2-dimethylpropyl)benzeneacetonitrile | 4-cyano-5-(1,2-dimethylpropyl)-2-nitrobenzeneacetonitrile |
| 3-butyl-4-cyanobenzeneacetonitrile | 5-butyl-4-cyano-2-nitrobenzeneacetonitrile |
| 3-sec-butyl-4-cyanobenzeneacetonitrile | 5-sec-butyl-4-cyano-2-nitrobenzeneacetonitrile |
| 3-tert-butyl-4-cyanobenzeneacetonitrile | 5-tert-butyl-4-cyano-2-nitrobenzeneacetonitrile |
| 4-cyano-3-propylbenzeneacetonitrile | 4-cyano-2-nitro-5-propylbenzeneacetonitrile |
| 4-cyano-2-methylbenzeneacetonitrile | 4-cyano-2-methyl-5-nitrobenzeneacetonitrile |
| 4-cyano-2-isopropylbenzeneacetonitrile | 4-cyano-2-isopropyl-5-nitrobenzeneacetonitrile, m.p. 101–103°C |
| 4-cyano-2-isobutylbenzeneacetonitrile | 4-cyano-2-isobutyl-5-nitrobenzeneacetonitrile |
| 4-cyano-2-propylbenzeneacetonitrile | 4-cyano-5-nitro-2-propylbenzeneacetonitrile |
| 2-tert-butyl-4-cyanobenzeneacetonitrile | 2-tert-butyl-4-cyano-5-nitrobenzeneacetonitrile |
| 2-sec-butyl-4-cyanobenzeneacetonitrile | 2-sec-butyl-4-cyano-5-nitrobenzeneacetonitrile |
| 2-butyl-4-cyanobenzeneacetonitrile | 2-butyl-4-cyano-5-nitrobenzeneacetonitrile |
| 5-cyano-2-methylbenzeneacetonitrile | 5-cyano-2-methyl-3-nitrobenzeneacetonitrile |
| 5-cyano-2-ethylbenzeneacetonitrile | 5-cyano-2-ethyl-3-nitrobenzeneacetonitrile |
| 5-cyano-2-isopropylbenzeneacetonitrile | 5-cyano-2-isopropyl-3-nitrobenzeneacetonitrile |
| 5-cyano-2-isobutylbenzeneacetonitrile | 5-cyano-2-isobutyl-3-nitrobenzeneacetonitrile |
| 2-butyl-5-cyanobenzeneacetonitrile | 2-butyl-5-cyano-3-nitrobenzeneacetonitrile |
| 2-tert-butyl-5-cyanobenzeneacetonitrile | 2-tert-butyl-5-cyano-3-nitrobenzeneacetonitrile |
| 2-sec-butyl-5-cyanobenzeneacetonitrile | 2-sec-butyl-5-cyano-3-nitrobenzeneacetonitrile |
| 3-cyano-5-isobutylbenzeneacetonitrile | 3-cyano-5-isobutyl-2-nitrobenzeneacetonitrile |
| | 3-cyano-5-isobutyl-4-nitrobenzeneacetonitrile |
| | 3-cyano-5-isobutyl-6-nitrobenzeneacetonitrile |
| 3-cyano-5-isopropylbenzeneacetonitrile | 3-cyano-5-isopropyl-2-nitrobenzeneacetonitrile |
| | 3-cyano-5-isopropyl-4-nitrobenzeneacetonitrile |
| | 3-cyano-5-isopropyl-6-nitrobenzeneacetonitrile |
| 2-butyl-3-cyanobenzeneacetonitrile | 2-butyl-3-cyano-6-nitrobenzeneacetonitrile |
| | 2-butyl-3-cyano-5-nitrobenzeneacetonitrile |
| | 2-butyl-3-cyano-4-nitrobenzeneacetonitrile |
| 2-cyano-2-propylbenzeneacetonitrile | 3-cyano-6-nitro-2-propylbenzeneacetonitrile |
| | 3-cyano-4-nitro-2-propylbenzeneacetonitrile |
| | 3-cyano-5-nitro-2-propylbenzeneacetonitrile |
| 2,5-dibromo-3-butyl-4-cyanobenzeneacetonitrile | 2,5-dibromo-3-butyl-4-cyano-6-nitrobenzeneacetonitrile |
| 2,5-dibromo-6-butyl-4-cyanobenzeneacetonitrile | 2,5-dibromo-6-butyl-4-cyano-3-nitrobenzeneacetonitrile |
| 2,6-dibromo-3-butyl-4-cyanobenzeneacetonitrile | 2,6-dibromo-3-butyl-4-cyano-5-nitrobenzeneacetonitrile |
| 3,5-dibromo-2-butyl-4-cyanobenzeneacetonitrile | 3,5-dibromo-2-butyl-4-cyano-6-nitrobenzeneacetonitrile |
| 2,3-dibromo-5-butyl-4-cyanobenzeneacetonitrile | 2,3-dibromo-5-butyl-4-cyano-6-nitrobenzeneacetonitrile |
| 2,3-dibromo-6-butyl-4-cyanobenzeneacetonitrile | 2,3-dibromo-6-butyl-4-cyano-5-nitrobenzeneacetonitrile |
| 2,5-dichloro-3-cyano-4-isopropylbenzeneacetonitrile | 2,5-dichloro-3-cyano-4-isopropyl-6-nitrobenzeneacetonitrile |
| 2,5-dichloro-3-cyano-6-isopropylbenzeneacetonitrile | 2,5-dichloro-3-cyano-6-isopropyl-4-nitrobenzeneacetonitrile |
| 3,4-dichloro-5-cyano-2-isopropylbenzeneacetonitrile | 3,4-dichloro-5-cyano-2-isopropyl-6-nitrobenzeneacetonitrile |
| 2,3-dichloro-5-cyano-4-isopropylbenzeneacetonitrile | 2,3-dichloro-5-cyano-4-isopropyl-6-nitrobenzeneacetonitrile |
| 2,4-dichloro-5-cyano-3-isopropylbenzeneacetonitrile | 2,4-dichloro-5-cyano-3-isopropyl-6-nitrobenzeneacetonitrile |
| 2,3-dichloro-5-cyano-6-isopropylbenzeneacetonitrile | 2,3-dichloro-5-cyano-6-isopropyl-4-nitrobenzeneacetonitrile |
| 2,4-dichloro-3-cyano-6-isopropylbenzeneacetonitrile | 2,4-dichloro-3-cyano-6-isopropyl-5-nitrobenzeneacetonitrile |
| 2,6-dichloro-3-cyano-4-isopropylbenzeneacetonitrile | 2,6-dichloro-3-cyano-4-isopropyl-5-nitrobenzeneacetonitrile |
| 4,5-dichloro-3-cyano-2-isopropylbenzeneacetonitrile | 4,5-dichloro-3-cyano-2-isopropyl-6-nitrobenzene- |

TABLE VII-continued

| Starting Material | Product |
|---|---|
| nitrile | acetonitrile |
| 2,4-dichloro-3-cyano-5-isopropylbenzeneaceto-nitrile | 2,4-dichloro-3-cyano-5-isopropyl-6-nitrobenzene-acetonitrile |
| 2,6-dichloro-3-cyano-5-isopropylbenzeneaceto-nitrile | 2,6-dichloro-3-cyano-5-isopropyl-4-nitrobenzene-acetonitrile |
| 4,6-dichloro-3-cyano-2-isopropylbenzeneaceto-nitrile | 4,6-dichloro-3-cyano-2-isopropyl-5-nitrobenzene-acetonitrile |

EXAMPLE 7

4-Cyano-5-ethyl-2,6-dinitrobenzeneacetonitrile

A mixture of 243 parts of 4-cyano-5-ethyl-2-nitrobenzeneacetonitrile, 700 parts of tetramethylene sulfone, and 169 parts of nitronium tetrafluoroborate is stirred under reflux and heated until the temperature is between 110°–115°C. This temperature is maintained for one hour; the mixture is allowed to cool and is poured into ice water. The crude dinitro product is isolated by filtration, washed and dried.

Alternatively, the above compound is prepared from 4-cyano-3-ethylbenzeneacetonitrile without isolating 4-cyano-5-ethyl-2-nitrobenzeneacetonitrile. In this case, a mixture of 315 parts of nitronium tetrafluoroboroate is stirred in 900 parts of tetramethylene sulfone at 10°–20°C to produce a homogeneous suspension, and 198 parts of 4-cyano-3-ethylbenzeneacetonitrile is added portionwise. After completion of the addition, the mixture is allowed to warm to room temperature and is heated under reflux until the temperature is between 110°–115°C. This temperature is maintained for one hour and the product is then treated as described above.

Similarly, the dinitro compounds shown in the following tables are prepared by the procedures of this example.

TABLE VIII

| Starting Material | Product |
|---|---|
| 4-cyano-5-methyl-2-nitrobenzeneacetonitrile | 4-cyano-5-methyl-2,6-dinitrobenzeneacetonitrile |
| 4-cyano-5-isopropyl-2-nitrobenzeneacetonitrile | 4-cyano-5-isopropyl-2,6-dinitrobenzeneacetonitrile |
| 4-cyano-5-neopentyl-2-nitrobenzeneacetonitrile | 4-cyano-5-neopentyl-2,6-dinitrobenzeneacetonitrile |
| 4-cyano-3-isobutylbenzeneacetonitrile | 4-cyano-3-isobutyl-2,6-dinitrobenzeneacetonitrile |
| 4-cyano-2-methylbenzeneacetonitrile | 4-cyano-2-methyl-3,6-dinitrobenzeneacetonitrile |
| 4-cyano-2-isopropylbenzeneacetonitrile | 4-cyano-2-isopropyl-3,6-dinitrobenzeneacetonitrile |
| 4-cyano-2-isobutylbenzeneacetonitrile | 4-cyano-2-isobutyl-3,6-dinitrobenzeneacetonitrile |
| 2-tert-butyl-4-cyanobenzeneacetonitrile | 2-tert-butyl-4-cyano-3,6-dinitrobenzeneacetonitrile |
| 3-sec-butyl-4-cyano-5-nitrobenzeneacetonitrile | 3-sec-butyl-4-cyano-2,5-dinitrobenzeneacetonitrile |
| 4-cyano-3-ethyl-5-nitrobenzeneacetonitrile | 4-cyano-3-ethyl-2,5-dinitrobenzeneacetonitrile |
| 4-cyano-3-isopropyl-5-nitrobenzeneacetonitrile | 4-cyano-2-isopropyl-2,5-dinitrobenzeneacetonitrile |
| 4-cyano-2-isopropyl-5-nitrobenzeneacetonitrile | 4-cyano-2-isopropyl-3,5-dinitrobenzeneacetonitrile |
| 4-cyano-2-isobutyl-5-nitrobenzeneacetonitrile | 4-cyano-2-isobutyl-3,5-dinitrobenzeneacetonitrile |
| 2-sec-butyl-4-cyano-5-nitrobenzeneacetonitrile | 2-sec-butyl-4-cyano-3,5-dinitrobenzeneacetonitrile |
| 4-sec-butyl-3-cyano-5-nitrobenzeneacetonitrile | 4-sec-butyl-3-cyano-2,5-dinitrobenzeneacetonitrile |
| 3-cyano-4-isobutyl-5-nitrobenzeneacetonitrile | 3-cyano-4-isobutyl-2,5-dinitrobenzeneacetonitrile |
| 2-butyl-5-cyano-3-nitrobenzeneacetonitrile | 2-butyl-5-cyano-3,6-dinitrobenzeneacetonitrile |
| 2-tert-butyl-5-cyano-3-nitrobenzeneacetonitrile | 2-tert-butyl-5-cyano-3,6-dinitrobenzeneacetonitrile |
| 2-sec-butyl-3-cyano-4-nitrobenzeneacetonitrile | 2-sec-butyl-3-cyano-4,6-dinitrobenzeneacetonitrile |
| 3-sec-butyl-4-cyano-5-fluorobenzeneacetonitrile | 3-sec-butyl-4-cyano-5-fluoro-2,6-nitrobenzeneacetonitrile |
| 5-chloro-4-cyano-3-ethylbenzeneacetonitrile | 5-chloro-4-cyano-3-ethyl-2,6-dinitrobenzeneacetonitrile |
| 2-butyl-6-chloro-4-cyanobenzeneacetonitrile | 2-butyl-6-chloro-4-cyano-3,5-dinitrobenzeneacetontrile |
| 2-chloro-4-cyano-6-isopropylbenzeneacetonitrile | 2-chloro-4-cyano-6-isopropyl-3,5-dinitrobenzeneacetonitrile |
| 2-butyl-4-cyano-5-fluorobenzeneacetonitrile | 2-butyl-4-cyano-5-fluoro-3,6-dinitrobenzeneacetonitrile |
| 2-butyl-5-chloro-4-cyanobenzeneacetonitrile | 2-butyl-5-chloro-4-cyano-3,6-dinitrobenzeneacetonitrile |
| 2-bromo-5-butyl-4-cyanobenzeneacetonitrile | 2-bromo-5-butyl-4-cyano-3,6-dinitrobenzeneacetonitrile |
| 2-bromo-4-cyano-5-isobutylbenzeneacetonitrile | 2-bromo-4-cyano-5-isobutyl-3,6-dinitrobenzeneacetonitrile |
| 5-bromo-4-butyl-3-cyanobenzeneacetonitrile | 5-bromo-4-butyl-3-cyano-2,6-dinitrobenzeneacetonitrile |
| 5-bromo-4-sec-butyl-3-cyanobenzeneacetonitrile | 5-bromo-4-sec-butyl-3-cyano-2,6-dinitrobenzeneacetonitrile |
| 2-butyl-3-chloro-5-cyanobenzeneacetonitrile | 2-butyl-3-chloro-5-cyano-4,6-dinitrobenzeneacetonitrile |
| 5-cyano-2-ethyl-3-fluorobenzeneacetonitrile | 5-cyano-2-ethyl-3-fluoro-4,6-dinitrobenzeneacetonitrile |
| 2-butyl-3-cyano-5-fluorobenzeneacetonitrile | 2-butyl-3-cyano-5-fluoro-4,6-dinitrobenzeneacetonitrile |
| 5-chloro-3-cyano-2-ethylbenzeneacetonitrile | 5-chloro-3-cyano-2-ethyl-4,6-dinitrobenzeneacetonitrile |
| 2-chloro-5-cyano-4-isopropylbenzeneacetonitrile | 2-chloro-5-cyano-4-isopropyl-3,6-dinitrobenzene-acetonitrile |
| 2-chloro-5-cyano-4-ethylbenzeneacetonitrile | 2-chloro-5-cyano-4-ethyl-3,6-dinitrobenzeneaceto-nitrile |
| 4-bromo-5-butyl-3-cyanobenzeneacetonitrile | 4-bromo-5-butyl-3-cyano-2,6-dinitrobenzeneaceto-nitrile |
| 2-bromo-3-sec-butyl-5-cyanobenzeneacetonitrile | 2-bromo-3-sec-butyl-5-cyano-4,6-dinitrobenzene-acetonitrile |
| 2-bromo-3-cyano-5-isopropylbenzeneacetonitrile | 2-bromo-3-cyano-5-isopropyl-4,6-dinitrobenzene-acetonitrile |
| 2-butyl-4-chloro-5-cyanobenzeneacetonitrile | 2-butyl-4-chloro-5-cyano-3,6-dinitrobenzeneaceto-nitrile |
| 3-tert-butyl-5-cyanobenzeneacetonitrile | 3-tert-butyl-5-cyano-2,6-dinitrobenzeneacetonitrile |
| | 3-tert-butyl-5-cyano-2,4-dinitrobenzeneacetonitrile |
| | 5-tert-butyl-3-cyano-2,4-dinitrobenzeneacetonitrile |

EXAMPLE 8

3-Bromo-2-tert-butyl-5-nitrobenzyl Chloride

A mixture of 30 parts of 2-bromo-1-tert-butyl-4-nitrobenzene and 30 parts of chloromethylmethyl ether is stirred vigorously while adding dropwise 20 parts of 60% fuming sulfuric acid. The resultant mixture is allowed to stand until the apparent reaction ceases and is then poured into ice water. The solid is removed by filtration and washed with water to give 3-bromo-2-tert-butyl-5-nitrobenzyl chloride.

The benzyl chlorides listed in Table IX are prepared by the above procedure from starting materials disclosed in the preceding examples. Where isomer mixtures are obtained, they can be used as such or separated into the component isomers by chromatography or distillation. The benzyl chlorides are converted to benzeneacetonitriles by reaction with cuprous cyanide according to the method of Example 2, as shown in Table X.

and dissolved in 10% sodium hydroxide solution. The aqueous base solution is washed with ether and acidified, precipitating essentially pure 2-chloro-4-carboxy-6-propylphenylacetic acid.

Part B

4-Carboxy-2-chloro-3-nitro-6-propylphenylacetic Acid and 4-Carboxy-2-chloro-5-nitro-6-propylphenylacetic Acid To a mixture of 100 parts of 90% nitric acid and 200 parts of fuming sulfuric acid is added portionwise 20 parts of 4-carboxy-2-chloro-6-propylphenylacetic acid. The resulting solution is heated on a steam bath for 2 hours then poured into an ice-water mixture. The resulting isomeric mixture of 4-carboxy-2-chloro-3-nitro-

TABLE IV

| Starting Material | Product |
| --- | --- |
| 2-bromo-1-butyl-4-nitrobenzene | 3-bromo-2-butyl-5-nitrobenzyl chloride |
| 2-bromo-1-sec-butyl-4-nitrobenzene | 3-bromo-2-sec-butyl-5-nitrobenzyl chloride |
| 2-bromo-1-isobutyl-4-nitrobenzene | 3-bromo-2-isobutyl-5-nitrobenzyl chloride |
| 2-bromo-1-isopropyl-4-nitrobenzene | 3-bromo-2-isopropyl-5-nitrobenzyl chloride |
| 2-bromo-1-ethyl-4-nitrobenzene | 3-bromo-2-ethyl-5-nitrobenzyl chloride |
| 2-bromo-1-methyl-4-nitrobenzene | 3-bromo-2-methyl-5-nitrobenzyl chloride |
| 2-bromo-4-nitro-1-propylbenzene | 3-bromo-5-nitro-2-propylbenzyl chloride |
| 1-bromo-2-butyl-3-nitrobenzene | 3-bromo-4-butyl-5-nitrobenzyl chloride |
| 1-bromo-2-tert-butyl-3-nitrobenzene | 3-bromo-4-tert-butyl-5-nitrobenzyl chloride |
| 1-bromo-2-sec-butyl-3-nitrobenzene | 3-bromo-4-sec-butyl-5-nitrobenzyl chloride |
| 1-bromo-2-isobutyl-3-nitrobenzene | 3-bromo-4-isobutyl-5-nitrobenzyl chloride |
| 1-bromo-2-isopropyl-3-nitrobenzene | 3-bromo-4-isopropyl-5-nitrobenzyl chloride |
| 1-bromo-3-nitro-2-propylbenzene | 3-bromo-5-nitro-4-propylbenzyl chloride |
| 1-bromo-2-butyl-4-nitrobenzene | 5-bromo-4-butyl-2-nitrobenzyl chloride |
| 1-bromo-2-tert-butyl-4-nitrobenzene | 5-bromo-4-tert-butyl-2-nitrobenzyl chloride |
| 1-bromo-2-sec-butyl-4-nitrobenzene | 5-bromo-4-sec-butyl-2-nitrobenzyl chloride |
| 1-bromo-2-isobutyl-4-nitrobenzene | 5-bromo-4-isobutyl-2-nitrobenzyl chloride |
| 1-bromo-2-isopropyl-4-nitrobenzene | 5-bromo-4-isopropyl-2-nitrobenzyl chloride |
| 1-bromo-4-nitro-2-propylbenzene | 5-bromo-4-nitro-2-propylbenzyl chloride |
| 2-bromo-1-butyl-3-nitrobenzene | 3-bromo-2-butyl-4-nitrobenzyl chloride |
| 2-bromo-1-ethyl-3-nitrobenzene | 3-bromo-2-ethyl-4-nitrobenzyl chloride |
| 2-bromo-1-methyl-3-nitrobenzene | 3-bromo-2-methyl-4-nitrobenzyl chloride |
| 2-bromo-3-nitro-1-propylbenzene | 3-bromo-4-nitro-2-propylbenzyl chloride |
| 2-bromo-1-isobutyl-3-nitrobenzene | 3-bromo-2-isobutyl-4-nitrobenzyl chloride |
| 2-bromo-1-isopropyl-3-nitrobenzene | 3-bromo-2-isopropyl-4-nitrobenzyl chloride |
| 1-bromo-2-nitro-4-propylbenzene | 5-bromo-4-nitro-2-propylbenzyl chloride |
| 1-bromo-4-butyl-2-nitrobenzene | 5-bromo-2-butyl-4-nitrobenzyl chloride |
| 1-bromo-4-tert-butyl-2-nitrobenzene | 5-bromo-2-tert-butyl-4-nitrobenzyl chloride |
| 1-bromo-4-sec-butyl-2-nitrobenzene | 5-bromo-2-sec-butyl-4-nitrobenzyl chloride |
| 1-bromo-4-isobutyl-2-nitrobenzene | 5-bromo-2-isobutyl-4-nitrobenzyl chloride |
| 1-bromo-4-isopropyl-2-nitrobenzene | 5-bromo-2-ispropyl-4-nitrobenzyl chloride |

TABLE X

| Starting Material | Product |
| --- | --- |
| 3-bromo-2-butyl-5-nitrobenzyl chloride | 2-butyl-3-cyano-5-nitrobenzeneacetonitrile |
| 3-bromo-2-sec-butyl-5-nitrobenzyl chloride | 2-sec-butyl-3-cyano-5-nitrobenzeneacetonitrile |
| 3-bromo-2-isobutyl-5-nitrobenzyl chloride | 3-cyano-2-isobutyl-5-nitrobenzeneacetonitrile |
| 3-bromo-2-isopropyl-5-nitrobenzyl chloride | 3-cyano-2-isopropyl-5-nitrobenzeneacetonitrile |
| 3-bromo-2-ethyl-5-nitrobenzyl chloride | 3-cyano-2-ethyl-5-nitrobenzeneacetonitrile |
| 3-bromo-2-methyl-5-nitrobenzyl chloride | 3-cyano-2-methyl-5-nitrobenzeneacetonitrile |
| 3-bromo-5-nitro-2-propylbenzyl chloride | 3-cyano-5-nitro-2-propylbenzeneacetonitrile |
| 3-bromo-4-butyl-5-nitrobenzyl chloride | 4-butyl-3-cyano-5-nitrobenzeneacetonitrile |
| 3-bromo-4-tert-butyl-5-nitrobenzyl chloride | 4-tert-butyl-3-cyano-5-nitrobenzeneacetonitrile |
| 5-bromo-4-butyl-2-nitrobenzyl chloride | 4-butyl-5-cyano-2-nitrobenzeneacetonitrile |
| 5-bromo-4-tert-butyl-2-nitrobenzyl chloride | 4-tert-butyl-5-cyano-2-nitrobenzeneacetonitrile |
| 3-bromo-2-butyl-4-nitrobenzyl chloride | 2-butyl-3-cyano-4-nitrobenzeneacetonitrile |
| 3-bromo-2-ethyl-4-nitrobenzyl chloride | 3-cyano-2-ethyl-4-nitrobenzeneacetonitrile |
| 3-bromo-2-isopropyl-4-nitrobenzyl chloride | 3-cyano-2-isopropyl-4-nitrobenzeneacetonitrile |
| 5-bromo-2-butyl-4-nitrobenzyl chloride | 2-butyl-5-cyano-4-nitrobenzeneacetonitrile |
| 5-bromo-2-isobutyl-4-nitrobenzyl chloride | 5-cyano-2-isobutyl-4-nitrobenzeneacetonitrile |

EXAMPLE 9

Part A

4-Carboxy-2-chloro-6-propylphenylacetic Acid

A mixture of 50 parts of 2-chloro-4-cyano-6-propylbenzeneacetonitrile and 200 parts of concentrated sulfuric acid is warmed on a steam bath for 1 hour then poured into ice water. The resulting solid is collected 6-propylphenylacetic acid and 4-carboxy-2-chloro-5-nitro-6-propylphenylacetic acid is dried and used in Part C without further purification.

Part C

2-Chloro-4-chlorocarbonyl-3-nitro-6-propylphenylacetyl chloride and 2-Chloro-4-chlorocarbonyl-5-nitro-6-propylphenylacetyl chloride

To 300 parts of thionyl chloride is added dropwise and with cooling 20 parts of the crude mixture of 2-chloro-4-carboxy-3 (or 5)-nitro-6-propylphenylacetic acids from Part B. The mixture is refluxed until no further evolution of gases is observed. The thionyl chloride is distilled and the residue vacuum distilled, affording essentially pure 2-chloro-4-chlorocarbonyl-3-nitro-6-propylphenylacetyl chloride and the corresponding 5-nitro isomer in separate fractions.

Part D

4-Carboxamido-2-chloro-3-nitro-6-propylphenylacetamide

Into a cold solution of 10 parts of 2-chloro-4-chlorocarbonyl-3-nitro-6-propylphenylacetyl chloride in 200 parts of ether is passed dry ammonia. The resulting precipitate is collected, stirred in 2% sodium hydroxide, filtered, washed with water and recrystallized, affording pure 4-carboxamido-2-chloro-3-nitro-6-propylphenylacetamide.

By the same procedure, 4-carboxamido-2-chloro-5-nitro-6-propylphenylacetamide can be prepared.

Part E

2-Chloro-4-cyano-3-nitro-6-propylbenzeneacetonitrile

A mixture of 5 parts of 4-carboxamido-2-chloro-3-nitro-6-propylphenylacetamide and 100 parts of phosphorus oxychloride is refluxed for 1 hour. The excess phosphorus oxychloride is removed by vacuum distillation and the residue is poured into ice water. The solid is collected, washed with water and recrystallized, affording essentially pure 2-chloro-4-cyano-3-nitro-6-propylbenzeneacetonitrile.

2-Chloro-4-cyano-5-nitro-6-propylbenzeneacetonitrile can be prepared by the same method.

The nitrated cyanobenzeneacetonitriles of the following table can be prepared by starting with the listed chlorinated cyanobenzeneacetonitriles, rather than with 2-chloro-4-cyano-6-propylbenzeneacetonitrile of Part A.

In those cases in which more than one isomer is possible, separation can be effected by fractional distillation or chromatography at any convenient step, or the product can be isolated as a mixture of isomers and used without separation.

TABLE XI

| Starting Material | Product |
| --- | --- |
| 2-chloro-4-cyano-6-isobutylbenzeneacetonitrile | 6-chloro-4-cyano-2-isobutyl-3-nitrobenzeneacetonitrile<br>2-chloro-4-cyano-6-isobutyl-3-nitrobenzeneacetonitrile |
| 2-chloro-4-cyano-6-propylbenzeneacetonitrile | 2-chloro-4-cyano-3-nitro-6-propylbenzeneacetonitrile<br>6-chloro-4-cyano-3-nitro-2-propylbenzeneacetonitrile |
| 2-tert-butyl-6-chloro-4-cyanobenzeneacetonitrile | 6-tert-butyl-2-chloro-4-cyano-3-nitrobenzeneacetonitrile |
| 2-chloro-4-cyano-6-ethylbenzeneacetonitrile | 2-chloro-4-cyano-6-ethyl-3-nitrobenzeneacetonitrile<br>6-chloro-4-cyano-2-ethyl-3-nitrobenzeneacetonitrile |
| 3-chloro-5-cyano-2-ethylbenzeneacetonitrile | 3-chloro-5-cyano-2-ethyl-4-nitrobenzeneacetonitrile<br>3-chloro-5-cyano-2-ethyl-6-nitrobenzeneacetonitrile |
| 3-chloro-5-cyano-2-isobutylbenzeneacetonitrile | 3-chloro-5-cyano-2-isobutyl-4-nitrobenzeneacetonitrile<br>3-chloro-5-cyano-2-isobutyl-6-nitrobenzeneacetonitrile |
| 3-chloro-5-cyano-2-propylbenzeneacetonitrile | 3-chloro-5-cyano-4-nitro-2-propylbenzeneacetonitrile<br>3-chloro-5-cyano-6-nitro-2-propylbenzeneacetonitrile |
| 2-tert-butyl-3-chloro-5-cyanobenzeneacetonitrile | 2-tert-butyl-3-chloro-5-cyano-4-nitrobenzeneacetonitrile<br>2-tert-butyl-3-chloro-5-cyano-6-nitrobenzeneacetonitrile |
| 2-chloro-5-cyano-3-ethylbenzeneacetonitrile | 2-chloro-5-cyano-3-ethyl-4-nitrobenzeneacetonitrile<br>2-chloro-5-cyano-3-ethyl-6-nitrobenzeneacetonitrile |
| 2-chloro-5-cyano-3-propylbenzeneacetonitrile | 2-chloro-5-cyano-4-nitro-3-propylbenzeneacetonitrile<br>2-chloro-5-cyanao-6-nitro-3-propylbenzeneacetonitrile |
| 2-chloro-5-cyano-3-isobutylbenzeneacetonitrile | 2-chloro-5-cyano-3-isobutyl-4-nitrobenzeneacetonitrile<br>2-chloro-5-cyano-3-isobutyl-6-nitrobenzeneacetonitrile |
| 3-tert-butyl-2-chloro-5-cyanobenzeneacetonitrile | 3-tert-butyl-2-chloro-5-cyano-4-nitrobenzeneacetonitrile<br>3-tert-butyl-2-chloro-5-cyano-6-nitrobenzeneacetonitrile |
| 2-chloro-4-cyano-3,6-diethylbenzeneacetonitrile | 2-chloro-4-cyano-3,6-diethyl-5-nitrobenzeneacetonitrile |
| 2-chloro-4-cyano-3,6-dipropylbenzeneacetonitrile | 2-chloro-4-cyano-5-nitro-3,6-dipropylbenzeneacetonitrile |
| 2-chloro-4-cyano-3,6-diisobutylbenzeneacetonitrile | 2-chloro-4-cyano-3,6-diisobutyl-5-nitrobenzeneacetonitrile |
| 2-chloro-4-cyano-3-ethyl-6-propylbenzeneacetonitrile | 2-chloro-4-cyano-3-ethyl-5-nitro-6-propylbenzeneacetonitrile |
| 2-chloro-4-cyano-3-ethyl-6-isobutylbenzeneacetonitrile | 2-chloro-4-cyano-3-ethyl-6-isobutyl-5-nitrobenzeneacetonitrile |
| 2-chloro-4-cyano-6-isobutyl-3-ispropyl-benzeneacetonitrile | 2-chloro-4-cyano-6-isobutyl-3-isopropyl-5-nitrobenzeneacetonitrile |
| 2-chloro-4-cyano-6-isobutyl-3-propyl-benzeneacetonitrile | 2-chloro-4-cyano-6-isobutyl-5-nitro-3-propylbenzeneacetonitrile |
| 2-chloro-4-cyano-3-isobutyl-6-propyl-benzeneacetonitrile | 2-chloro-4-cyano-3-isobutyl-5-nitro-6-propylbenzeneacetonitrile |
| 6-tert-butyl-2-chloro-4-cyano-3-isobutyl-benzeneacetonitrile | 6-tert-butyl-2-chloro-4-cyano-3-isobutyl-5-nitrobenzeneacetonitrile |
| 3-chloro-4-cyano-2,6-diethylbenzeneacetonitrile | 3-chloro-4-cyano-2,6-diethyl-5-nitrobenzeneacetonitrile |
| 3-chloro-4-cyano-2,6-diisobutylbenzeneacetonitrile | 3-chloro-4-cyano-2,6-diisobutyl-5-nitrobenzeneacetonitrile |
| 3-chloro-4-cyano-2,6-dipropylbenzeneacetonitrile | 3-chloro-4-cyano-5-nitro-2,6-dipropylbenzeneacetonitrile |
| 2-tert-butyl-3-chloro-4-cyano-6-propyl-benzeneacetonitrile | 2-tert-butyl-3-chloro-4-cyano-5-nitro-6-propylbenzeneacetonitrile |
| 2-tert-butyl-3-chloro-4-cyano-6-isobutyl-benzeneacetonitrile | 2-tert-butyl-3-chloro-4-cyano-6-isobutyl-5-nitrobenzeneacetonitrile |

TABLE XI-continued

| Starting Material | Product |
| --- | --- |
| 3-chloro-5-cyano-2,4-diethylbenzeneacetonitrile | 3-chloro-5-cyano-2,4-diethyl-6-nitrobenzeneacetonitrile |
| 3-chloro-5-cyano-2,4-diisobutylbenzeneacetonitrile | 3-chloro-5-cyano-2,4-diisobutyl-6-nitrobenzeneacetonitrile |
| 3-chloro-5-cyano-2,4-dipropylbenzeneacetonitrile | 3-chloro-5-cyano-6-nitro-2,4-dipropylbenzeneacetonitrile |
| 3-chloro-5-cyano-2-ethyl-4-isobutylbenzeneacetonitrile | 3-chloro-5-cyano-2-ethyl-4-isobutyl-6-nitrobenzeneacetonitrile |
| 2-tert-butyl-3-chloro-5-cyano-4-propylbenzeneacetonitrile | 2-tert-butyl-3-chloro-5-cyano-6-nitro-4-propylbenzeneacetonitrile |
| 3-chloro-5-cyano-2,6-diethylbenzeneacetonitrile | 3-chloro-5-cyano-2,6-diethyl-4-nitrobenzeneacetonitrile |
| 3-bromo-5-cyano-2,6-diisobutylbenzeneacetonitrile | 3-bromo-5-cyano-2,6-diisobutyl-4-nitrobenzeneacetonitrile |
| 3-chloro-5-cyano-2,6-diisobutylbenzeneacetonitrile | 3-chloro-5-cyano-2,6-diisobutyl-4-nitrobenzeneacetonitrile |
| 2,6-di-tert-butyl-3-chloro-5-cyanobenzeneacetonitrile | 2,6-di-tert-butyl-3-chloro-5-cyano-4-nitrobenzeneacetonitrile |
| 2-tert-butyl-3-chloro-5-cyano-6-isobutylbenzeneacetonitrile | 2-tert-butyl-3-chloro-5-cyano-6-isobutyl-4-nitrobenzeneacetonitrile |
| 6-tert-butyl-3-chloro-5-cyano-2-isobutylbenzeneacetonitrile | 6-tert-butyl-3-chloro-5-cyano-2-isobutyl-4-nitrobenzeneacetonitrile |
| 2-chloro-5-cyano-3,6-dipropylbenzeneacetonitrile | 2-chloro-5-cyano-4-nitro-3,6-dipropylbenzeneacetonitrile |
| 2-chloro-5-cyano-3,6-diisobutylbenzeneacetonitrile | 2-chloro-5-cyano-3,6-diisobutyl-4-nitrobenzeneacetonitrile |
| 2-chloro-5-cyano-3,6-diethylbenzeneacetonitrile | 2-chloro-5-cyano-3,6-diethyl-4-nitrobenzeneacetonitrile |
| 3-tert-butyl-2-chloro-5-cyano-6-ethylbenzeneacetonitrile | 3-tert-butyl-2-chloro-5-cyano-6-ethyl-4-nitrobenzeneacetonitrile |
| 3-tert-butyl-2-chloro-5-cyano-6-propylbenzeneacetonitrile | 3-tert-butyl-2-chloro-5-cyano-4-nitro-6-propylbenzeneacetonitrile |
| 6-tert-butyl-2-chloro-5-cyano-3-isobutylbenzeneacetonitrile | 6-tert-butyl-2-chloro-5-cyano-3-isobutyl-4-nitrobenzeneacetonitrile |

EXAMPLE 10

5-Chloro-4-cyano-6-nitro-2-propylbenzeneacetonitrile

To 38 parts of 90% nitric acid is added portionwise 5 parts of 5-chloro-4-cyano-2-propylbenzeneacetonitrile at such a rate that the temperature does not exceed 50°C. The solution is stirred for 2 hr at room temperature then poured into ice water. The organic phase is extracted with ether and the ethereal solution washed with water, 2% sodium hydroxide and water. The dried ethereal solution is vacuum distilled to remove solvent and the residue is recrystallized, to afford pure 5-chloro-4-cyano-6-nitro-2-propylbenzenediacetonitrile.

By replacing 5-chloro-4-cyano-6-nitro-2-propylbenzeneacetonitrile with the following benzeneacetonitriles, the following products are obtained. In some cases, nitrated isomer mixtures are obtained. These can be separated by fractional crystallization, chromatography, distillation or other techniques, but the mixtures themselves are useful in the compositions and methods of this invention.

TABLE XII

| Starting Material | Product |
| --- | --- |
| 5-chloro-4-cyano-2-ethylbenzeneacetonitrile | 5-chloro-4-cyano-2-ethyl-6-nitrobenzeneacetonitrile |
| 5-bromo-4-cyano-2-ethylbenzeneacetonitrile | 5-bromo-4-cyano-2-ethyl-6-nitrobenzeneacetonitrile |
| 5-chloro-4-cyano-2-propylbenzeneacetonitrile | 5-chloro-4-cyano-6-nitro-2-propylbenzeneacetonitrile |
| 5-bromo-4-cyano-2-propylbenzeneacetonitrile | 5-bromo-4-cyano-6-nitro-2-propylbenzeneacetonitrile |
| 5-chloro-4-cyano-2-isobutylbenzeneacetonitrile | 5-chloro-4-cyano-2-isobutyl-6-nitrobenzeneacetonitrile |
| 4-cyano-5-fluoro-2-isobutylbenzeneacetonitrile | 4-cyano-5-fluoro-2-isobutyl-6-nitrobenzeneacetonitrile |
| 5-bromo-4-cyano-2-isobutylbenzeneacetonitrile | 5-bromo-4-cyano-2-isobutyl-6-nitrobenzeneacetonitrile |
| 2-tert-butyl-5-chloro-4-cyanobenzeneacetonitrile | 2-tert-butyl-5-chloro-4-cyano-6-nitrobenzeneacetonitrile |
| 5-bromo-2-tert-butyl-4-cyanobenzeneacetonitrile | 5-bromo-2-tert-butyl)-4-cyano-6-nitrobenzeneacetonitrile |
| 5-chloro-4-cyano-2-tert-pentylbenzeneacetonitrile | 5-chloro-4-cyano-6-nitro-2-tert-pentylbenzeneacetonitrile |
| 5-chloro-4-cyano-2-(1,2-dimethylpropyl)benzeneacetonitrile | 5-chloro-4-cyano-2-(1,2-dimethylpropyl)-6-nitrobenzeneacetonitrile |
| 5-chloro-4-cyano-2-(1,1,2-trimethylproyl)-benzeneacetonitrile | 5-chloro-4-cyano-2-(1,1,2-trimethylpropyl)-6-nitrobenzeneacetonitrile |
| 2-chloro-4-cyano-3-ethylbenzeneacetonitrile | 2-chloro-4-cyano-3-ethyl-6-nitrobenzeneacetonitrile |
| 2-chloro-4-cyano-3-propylbenzeneacetonitrile | 2-chloro-4-cyano-3-propyl-6-nitrobenzeneacetonitrile |
| 2-bromo-4-cyano-3-propylbenzeneacetonitrile | 2-bromo-4-cyano-3-propyl-6-nitrobenzeneacetonitrile |
| 4-cyano-2-fluoro-3-isopropylbenzeneacetonitrile | 4-cyano-2-fluoro-3-isopropyl-6-nitrobenzeneacetonitrile |
| 2-chloro-4-cyano-3-isopropylbenzeneacetonitrile | 2-chloro-4-cyano-3-isopropyl-6-nitrobenzeneacetonitrile |
| 2-bromo-4-cyano-3-isopropylbenzeneacetonitrile | 2-bromo-4-cyano-3-isopropyl-6-nitrobenzeneacetonitrile |
| 2-chloro-4-cyano-3-isobutylbenzeneacetonitrile | 2-chloro-4-cyano-3-isobutyl-6-nitrobenzeneacetonitrile |
| 2-bromo-4-cyano-3-isobutylbenzeneacetonitrile | 2-bromo-4-cyano-3-isobutyl-6-nitrobenzeneacetonitrile |
| 3-tert-butyl-2-chloro-4-cyanobenzeneacetonitrile | 3-tert-butyl-2-chloro-4-cyano-6-nitrobenzeneacetonitrile |
| 2-bromo-3-tert-butyl-4-cyanobenzeneacetonitrile | 2-bromo-3-tert-butyl-4-cyano-6-nitrobenzeneacetonitrile |
| 5-chloro-4-cyano-3-ethylbenzeneacetonitrile | 5-chloro-4-cyano-3-ethyl-2-nitrobenzeneacetonitrile<br>3-chloro-4-cyano-5-ethyl-2-nitrobenzeneacetonitrile |
| 5-bromo-4-cyano-3-ethylbenzeneacetonitrile | 5-bromo-4-cyano-3-ethyl-2-nitrobenzeneacetonitrile<br>3-bromo-4-cyano-5-ethyl-2-nitrobenzeneacetonitrile |
| 5-chloro-4-cyano-3-propylbenzeneacetonitrile | 5-chloro-4-cyano-2-nitro-3-propylbenzeneacetonitrile<br>3-chloro-4-cyano-2-nitro-5-propylbenzeneacetonitrile |
| 5-bromo-4-cyano-3-propylbenzeneacetonitrile | 5-bromo-4-cyano-2-nitro-3-propylbenzeneacetonitrile<br>3-bromo-4-cyano-2-nitro-5-proplybenzeneacetonirile |
| 5-bromo-4-cyano-3-isopropylbenzeneacetonitrile | 5-bromo-4-cyano-3-isopropyl-2-nitrobenzeneacetonitrile<br>3-bromo-4-cyano-5-isopropyl-2-nitrobenzeneacetonitrile |

TABLE XII-continued

| Starting Material | Product |
| --- | --- |
| 5-chloro-4-cyano-3-isopropylbenzeneacetonitrile | 5-chloro-4-cyano-3-isopropyl-2-nitrobenzeneacetonitrile |
| | 3-chloro-4-cyano-5-isopropyl-2-nitrobenzeneacetonitrile |
| 4-cyano-5-fluoro-3-isopropylbenzeneacetonitrile | 4-cyano-5-fluoro-3-isopropyl-2-nitrobenzeneacetonitrile |
| | 4-cyano-3-fluoro-5-isopropyl-2-nitrobenzeneacetonitrile |
| 5-chloro-4-cyano-3-isobutylbenzeneacetonitrile | 5-chloro-4-cyano-3-isobutyl-2-nitrobenzeneacetonitrile |
| | 3-chloro-4-cyano-5-isobutyl-2-nitrobenzeneacetonitrile |
| 5-bromo-4-cyano-3-isobutylbenzeneacetonitrile | 5-bromo-4-cyano-3-isobutyl-2-nitrobenzeneacetonitrile |
| | 3-bromo-4-cyano-5-isobutyl-2-nitrobenzeneacetonitrile |
| 3-sec-butyl-5-chloro-4-cyanobenzeneacetonitrile | 3-sec-butyl-5-chloro-4-cyano-2-nitrobenzeneacetonitrile |
| | 5-sec-butyl-3-chloro-4-cyano-2-nitrobenzeneacetonitrile |
| 5-bromo-3-sec-butyl-4-cyanobenzeneacetonitrile | 5-bromo-3-sec-butyl-4-cyano-2-nitrobenzeneacetonitrile |
| | 3-bromo-5-sec-butyl-4-cyano-2-nitrobenzeneacetonitrile |
| 3-tert-butyl-3-chloro-4-cyanobenzeneacetonitrile | 3-tert-butyl-5-chloro-4-cyano-2-nitrobenzeneacetonitrile |
| | 5-tert-butyl-3-chloro-4-cyano-2-nitrobenzeneacetonitrile |
| 5-bromo-3-tert-butyl-4-cyanobenzeneacetonitrile | 5-bromo-3-tert-butyl-4-cyano-2-nitrobenzeneacetonitrile |
| | 3-bromo-5-tert-butyl-4-cyano-2-nitrobenzeneacetonitrile |
| 5-chloro-4-cyano-3-tert-pentylbenzeneacetonitrile | 5-chloro-4-cyano-2-nitro-3-tert-pentylbenzeneacetonitrile |
| | 3-chloro-4-cyano-2-nitro-5-tert-pentylbenzeneacetonitrile |
| 2-chloro-4-cyano-5-ethylbenzeneacetonitrile | 2-chloro-4-cyano-5-ethyl-6-nitrobenzeneacetonitrile |
| 2-bromo-4-cyano-5-ethylbenzeneacetonitrile | 2-bromo-4-cyano-5-ethyl-6-nitrobenzeneacetonitrile |
| 2-chloro-4-cyano-5-propylbenzeneacetonitrile | 2-chloro-4-cyano-6-nitro-5-propylbenzeneacetonitrile |
| 2-bromo-4-cyano-5-propylbenzeneacetonitrile | 2-bromo-4-cyano-6-nitro-5-propylbenzeneacetonitrile |
| 2-chloro-4-cyano-5-isopropylbenzeneacetonitrile | 2-chloro-4-cyano-5-isopropyl-6-nitrobenzeneacetonitrile |
| 2-bromo-4-cyano-5-isopropylbenzeneacetonitrile | 2-bromo-4-cyano-5-isopropyl-6-nitrobenzeneacetonitrile |
| 2-chloro-4-cyano-5-isobutylbenzeneacetonitrile | 2-chloro-4-cyano-5-isobutyl-6-nitrobenzeneacetonitrile |
| 2-bromo-4-cyano-5-isobutylbenzeneacetonitrile | 2-bromo-4-cyano-5-isobutyl-6-nitrobenzeneacetonitrile |
| 2-bromo-5-tert-butyl-4-cyanobenzeneacetonitrile | 2-bromo-5-tert-butyl-4-cyano-6-nitrobenzeneacetonitrile |
| 5-tert-butyl-2-chloro-4-cyanobenzeneacetonitrile | 5-tert-butyl-2-chloro-4-cyano-6-nitrobenzeneacetonitrile |
| 2-chloro-4-cyano-5-tert-pentylbenzeneacetonitrile | 2-chloro-4-cyano-6-nitro-5-tert-pentylbenzeneacetonitrile |
| 2-bromo-4-cyano-5-tert-pentylbenzeneacetonitrile | 2-bromo-4-cyano-6-nitro-5-tert-pentylbenzeneacetonitrile |
| 2-chloro-4-cyano-5-(1,2-dimethylpropyl)benzene-acetonitrile | 2-chloro-4-cyano-5-(1,2-dimethylpropyl)-6-nitrobenzene-acetonitrile |
| 3-chloro-4-cyano-2-ethylbenzeneacetonitrile | 3-chloro-4-cyano-2-ethyl-6-nitrobenzeneacetonitrile |
| 3-bromo-4-cyano-2-ethylbenzeneacetonitrile | 3-bromo-4-cyano-2-ethyl-6-nitrobenzeneacetonitrile |
| 3-chloro-4-cyano-2-propylbenzeneacetonitrile | 3-chloro-4-cyano-6-nitro-2-propylbenzeneacetonitrile |
| 3-bromo-4-cyano-2-propylbenzeneacetonitrile | 3-bromo-4-cyano-6-nitro-2-propylbenzeneacetonitrile |
| 3-chloro-4-cyano-2-isobutylbenzeneacetonitrile | 3-chloro-4-cyano-2-isobutyl-6-nitrobenzeneacetonitrile |
| 3-bromo-4-cyano-2-isobutylbenzeneacetonitrile | 3-bromo-4-cyano-2-isobutyl-6-nitrobenzeneacetonitrile |
| 3-bromo-2-tert-butyl-4-cyanobenzeneacetonitrile | 3-bromo-2-tert-butyl-4-cyano-6-nitrobenzeneacetonitrile |
| 2-tert-butyl-3-chloro-4-cyanobenzeneacetonitrile | 2-tert-butyl-3-chloro-4-cyano-6-nitrobenzeneacetonitrile |
| 3-chloro-4-cyano-2-tert-pentylbenzeneacetonitrile | 3-chloro-4-cyano-6-nitro-2-tert-pentylbenzeneacetonitrile |
| 4-chloro-5-cyano-2-ethylbenzeneacetonitrile | 4-chloro-5-cyano-2-ethyl-3-nitrobenzeneacetonitrile |
| 4-bromo-5-cyano-2-propylbenzeneacetonitrile | 4-bromo-5-cyano-3-nitro-2-propylbenzeneacetonitrile |
| 4-chloro-5-cyano-2-propylbenzeneacetonitrile | 4-chloro-5-cyano-3-nitro-2-propylbenzeneacetonitrile |
| 4-chloro-5-cyano-2-isobutylbenzeneacetonitrile | 4-chloro-5-cyano-2-isobutyl-3-nitrobenzeneacetonitrile |
| 4-bromo-5-cyano-2-isobutylbenzeneacetonitrile | 4-bromo-5-cyano-2-isobutyl-3-nitrobenzeneacetonitrile |
| 2-tert-butyl-4-chloro-5-cyanobenzeneacetonitrile | 2-tert-butyl-4-chloro-5-cyano-3-nitrobenzeneacetonitrile |
| 4-bromo-2-tert-butyl-5-cyanobenzeneacetonitrile | 4-bromo-2-tert-butyl-5-cyano-3-nitrobenzeneacetonitrile |
| 4-bromo-5-cyano-2-tert-pentylbenzeneacetonitrile | 4-bromo-5-cyano-3-nitro-2-tert-pentylbenzeneacetonitrile |
| 4-chloro-3-cyano-2-ethylbenzeneacetonitrile | 4-chloro-3-cyano-2-ethyl-5-nitrobenzeneacetonitrile |
| | 4-chloro-3-cyano-2-ethyl-6-nitrobenzeneacetonitrile |
| 4-chloro-3-cyano-2-propylbenzeneacetonitrile | 4-chloro-3-cyano-5-nitro-2-propylbenzeneacetonitrile |
| | 4-chloro-3-cyano-6-nitro-2-propylbenzeneacetonitrile |
| 4-bromo-3-cyano-2-propylbenzeneacetonitrile | 4-bromo-3-cyano-5-nitro-2-propylbenzeneacetonitrile |
| | 4-bromo-3-cyano-6-nitro-2-propylbenzeneacetonitrile |
| 4-chloro-3-cyano-2-isopropylbenzeneacetonitrile | 4-chloro-3-cyano-2-isopropyl-5-nitrobenzeneacetonitrile |
| | 4-chloro-3-cyano-2-isopropyl-6-nitrobenzeneacetonitrile |
| 4-bromo-3-cyano-2-isopropylbenzeneacetonitrile | 4-bromo-3-cyano-2-isopropyl-5-nitrobenzeneacetonitrile |
| | 4-bromo-3-cyano-2-isopropyl-6-nitrobenzeneacetonitrile |
| 4-chloro-3-cyano-2-isobutylbenzeneacetonitrile | 4-chloro-3-cyano-2-isobutyl-5-nitrobenzeneacetonitrile |
| | 4-chloro-3-cyano-2-isobutyl-6-nitrobenzeneacetonitrile |
| 4-bromo-3-cyano-2-isobutylbenzeneacetonitrile | 4-bromo-3-cyano-2-isobutyl-5-nitrobenzeneacetonitrile |
| | 4-bromo-3-cyano-2-isobutyl-6-nitrobenzeneacetonitrile |
| 4-bromo-2-sec-butyl-3-cyanobenzeneacetonitrile | 4-bromo-2-sec-butyl-3-cyano-5-nitrobenzeneacetonitrile |
| | 4-bromo-2-sec-butyl-3-cyano-6-nitrobenzeneacetonitrile |
| 2-sec-butyl-4-chloro-3-cyanobenzeneacetonitrile | 2-sec-butyl-4-chloro-3-cyano-5-nitrobenzeneacetonitrile |
| | 2-sec-butyl-4-chloro-3-cyano-6-nitrobenzeneacetonitrile |
| 5-chloro-3-cyano-4-propylbenzeneacetonitrile | 3-chloro-5-cyano-2-nitro-4-propylbenzeneacetonitrile |
| 5-chloro-3-cyano-4-isopropylbenzeneacetonitrile | 3-chloro-5-cyano-4-isopropyl-2-nitrobenzeneacetonitrile |
| 5-bromo-3-cyano-4-isopropylbenzeneacetonitrile | 3-bromo-5-cyano-4-isopropyl-2-nitrobenzeneacetonitrile |
| 3-cyano-5-fluoro-4-isobutylbenzeneacetonitrile | 5-cyano-3-fluoro-4-isobutyl-2-nitrobenzeneacetonitrile |
| 5-chloro-3-cyano-4-isobutylbenzeneacetonitrile | 3-chloro-5-cyano-4-isobutyl-2-nitrobenzeneacetonirile |
| 5-bromo-3-cyano-4-isobutylbenzeneacetonitrile | 3-bromo-5-cyano-4-isobutyl-2-nitrobenzeneacetonitrile |
| 4-sec-butyl-5-chloro-3-cyanobenzeneacetonitrile | 4-sec-butyl-3-chloro-5-cyano-2-nitrobenzeneacetonitrile |
| 4-tert-butyl-5-chloro-3-cyanobenzeneacetonitrile | 4-tert-butyl-3-chloro-5-cyano-2-nitrobenzeneacetonitrile |
| 5-chloro-3-cyano-4-tert-pentylbenzeneacetonitrile | 3-chloro-5-cyano-2-nitro-4-tert-pentylbenzeneacetonitrile |
| 2-chloro-3-cyano-5-ethylbenzeneacetonitrile | 2-chloro-3-cyano-5-ethyl-6-nitrobenzeneacetonitrile |
| 2-bromo-3-cyano-5-propylbenzeneacetonitrile | 2-bromo-3-cyano-6-nitro-5-propylbenzeneacetonitrile |
| 2-chloro-3-cyano-5-propylbenzeneacetonitrile | 2-chloro-3-cyano-6-nitro-5-propylbenzeneacetnitrile |
| 2-chloro-3-cyano-5-isobutylbenzeneacetonitrile | 2-chloro-3-cyano-5-isobutyl-6-nitrobenzeneacetonitrile |
| 2-bromo-3-cyano-5-isobutylbenzeneacetonitrile | 2-bromo-3-cyano-5-isobutyl-6-nitrobenzeneacetonitrile |
| 2-bromo-5-tert-butyl-3-cyanobenzeneacetonitrile | 2-bromo-5-tert-butyl-3-cyano-6-nitrobenzeneacetonitrile |
| 2-tert-butyl-4-chloro-3-cyanobenzeneacetonitrile | 2-tert-butyl-4-chloro-3-cyano-5-nitrobenzeneacetonitrile |
| | 2-tert-butyl-4-chloro-3-cyano-6-nitrobenzeneacetonitrile |
| 4-bromo-2-tert-butyl-3-cyanobenzeneacetonitrile | 4-bromo-2-tert-butyl-3-cyano-5-nitrobenzeneacetonitrile |
| | 4-bromo-2-tert-butyl-3-cyano-6-nitrobenzeneacetonitrile |
| 2-chloro-5-cyano-4-ethylbenzeneacetonitrile | 2-chloro-5-cyano-4-ethyl-3-nitrobenzeneacetonitrile |
| 2-chloro-5-cyano-4-propylbenzeneacetonitrile | 2-chloro-5-cyano-3-nitro-4-propylbenzeneacetonitrile |
| 2-chloro-5-cyano-4-isopropylbenzeneacetonirile | 2-chloro-5-cyano-4-isopropyl-3-nitrobenzeneacetonirile |
| 2-bromo-5-cyano-4-isopropylbenzeneacetonitrile | 2-bromo-5-cyano-4-isopropyl-3-nitrobenzeneacetonitrile |
| 2-chloro-5-cyano-4-isobutylbenzeneacetonitrile | 2-chloro-5-cyano-4-isobutyl-3-nitrobenzeneacetonitrile |

TABLE XII-continued

| Starting Material | Product |
| --- | --- |
| 2-bromo-5-cyano-4-isobutylbenzeneacetonitrile | 2-bromo-5-cyano-4-isobutyl-3-nitrobenzeneacetonitrile |
| 4-sec-butyl-2-chloro-5-cyanobenzeneacetonitrile | 4-sec-butyl-2-chloro-5-cyano-3-nitrobenzeneacetonitrile |
| 2-bromo-4-sec-butyl-5-cyanobenzeneacetonitrile | 2-bromo-4-sec-butyl-5-cyano-3-nitrobenzeneacetonitrile |
| 4-tert-butyl-2-chloro-5-cyanobenzeneacetonitrile | 4-tert-butyl-2-chloro-5-cyano-3-nitrobenzeneacetonitrile |
| 2-bromo-4-tert-butyl-5-cyanobenzeneacetonitrile | 2-bromo-4-tert-butyl-5-cyano-3-nitrobenzeneacetonitrile |
| 2-bromo-5-cyano-4-tert-pentylbenzeneacetonitrile | 2-bromo-5-cyano-3-nitro-4-tert-pentylbenzeneacetonirile |
| 6-chloro-3-cyano-2-ethylbenzeneacetonitrile | 6-chloro-3-cyano-2-ethyl-5-nitrobenzeneacetonitrile |
| 6-bromo-3-cyano-2-propylbenzeneacetonitrile | 6-bromo-3-cyano-5-nitro-2-propylbenzeneacetonitrile |
| 6-chloro-3-cyano-2-propylbenzeneacetonitrile | 6-chloro-3-cyano-5-nitro-2-propylbenzeneacetonitrile |
| 6-chloro-3-cyano-2-ispropylbenzeneacetonitrile | 6-chloro-3-cyano-2-isopropyl-5-nitrobenzeneacetonitrile |
| 6-bromo-3-cyano-2-isopropylbenzeneacetonitrile | 6-bromo-3-cyano-2-isopropyl-5-nitrobenzeneacetonitrile |
| 6-chloro-3-cyano-2-isobutylbenzeneacetonitrile | 6-chloro-3-cyano-2-isobutyl-5-nitrobenzeneacetonitrile |
| 6-bromo-3-cyano-2-isobutylbenzeneacetonitrile | 6-bromo-3-cyano-2-isobutyl-5-nitrobenzeneacetonitrile |
| 6-bromo-2-sec-butyl-3-cyanobenzeneacetonitrile | 6-bromo-2-sec-butyl-3-cyano-5-nitrobenzeneacetonitrile |
| 2-tert-butyl-6-chloro-3-cyanobenzeneacetonitrile | 2-tert-butyl-6-chloro-3-cyano-5-nitrobenzeneacetonitrile |
| 6-chloro-3-cyano-2-tert-pentylbenzeneacetonitrile | 6-chloro-3-cyano-5-nitro-2-tert-pentylbenzeneacetonitrile |
| 5-chloro-3-cyano-2-ethylbenzeneacetonitrile | 5-chloro-3-cyano-2-ethyl-6-nitrobenzeneacetonitrile |
| 5-chloro-3-cyano-2-propylbenzeneacetonitrile | 5-chloro-3-cyano-6-nitro-2-propylbenzeneacetonitrile |
| 5-bromo-3-cyano-2-isopropylbenzeneacetonitrile | 5-bromo-3-cyano-2-isopropyl-6-nitrobenzeneacetonitrile |
| 5-chloro-3-cyano-2-isopropylbenzeneacetonitrile | 5-chloro-3-cyano-2-isopropyl-6-nitrobenzeneacetonitrile |
| 2-tert-butyl-5-chloro-3-cyanobenzeneacetonitrile | 2-tert-butyl-5-chloro-3-cyano-6-nitrobenzeneacetonitrile |
| 5-chloro-3-cyano-2-isobutylbenzeneacetonitrile | 5-chloro-3-cyano-2-isobutyl-6-nitrobenzeneacetonitrile |
| 5-bromo-3-cyano-2-isobutylbenzeneacetonitrile | 5-bromo-3-cyano-2-isobutyl-6-nitrobenzeneacetonitrile |
| 3-cyano-5-fluoro-2-isobutylbenzeneacetonitrile | 3-cyano-5-fluoro-2-isobutyl-6-nitrobenzeneacetonitrile |
| 2-chloro-3-cyano-4-ethylbenzeneacetonitrile | 2-chloro-3-cyano-4-ethyl-5-nitrobenzeneacetonitrile |
| | 2-chloro-3-cyano-4-ethyl-6-nitrobenzeneacetonitrile |
| 2-chloro-3-cyano-4-propylbenzeneacetonitrile | 2-chloro-3-cyano-5-nitro-4-propylbenzeneactonitrile |
| | 2-chloro-3-cyano-6-nitro-4-propylbenzeneacetonitrile |
| 2-bromo-3-cyano-4-isopropylbenzeneacetonitrile | 2-bromo-3-cyano-4-isopropyl-5-nitrobenzeneacetonitrile |
| | 2-bromo-3-cyano-4-isopropyl-6-nitrobenzeneacetonitrile |
| 2-chloro-3-cyano-4-isopropylbenzeneacetonitrile | 2-chloro-3-cyano-4-isopropyl-5-nitrobenzeneacetonitrile |
| | 2-chloro-3-cyano-4-isopropyl-6-nitrobenzeneacetonitrile |
| 2-chloro-3-cyano-4-isobutylbenzeneacetonitrile | 2-chloro-3-cyano-4-isobutyl-5-nitrobenzeneacetonitrile |
| | 2-chloro-3-cyano-4-isobutyl-6-nitrobenzeneacetonitrile |
| 2-bromo-3-cyano-4-isobutylbenzeneacetonitrile | 2-bromo-3-cyano-4-isobutyl-5-nitrobenzeneacetonitrile |
| | 2-bromo-3-cyano-4-isobutyl-6-nitrobenzeneacetonitrile |
| 4-tert-butyl-2-chloro-3-cyanobenzeneacetonitrile | 4-tert-butyl-2-chloro-3-cyano-5-nitrobenzeneacetonitrile |
| | 4-tert-butyl-2-chloro-3-cyano-6-nitrobenzeneacetonitrile |
| 2-chloro-3-cyano-4-tert-pentylbenzeneacetonitrile | 2-chloro-3-cyano-5-nitro-4-tert-pentylbenzeneacetonitrile |
| | 2-chloro-3-cyano-6-nitro-4-tert-pentylbenzeneacetonitrile |
| 5-chloro-3-cyano-4-ethylbenzeneacetonitrile | 3-chloro-5-cyano-4-ethyl-2-nitrobenzeneacetonitrile |
| 5-tert-butyl-2-chloro-3-cyanobenzeneacetonitrile | 5-tert-butyl-2-chloro-3-cyano-6-nitrobenzeneacetonitrile |
| 2-chloro-3-cyano-6-ethylbenzeneacetonitrile | 2-chloro-3-cyano-6-ethyl-5-nitrobenzeneacetonitrile |
| 2-chloro-3-cyano-6-propylbenzeneacetonitrile | 2-chloro-3-cyano-5-nitro-6-propylbenzeneacetonitrile |
| 2-bromo-3-cyano-6-isobutylbenzeneacetonitrile | 2-bromo-3-cyano-6-isobutyl-5-nitrobenzeneacetonitrile |
| 2-chloro-3-cyano-6-isobutylbenzeneacetonitrile | 2-chloro-3-cyano-6-isobutyl-5-nitrobenzeneacetonitrile |
| 2-bromo-6-tert-butyl-3-cyanobenzeneacetonitrile | 2-bromo-6-tert-butyl-3-cyano-5-nitrobenzeneacetonitrile |
| 6-tert-butyl-2-chloro-3-cyanobenzeneacetonitrile | 6-tert-butyl-2-chloro-3-cyano-5-nitrobenzeneacetonitrile |
| 2-chloro-3-cyano-6-tert-pentylbenzeneacetonitrile | 2-chloro-3-cyano-5-nitro-6-tert-pentylbenzeneacetonitrile |
| 4-chloro-3-cyano-5-ethylbenzeneacetonitrile | 4-chloro-5-cyano-3-ethyl-6-nitrobenzeneacetonitrile |
| 4-chloro-3-cyano-5-propylbenzeneacetonitrile | 4-chloro-5-cyano-6-nitro-3-propylbenzeneacetonitrile |
| 4-bromo-3-cyano-5-propylbenzeneacetonitrile | 4-bromo-5-cyano-6-nitro-3-propylbenzeneacetonitrile |
| 4-chloro-3-cyano-5-isobutylbenzeneacetonitrile | 4-chloro-5-cyano-3-isobutyl-6-nitrobenzeneacetonitrile |
| 4-bromo-3-cyano-5-isobutylbenzeneacetonitrile | 4-bromo-5-cyano-3-isobutyl-6-nitrobenzeneacetonitrile |
| 3-cyano-4-fluoro-5-isobutylbenzeneacetonitrile | 5-cyano-4-fluoro-3-isobutyl-6-nitrobenzeneacetonitrile |
| 5-tert-butyl-4-chloro-3-cyanobenzeneacetonitrile | 3-tert-butyl-4-chloro-5-cyano-6-nitrobenzeneacetonitrile |
| 4-bromo-5-tert-butyl-3-cyanobenzeneacetonitrile | 4-bromo-3-tert-butyl-5-cyano-6-nitrobenzeneacetonitrile |

EXAMPLE 11

2-Bromo-1,4-diisopropylbenzene

To a one-liter flask containing 243 parts of p-diisopropylbenzene, 300 parts of carbon tetrachloride and 2.5 parts of iron powder is added dropwise 240 parts of bromine and sufficient carbon tetrachloride to make 180 parts of solution during seven hours at a temperature of −5°C. The solution is decanted from the residual ferric bromide and washed twice with 3N HCl. The carbon tetrachloride is removed under reduced pressure. A solution of 40 parts potassium hydroxide in two hundred parts of ethyl alcohol is added and refluxed 0.5 hr. The solution is poured into water, separated, washed with dilute hydrochloric acid, dilute sodium bisulfite solution and water, and dried. The solvent is removed and the 2-bromo-1,4-diisopropylbenzene distilled, bp 142°C at 25 mm, $n_D^{25}$ 1.5292.

By substituting the following alkylbenzenes for p-diisopropylbenzene, the following haloalkylbenzenes are made:

TABLE XIII

| Starting Material | Product |
| --- | --- |
| p-isobutylisopropylbenzene | 3-bromo-4-isobutylisopropylbenzene |
| m-isobutylisopropylbenzene | 4-bromo-3-isobutylisopropylbenzene |
| p-isobutylpropylbenzene | 2-bromo-4-isobutylpropylbenzene |
| p-sec-butylisobutylbenzene | 2-bromo-4-sec-butylisobutylbenzene |
| m-sec-butylisobutylbenzene | 1-bromo-4-sec-butyl-2-isobutylbenzene |
| p-ethylisobutylbenzene | 2-bromo-1-ethyl-4-isobutylbenzene |
| p-di-sec-butylbenzene | 2-bromo-1,4-di-sec-butylbenzene |
| m-di-sec-butylbenzene | 1-bromo-2,4-di-sec-butylbenzene |
| p-tert-butylisopropylbenzene | 2-bromo-4-butylisopropylbenzene |
| m-tert-butylisobutylbenzene | 1-bromo-4-tert-butyl-2-isobutylbenzene |
| m-diisopropylbenzene | 4-bromo-1,3-diisopropylbenzene |

TABLE XIII-continued

| Starting Material | Product |
| --- | --- |
| p-diisobutylbenzene | 2-bromo-1,4-diisobutylbenzene, b.p. 72°C at 0.1 mm |
| di-tert-butylbenzene | 1,4-di-tert-butyl-2-chlorobenzene |
| p-tert-butylethylbenzene | 2-bromo-4-tert-butylethylbenzene |
| p-sec-butylethylbenzene | 2-bromo-4-sec-butylethylbenzene |
| p-(1,2-dimethylpropyl)ethylbenzene | 2-bromo-4-(1,2-dimethylpropyl)ethylbenzene |
| p-(1,2-dimethylpropyl)propylbenzene | 2-bromo-4-(1,2-dimethylpropyl)propylbenzene |
| p-(1,2-dimethylpropyl)isobutylbenzene | 2-bromo-4-(1,2-dimethylpropyl)isobutylbenzene |
| p-tert-butylisobutylbenzene | 2-bromo-4-tert-butylisobutylbenzene |
| p-ethyl-tert-pentylbenzene | 2-bromo-1-ethyl-4-tert-pentylbenzene |
| 2-fluoro-1,4-diisobutylbenzene | 5-bromo-2-fluoro-1,4-diisobutylbenzene |
| 2-fluoro-1,5-diisopropylbenzene | 4-bromo-2-fluoro-1,5-1,5-diisopropylbenzene |
| 4-(1,2-dimethylpropyl)-1-ethyl-2-fluorobenzene | 5-bromo-4-(1,2-dimethylpropyl)-1-ethyl-2-fluorobenzene |
| 4-tert-butyltoluene | 2-bromo-4-tertbutyltoluene |
| m-ethyl-tert-pentylbenzene | 4-bromo-3-ethyl-tert-pentylbenzene |
| p-methyl-(1,1,2,2-tetramethylpropyl)benzene | 2-bromo-1-methyl-4-(1,1,2,2-tetramethylpropyl)benzene |
| p-ethyl-(1,1,2,2-tetramethylpropyl)benzene | 2-bromo-1-ethyl-4-(1,1,2,2-tetramethylpropyl)benzene |
| m-diethylbenzene | 2-bromo-1,3-diethylbenzene |
| m-diisobutylbenzene | 2-bromp-1,3-diisobutylbenzene |
| p-ethylneopentylbenzene | 3-bromo-4-ethylneopentylbenzene |

EXAMPLE 12

In a similar manner the following compounds are prepared:

TABLE XIV

| Starting Material | Product |
| --- | --- |
| 2,4-diisopropylaniline | 4-fluoro-1,3-diisopropylbenzene |
| 5-(1,2-dimethylpropyl)-2-ethylaniline | 4-(1,2-dimethylpropyl)-1-ethyl-2-fluorobenzene |
| 2,4-diisopropylaniline | 4-iodo-1,3-diisopropylbenzene |
| 2-ethyl-5-(1,1,2,2-tetramethyl)aniline | 1-ethyl-2-fluoro-4-(1,1,2,2-tetramethyl)benzene |
| 2,5-diisopropylaniline | 2-fluoro-1,4-diisopropylbenzene |
| 2-isobutyl-5-isopropylaniline | 2-fluoro-1-isobutyl-4-isopropylbenzene |
| 5-tert-butyl-2-isopropylaniline | 4-tert-butyl-2-fluoro-1-isopropylbenzene |

2-Fluoro-1,4-diisobutylbenzene - (Org. React. Vol V, p 203)

To 124 parts of 6N hydrochloric acid is added 48.8 parts of 2,5-diisobutylaniline. The mixture is cooled to 0° and a cold solution of 17.3 parts of sodium nitrite in water is added slowly, keeping temp. at 0°. A cold solution of 35 parts of ammonium fluoroborate in 120 parts of water is added with vigorous stirring. After one half hour, the precipitate is collected, washed with 25 parts cold 5% ammonium fluoroborate solution, 30 parts cold methanol and ether. The 2,5-diisobutylbenzenediazonium fluoroborate is air dried. The salt is placed in a flask with tube connecting to a second cooled flask and heated until decomposition begins. Sufficient heat to maintain gentle decomposition is continued. When decomposition is complete, the 2-fluoro-1,4-diisobutylbenzene is taken up in ether, washed with dilute sodium hydroxide and water and dried. Removal of the ether gives 2-fluoro-1,4-diisobutylbenzene which can be purified by distillation under reduced pressure.

EXAMPLE 13

4-Bromo-2,5-diisopropylbenzyl Chloride

In a flask is placed 36 parts of 2-bromo-1,4-diisopropylbenzene, 30 parts of paraformaldehyde and 20 parts of zinc chloride. A stream of dry hydrogen chloride is passed in with stirring, and the temperature rises to 65°C. The temperature is maintained at 65°C for 3 hours and is increased to 70°C. Additional amounts of 15 parts of paraformaldehyde and 15 parts of zinc chloride are added, and the reaction is continued at 75° for a total time of 6.5 hrs. The mixture is cooled and washed with hydrochloric acid, dilute sodium bicarbonate, and water. After drying, the 4-bromo-2,5-diisopropylbenzyl chloride is distilled, bp 91°–93°C at 0.5 mm.

By substituting the following haloalkylbenzenes for 2-bromo-1,4-diisopropylbenzene, the following haloalkylbenzyl halides are made.

TABLE XV

| Starting Material | Product |
| --- | --- |
| 3-bromo-4-isobutylisopropylbenzene | 4-bromo-5-isobutyl-2-isopropylbenzyl chloride |
| 3-bromo-4-isobutylisopropylbenzene | 3-bromo-2-isobutyl-5-isopropylbenzyl chloride |
| 2-bromo-4-isobutylpropylbenzene | 4-bromo-2-isobutyl-5-propylbenzyl chloride |
| 2-bromo-4-sec-butylisobutylbenzene | 4-bromo-2-sec-butyl-5-isobutylbenzyl chloride |
| 1-bromo-4-sec-butyl-2-isobutylbenzene | 5-bromo-2-sec-butyl-4-isobutylbenzyl chloride |
| 2-bromo-1-ethyl-4-isobutylbenzene | 4-bromo-5-ethyl-2-isobutylbenzyl chloride |
| 2-bromo-1,4-di-sec-butylbenzene | 4-bromo-2,5-di-sec-butylbenzyl chloride |
| 1-bromo-2,4-di-sec-butylbenzene | 5-bromo-2,4-di-sec-butylbenzyl chloride |
| 2-bromo-4-tert-butylisopropylbenzene | 4-bromo-2-tert-butyl-5-isopropylbenzyl chloride |
| 4-tert-butyl-2-chloroisopropylbenzene | 2-tert-butyl-4-chloro-5-isopropylbenzyl bromide |
| 4-bromo-1,3-diisopropylbenzene | 5-bromo-2,4-diisopropylbenzyl chloride |
| 2-bromo-1,4-diisobutylbenzene | 4-bromo-2,5-diisobutylbenzyl chloride, b.p. 107–110°C at 0.1 mm |
| 5-bromo-2-fluoro-1,4-diisobutylbenzene | 5-bromo-2-fluoro-3,6-diisobutylbenzyl chloride |
| 4-bromo-2-fluoro-1,5-diisopropylbenzene | 5-bromo-3-fluoro-2,6-diisopropylbenzyl chloride |
| 5-bromo-4-(1,2-dimethylpropyl)-1-ethyl-4-fluorobenzene | 5-bromo-6-(1,2-dimethyllpropyl)-3-ethyl-2-fluorobenzyl chloride |

TABLE XV-continued

| Starting Material | Product |
| --- | --- |
| 2-bromo-4-tert-butyltoluene | 3-bromo-5-tert-butyl-2-methylbenzyl chloride |
| 4-bromo-3-ethyl-tert-pentylbenzene | 5-bromo-4-ethyl-2-tert-pentylbenzyl chloride |

In some cases, chloromethylation of the bromoalkylbenzenes gives mixtures of isomers. These may be separated by careful distillation or by chromatography, but usually the mixture is used in subsequent reaction. The following compounds give the indicated mixtures when chloromethylated:

removed and the 2,4-dibromo-3,6-diisobutylbenzene is obtained.

By replacing the 2,5-diisobutylbenzyl chloride with the following benzyl chlorides, the following products are obtained:

TABLE XVII

| Starting Material | Product |
| --- | --- |
| 2,5-dipropylbenzyl chloride | 2,4-dibromo-3,6-dipropylbenzyl chloride |
| 2-isobutyl-5-isopropylbenzyl chloride | 2,4-dibromo-6-isobutyl-3-isopropylbenzyl chloride |
| 2,5-diisopropylbenzyl chloride | 2,4-dibromo-3,6-diisopropylbenzyl chloride |
| 2,5-di-tert-butylbenzyl chloride | 2,4-dibromo-3,6-di-tert-butylbenzyl chloride |
| 2,5-di-sec-butylbenzyl chloride | 2,4-dibromo-3,6-di-sec-butylbenzyl chloride |

TABLE XVI

| Starting Material | Product |
| --- | --- |
| 2-bromo-1,4-di-tert-butylbenzene | 3-bromo-2,5-di-tert-butylbenzyl chloride |
| | 4-bromo-2,5-di-tert-butylbenzyl chloride |
| 2-bromo-4-tert-butylethylbenzene | 3-bromo-5-tert-butyl-2-ethylbenzyl chloride |
| | 4-bromo-2-tert-butyl-5-ethylbenzyl chloride, b.p. 92°C/0.05 mm |
| 2-bromo-4-sec-butylethylbenzene | 3-bromo-5-sec-butyl-2-ethylbenzyl chloride. |
| | 4-bromo-2-sec-butyl-5-ethylbenzyl chloride |
| 2-bromo-4-(1,2-dimethylpropyl)ethylbenzene | 3-bromo-5-(1,2-dimethylpropyl)-2-ethylbenzyl chloride |
| | 4-bromo-2-(1,2-dimethylpropyl)-5-ethylbenzyl chloride |
| 2-bromo-4-(1,2-dimethylpropyl)propylbenzene | 3-bromo-5-(1,2-dimethylpropyl)-2-propylbenzyl chloride |
| | 4-bromo-2-(1,2-dimethylproply)-5-propylbenzyl chloride |
| 2-bromo-4-(1,2-dimethylpropyl)isobutylbenzene | 3-bromo-5-(1,2-dimethylpropyl)-2-isobutylbenzyl chloride |
| | 4-bromo-2-(1,2-dimethylpropyl)-5-isobutylbenzyl chloride |
| 2-bromo-4-tert-butylisobutylbenzene | 3-bromo-5-tert-butyl-2-isobutylbenzyl chloride |
| | 4-bromo-2-tert-butyl-5-isobutylbenzyl chloride |
| 2-bromo-1-ethyl-4-tert-pentylbenzene | 3-bromo-2-ethyl-5-tert-pentylbenzyl chloride |
| | 4-bromo-5-ethyl-2-tert-pentylbenzyl chloride |
| 2-bromo-1-methyl-4-(1,1,2,2-tetramethylpropyl)-benzene | 3-bromo-2-methyl-5-(1,1,2,2-tetramethylpropyl)benzyl chloride |
| | 4-bromo-5-methyl-2-(1,1,2,2-tetramethylpropyl)benzyl chloride |
| 2-bromo-1-ethyl-4-(1-ethyl-1-methylpropyl)-benzene | 3-bromo-2-ethyl-5-(1-ethyl-1-methylpropyl)benzyl chloride |
| | 4-bromo-5-ethyl-2-(1-ethyl-1-methylpropyl)benzyl chloride |
| 3-bromo-4-ethylneopentylbenzene | 3-bromo-2-ethyl-5-neopentylbenzyl chloride |
| | 4-bromo-5-ethyl-2-neopentylbenzyl chloride |
| 2-bromo-1,3-diethylbenzene | 3-bromo-2,4-diethylbenzyl chloride |
| | 4-bromo-3,5-diethylbenzyl chloride |
| 2-bromo-1,3-diisobutylbenzene | 3-bromo-2,4-diisobutylbenzyl chloride |
| | 4-bromo-3,5-diisobutylbenzyl chloride |

EXAMPLE 14

2,4-Dibromo-3,6-diisobutylbenzyl Chloride

To a solution of 23.8 parts of 2,5-diisobutylbenzyl chloride in 50 parts of carbon tetrachloride there is added 1.0 part of iron powder. The mixture is cooled to 0°, and a solution of 32 parts of bromine in 30 parts of carbon tetrachloride is added dropwise during 7 hours at 0°. The resulting solution is washed with dilute hydrochloric acid, dilute sodium bicarbonate solution, dilute sodium bisulfite solution, and water. After drying with magnesium sulfate, the carbon tetrachloride is

EXAMPLE 15

4-Bromo-2-chloro-3,6-diisopropylbenzyl Chloride

To a solution of 29 parts of 4-bromo-2,5-diisopropylbenzyl chloride in 50 parts of carbon tetrachloride there is added 1.0 part of iron powder. To the mixture, cooled to 0° and stirred, there is added 7.8 parts of chlorine during 2 hr. Stirring is continued for 2 hours; the solution is washed with dilute hydrochloric acid, sodium bicarbonate solution, and water. After drying, the carbon tetrachloride is removed, and the 4-bromo-2-chloro-3,6-diisopropylbenzyl chloride is recovered.

By replacing the 4-brommo-2,5-diisopropylbenzyl chloride with the following benzyl chlorides, these -bromo-are obtained:

TABLE XVIII

| Starting Material | Product |
| --- | --- |
| 4-bromo-2-ethyl-5-isobutylbenzyl chloride | 4-bromo-2-chloro-6-ethyl-3-isobutylbenzyl chloride |
| 4-bromo-5-(1,2-dimethylpropyl)-2-propylbenzyl | 4-bromo-2-chloro-3-(1,2-dimethylpropyl)-6-propyl- |

TABLE XVIII-continued

| Starting Material | Product |
|---|---|
| chloride | benzyl chloride |
| 3-iodo-2,6-diisopropyl-4-methylbenzyl chloride | 3,5-diiodo-2,6-diisopropyl-4-methylbenzyl chloride |
| 4-bromo-2-isopropyl-5-(1,1,2,2-tetramethylpropyl)-benzyl chloride | 4-bromo-2-chloro-6-isopropyl-3-(1,1,2,2-tetramethylpropyl)benzyl chloride |
| 4-bromo-5-isobutyl-2-isopropylbenzyl chloride | 4-bromo-2-chloro-3-isobutyl-6-isopropylbenzyl chloride |
| 3-bromo-2,6-di-tert-butyl-4-methylbenzyl chloride | 3-bromo-2,6-di-tert-butyl-5-chloro-4-methylbenzyl chloride |

For unsymmetrical alkylbenzenes, a different isomer is obtained if one first chloromethylates and then brominates.

Using the indicated starting alkylbenzenes in the same molar amounts as in Example 16, the following compounds are prepared:

TABLE XIX

| Starting Material | Product |
|---|---|
| m-isobutylisopropylbenzene | 2-isobutyl-4-isopropylbenzyl chloride |
| p-isobutylpropylbenzene | 5-isobutyl-2-propylbenzyl chloride |
| m-isobutylpropylbenzene | 4-isobutyl-2-propylbenzyl chloride |
| p-sec-butylisobutylbenzene | 5-sec-butyl-2-isobutylbenzyl chloride |
| m-sec-butylisobutylbenzene | 4-sec-butyl-2-isobutylbenzyl chloride |
| p-ethylisobutylbenzene | 2-ethyl-5-isobutylbenzyl chloride |
| p-tert-butylcumene | 5-tert-butyl-2-isopropylbenzyl chloride |
| m-tert-butylcumene | 4-tert-butyl-2-isopropylbenzyl chloride |
| p-tert-butylethylbenzene | 5-tert-butyl-2-ethylbenzyl chloride |
| p-sec-butylethylbenzene | 5-sec-butyl-2-ethylbenzyl chloride |
| p-(1,2-dimethylpropyl)ethylbenzene | 5-(1,2-dimethylpropyl)-2-ethylbenzyl chloride |
| p-(1,2-dimethylpropyl)propylbenzene | 5-(1,2-dimethylpropyl)-2-propylbenzyl chloride |
| p-(1,2-dimethylpropyl)isobutylbenzene | 5-(1,2-dimethylpropyl)-2-isobutylbenzyl chloride |
| p-tert-butylisobutylbenzene | 5-tert-butyl-2-isobutylbenzyl chloride |
| p-ethyl-tert-pentylbenzene | 2-ethyl-5-tert-pentylbenzyl chloride |
| m-diethylbenzene | 2,4-diethylbenzyl chloride |
| m-diisobutylbenzene | 2,4-diisobutylbenzyl chloride |
| m-dipropylbenzene | 2,6-dipropylbenzyl chloride |
| m-diisobutylbenzene | 2,6-diisobutylbenzyl chloride |
| p-ethyl-(1,1,2-trimethylpropyl)benzene | 2-ethyl-5-(1,1,2-trimethylpropyl)benzyl chloride |
| p-propyl-(1,1,2,2-tetramethylpropyl)benzene | 2-propyl-5-(1,1,2,2-tetramethylpropyl)benzyl chloride |
| p-(1,1,2-trimethylpropyl)toluene | 2-methyl-4-(1,1,2-trimethylpropyl)benzyl chloride |

EXAMPLE 16

2-Isobutyl-5-isopropylbenzyl Chloride

In a flask there are placed 176 parts of p-isopropylisobutylbenzene, 15 parts of paraformaldehyde, and 15 parts of zinc chloride. A stream of hydrogen chloride is passed into the mixture, and the temperature is increased to 65°C. After the mixture is saturated with hydrogen chloride, stirring is continued at 70°–75°C for 3 hours. The mixture is cooled and washed with hydrochloric acid, sodium bicarbonate solution, and water. After drying, the product is distilled. The first fraction is the unchanged starting material; the higher boiling material, 75°–80°C at 0.05 mm, is the desired 2-isobutyl-5-isopropylbenzyl chloride.

EXAMPLE 17

4-Bromo-2-isobutyl-5-isopropylbenzyl Chloride

In a flask are placed 225 parts of 2-isobutyl-5-isopropylbenzyl chloride, 300 parts of carbon tetrachloride and 2.5 parts of iron powder. Bromine (160 parts) in 100 parts of carbon tetrachloride is added dropwise during 7 hr. The solution is washed twice with hydrochloric acid then with sodium bicarbonate solution, dilute sodium bisulfite solution, and water. The solution is dried, the carbon tetrachloride removed, and the 4-bromo-2-isobutyl-5-isopropylbenzyl chloride distilled under reduced pressure.

In a similar manner, using the designated benzyl chlorides, the following compounds are made:

TABLE XX

| Starting Material | Product |
|---|---|
| 2-isobutyl-4-isopropylbenzyl chloride | 5-bromo-2-isobutyl-4-isopropylbenzyl chloride |
| 5-isobutyl-2-propylbenzyl chloride | 4-bromo-5-isobutyl-2-propylbenzyl chloride |
| 4-isobutyl-2-propylbenzyl chloride | 5-bromo-4-isobutyl-2-propylbenzyl chloride |
| 5-sec-butyl-2-isobutylbenzyl chloride | 4-bromo-5-sec-butyl-2-isobutylbenzyl chloride |
| 4-sec-butyl-2-isobutylbenzyl chloride | 5-bromo-4-sec-butyl-2-isobutylbenzyl chloride |
| 2-ethyl-5-isobutylbenzyl chloride | 4-bromo-2-ethyl-5-isobutylbenzyl chloride |
| 5-tert-butyl-2-isopropylbenzyl chloride | 4-bromo-5-tert-butyl-2-isopropylbenzyl chloride |
| 4-tert-butyl-2-isopropylbenzyl chloride | 6-bromo-4-tert-butyl-2-isopropylbenzyl chloride |
| 2,4-diisopropylbenzyl chloride | 5-chloro-2,4-diisopropylbenzyl chloride |
| 2,4-diisopropylbenzyl chloride | 5-iodo-2,4-diisopropylbenzyl chloride |
| 2-ethyl-5-(1,1,2-trimethylpropyl)benzyl chloride | 4-bromo-2-ethyl-5-(1,1,2-trimethylpropyl)benzyl chloride |
| 2-propyl-5-(1,1,2,2-tetramethylpropyl)benzyl chloride | 4-bromo-2-propyl-5-(1,1,2,2-tetramthylpropyl)-benzyl chloride |
| 2-methyl-4-(1,1,2-trimethylpropyl)benzyl chloride | 5-bromo-2-methyl-4-(1,1,2-trimethylpropyl)benzyl chloride |

In some cases, bromination of the alkylbenzylchlorides gives mixtures of isomers which can be separated by careful distillation or chromatography, but usually the mixture is adequate for the intended purpose. The following compounds give the indicated mixtures when brominated:

ylation of the following monohalo- or dihalodialkylphenols gives the corresponding chloromethyl derivatives.

TABLE XXII

| Starting Materials | Product |
| --- | --- |
| 2,4-dichloro-3,6-diisopropylphenol | 2,4-dichloro-5-chloromethyl-3,6-diisopropylphenol |
| 2,3-dichloro-4,6-diisopropylphenol | 2,3-dichloro-5-chloromethyl-4,6-diisopropylphenol |
| 2,6-dichloro-3,5-diisopropylphenol | 2,6-dichloro-4-chloromethyl-3,5-diisopropylphenol |
| 4,5-dichloro-2,6-diisopropylphenol | 4,5-dichloro-3-chloromethyl-2,6-diisopropylphenol |
| 2-chloro-3,5-diisopropylphenol | 2-chloro-4-chloromethyl-3,5-diisopropylphenol |
| 2-chloro-3,6-diisopropylphenol | 2-chloro-4-chloromethyl-3,6-diisopropylphenol |
| 2-chloro-4,6-diisopropylphenol | 2-chloro-3-chloromethyl-4,6-diisopropylphenol |
| 2-bromo-3,6-diisopropylphenol | 2-bromo-4-chloromethyl-3,6-diisopropylphenol |
| 4-bromo-3,6-diisopropylphenol | 4-bromo-2-chloromethyl-3,6-diisopropylphenol |
| 4-chloro-2,6-diisopropylphenol | 4-chloro-3-chloromethyl-2,6-diisopropylphenol |
| 3-tert-butyl-2,6-dichloro-5-isopropylphenol | 3-tert-butyl-2,6-dichloro-4-chloromethyl-5-isopropylphenol |
| 3-sec-butyl-2,6-dichloro-5-isopropylphenol | 3-sec-butyl-2,6-dichloro-4-chloromethyl-5-isopropylphenol |
| 2,6-dibromo-3-isobutyl-5-isopropylphenol | 2,6-dibromo-3-isobutyl-4-chloromethyl-5-isopropylphenol |
| 3,5-di-sec-butyl-2,6-dichlorophenol | 3,5-di-sec-butyl-2,6-dichloro-4-chloromethylphenol |
| 2,6-dichloro-3,5-diisobutylphenol | 2,6-dichloro-4-chloromethyl-3,5-diisobutylphenol |
| 5-tert-butyl-2,6-dichloro-3-isobutylphenol | 5-tert-butyl-2,6-dichloro-4-chloromethyl-3-isobutylphenol |
| 3,5-di-tert-butyl-2,6-dichlorophenol | 3,5-di-tert-butyl-2,6-dichloro-4-chloromethylphenol |
| 3-tert-butyl-2,6-dichloro-5-ethylphenol | 3-tert-butyl-2,6-dichloro-4-chloromethyl-5-ethylphenol |

TABLE XXI

| Starting Material | Product |
| --- | --- |
| 5-tert-butyl-2-ethylbenzyl chloride | 4-bromo-5-tert-butyl-2-ethylbenzyl chloride |
| | 3-bromo-5-tert-butyl-2-ethylbenzyl chloride |
| 5-sec-butyl-2-ethylbenzyl chloride | 4-bromo-5-sec-butyl-2-ethylbenzyl chloride |
| | 3-bromo-5-sec-butyl-2-ethylbenzyl chloride |
| 5-(1,2-dimethylpropyl)-2-ethylbenzyl chloride | 4-bromo-5-(1,2-dimethylpropyl)-2-ethylbenzyl chloride |
| | 3-bromo-5-(1,2-dimethylpropyl)-2-ethylbenzyl chloride |
| 5-(1,2-dimethylpropyl)-2-propylbenzyl chloride | 4-bromo-5-(1,2-dimethylpropyl)-2-propylbenzyl chloride |
| | 3-bromo-5-(1,2-dimethylpropyl)-2-propylbenzyl chloride |
| 5-(1,2-dimethylpropyl)-2-isobutylbenzyl chloride | 4-bromo-5-(1,2-dimethylpropyl)-2-isobutylbenzyl chloride |
| | 3-bromo-5-(1,2-dimethylpropyl)-2-isobutylbenzyl chloride |
| 5-tert-butyl-2-isobutylbenzyl chloride | 4-bromo-5-tert-butyl-2-isobutylbenzyl chloride |
| | 3-bromo-5-tert-butyl-2-isobutylbenzyl chloride |
| 2-ethyl-5-tert-pentylbenzyl chloride | 4-bromo-2-ethyl-5-tert-pentylbenzyl chloride |
| | 3-bromo-2-ethyl-5-tert-pentylbenzyl chloride |
| 2,4-diethylbenzyl chloride | 5-bromo-2,4-diethylbenzyl chloride |
| | 3-bromo-2,4-diethylbenzyl chloride |
| 2,4-diisobutylbenzyl chloride | 5-bromo-2,4-diisobutylbenzyl chloride |
| | 3-bromo-2,4-diisobutylbenzyl chloride |
| 4-isobutyl-2-propylbenzyl chloride | 5-bromo-4-isobutyl-2-propylbenzyl chloride |
| | 3-bromo-4-isobutyl-2-propylbenzyl chloride |
| 2,6-dipropylbenzyl chloride | 3-bromo-2,6-dipropylbenzyl chloride |
| | 4-bromo-2,6-dipropylbenzyl chloride |
| 2,6-diisobutylbenzyl chloride | 3-bromo-2,6-diisobutylbenzyl chloride |
| | 4-bromo-2,6-diisobutylbenzyl chloride |

EXAMPLE 18

2,6-Dibromo-4-chloromethyl-3,5-diisopropylphenol

Three hundred thirty-six parts of 2,6-dibromo-3,5-diisopropylphenol [prepared as described in Canad, J. Chem., Vol. 41, p. 1653 (1963)] is allowed to react with 130 parts of chloromethyl methyl ether and 80 parts of stannic chloride in 400 parts of carbon disulfide under general conditions set forth in "Organic Reactions", Vol. 1, p. 68 and 69. The reaction mixture is poured on ice, and the organic layer is separated and dried over anhydrous calcium sulfate. The solvent is allowed to evaporate and the residue is crystallized to give a pure sample of the title compound. Chloromethylation of the following monohalo- or dihalodialkylphenols gives the corresponding chloromethyl derivatives.

EXAMPLE 19

5-Bromo-2-chloromethyl-3,6-diisopropylhydroquinone

Two hundred seventy-three parts of 3-bromo-2,5-diisopropylhydroquinone is allowed to react with 130 parts of chloromethylmethyl ether and 80 parts of stannic chloride in 400 parts of carbon disulfide under general conditions set forth in "Organic Reactions", Vol. 1, p. 68 and 69. The reaction mixture is poured on ice, and the organic layer is separated and dried over anhydrous calcium sulfate. The solvent is allowed to evaporate and the residue is crystallized to give a pure sample of the title compound. Chloromethylation of the following monohalo- or dihalodialkylhydroquinones or resorcinols gives the corresponding chloromethyl derivatives.

TABLE XXIII

| Starting Material | Product |
| --- | --- |
| 2-bromo-3,5-diisopropylhydroquinone | 2-bromo-6-chloromethyl-3,5-diisopropylhydroquinone |
| 5-bromo-4,6-diisopropylresorcinol | 5-bromo-4,6-chloromethyl-4,6-diisopropylresorcinol |
| 3-bromo-5-tert-butyl-2-isopropylhydroquinone | 3-bromo-5-tert-butyl-6-dibromomethyl-2-isopropylhydroquinone |
| 3-bromo-5-sec-butyl-2-isopropylhydroquinone | 3-bromo-5-sec-butyl-6-chloromethyl-2-isopropylhydroquinone |
| 3-bromo-2-isobutyl-5-isopropylhydroquinone | 3-bromo-6-chloromethyl-2-isobutyl-5-isopropylhydroquinone |
| 3-bromo-2,5-di-sec-butylhydroquinone | 3-bromo-2,5-di-sec-butyl-6-chloromethylhydroquinone |
| 3-bromo-2,5-diisobutylhydroquinone | 3-bromo-6-chloromethyl-2,5-diisobutylhydroquinone |
| 3-bromo-2,5-di-tert-butylhydroquinone | 3-bromo-2,5-di-tert-butyl-6-chloromethylhydroquinone |
| 3-bromo-5-tert-butyl-2-isobutylhydroquinone | 3-bromo-5-tert-butyl-6-chloromethyl-2-isobutylhydroquinone |
| 3-bromo-5-tert-butyl-2-ethylhydroquinone | 3-bromo-5-tert-butyl-6-chloromethyl-2-ethylhydroquinone |

EXAMPLE 20

1-Bromo-2,6-diisopropylbenzene

A solution of 262 parts of triphenylphosphine in 750 parts of acetonitrile is brominated with 160 parts of bromine at room temperature. The solvent is evaporated, and to the residue is added 178 parts of 2,6-diisopropylphenol. The mixture is heated at 200°C as described in J. Am. Chem. Soc. 86, 464 (1964). The product is distilled under reduced pressure and then fractionated at 0.1 mm Hg.

The following compounds are made by appropriate substitution in the above procedure.

EXAMPLE 21

3-Bromo-2,5-dichloro-4,6-diisopropylbenzyl Chloride

A solution of 404 parts of tri-n-butylphosphine in 1200 parts of acetonitrile is chlorinated with 142 parts of chlorine at room temperature. The solvent is evaporated and to the residue is added 321.5 parts of 2-bromo-6-chloromethyl-3,5-diisopropylhydroquinone. The mixture is heated at 200°C as described in J. Am. Chem. Soc., 86, 464 (1964). The product is distilled under reduced pressure and then fractionated at 0.1 mm Hg.

The following compounds are made by appropriate substitution in the above procedure.

TABLE XXIV

| Starting Material | Product |
| --- | --- |
| 2,6-diisopropylphenol | 1-chloro-2,6-diisopropylbenzene |
| 2,4-dichloro-5-chloromethyl-3,6-diisopropylphenol | 5-bromo-2,4-dichloro-3,6-diisopropylbenzyl chloride |
| 2,3-dichloro-5-chloromethyl-4,6-diisopropylphenol | 5-bromo-3,4-dichloro-2,6-diisopropylbenzyl chloride |
| 2,6-dichloro-4-chloromethyl-3,5-diisopropylphenol | 4-bromo-3,5-dichloro-2,6-diisopropylbenzyl chloride |
| 4,5-dichloro-3-chloromethyl-2,6-diisopropylphenol | 5-bromo-2,3-dichloro-4,6-diisopropylbenzyl chloride |
| 2-chloro-4-chloromethyl-3,5-diisopropylphenol | 4-bromo-3-chloro-2,6-diisopropylbenzyl chloride |
| 2-chloro-4-chloromethyl-3,6-diisopropylphenol | 4-bromo-3-chloro-3,6-diisopropylbenzyl chloride |
| 2-chloro-3-chloromethyl-4,6-diisopropylphenol | 3-bromo-2-chloro-4,6-diisopropylbenzyl chloride |
| 2-bromo-4-chloromethyl-3,6-diisopropylphenol | 3-bromo-4-chloro-2,5-diisopropylbenzyl chloride |
| 4-bromo-2-chloromethyl-3,6-diisopropylphenol | 5-bromo-2-chloro-3,6-diisopropylbenzyl chloride |
| 4-chloro-3-chloromethyl-2,6-diisopropylphenol | 5-bromo-2-chloro-3,6-diisopropylbenzyl chloride |
| 3-tert-butyl-2,6-dichloro-4-chloromethyl-5-isopropylphenol | 4-bromo-2-tert-butyl-3,5-dichloro-6-isopropylbenzyl chloride |
| 3-sec-butyl-2,6-dichloro-4-chloromethyl-5-isopropylphenol | 4-bromo-2-sec-butyl-3,5-dichloro-6-isopropylbenzyl chloride |
| 2,6-dibromo-3-isobutyl-4-chloromethyl-5-isopropylphenol | 3,4,5-tribromo-2-isobutyl-6-isopropylbenzyl chloride |
| 3,5-di-sec-butyl-2,6-dichloro-4-chloromethylphenol | 4-bromo-2,6-di-sec-butyl-3,5-dichlorobenzyl chloride |
| 2,6-dichloro-4-chloromethyl-3,5-diisobutylphenol | 4-bromo-3,5-dichloro-2,6-diisobutylbenzyl chloride |
| 5-tert-butyl-2,6-dichloro-4-chloromethyl-3-isobutylphenol | 4-bromo-2-tert-butyl-3,5-dichloro-6-isobutylbenzyl chloride |
| 3,5-di-tert-butyl-2,6-dichloro-4-chloromethylphenol | 4-bromo-2,6-di-tert-butyl-3,5-dichlorobenzyl chloride |
| 3-tert-butyl-2,6-dichloro-4-chloromethyl-5-ethylphenol | 4-bromo-2-tert-butyl-3,5-dichloro-6-ethylbenzyl chloride |

TABLE XXV

| Starting Material | Product |
| --- | --- |
| 5-bromo-2-chloromethyl-3,6-diisopropylhydroquinone | 4-bromo-2,5-dichloro-3,6-diisopropylbenzyl chloride |
| 5-bromo-2-chloromethyl-4,6-diisopropylresorcinol | 4-bromo-2,6-dichloro-3,5-diisopropylbenzyl chloride |
| 5-bromo-3-tert-butyl-2-chloromethyl-6-isopropylhydroquinone | 4-bromo-3-tert-butyl-2,5-dichloro-6-isopropylbenzyl chloride |
| 5-bromo-3-sec-butyl-2-chloromethyl-6-isopropylhydroquinone | 4-bromo-3-sec-butyl-2,5-dichloro-6-isopropylbenzyl chloride |
| 5-bromo-2-chloromethyl-3-isobutyl-6-isopropylhydroquinone | 4-bromo-2,5-dichloro-3-isobutyl-6-isopropylbenzyl chloride |
| 5-bromo-3,6-di-sec-butyl-2-chloromethylhydroquinone | 4-bromo-3,6-di-sec-butyl-2,5-dichlorobenzyl chloride |
| 5-bromo-2-chloromethyl-3,6-diisobutylhydroquinone | 4-bromo-2,5-dichloro-3,6-diisobutylbenzyl chloride |
| 5-bromo-3-tert-butyl-2-chloromethyl-6-isobutylhydroquinone | 4-bromo-3-tert-butyl-2,5-dichloro-6-isobutylbenzyl chloride |

TABLE XXV-continued

| Starting Material | Product |
| --- | --- |
| 5-bromo-3-tert-butyl-2-chloromethyl-6-ethylhydroquinone | 4-bromo-3-tert-butyl-2,5-dichloro-6-ethylbenzyl chloride |

EXAMPLE 22

4-Cyano-2,5-diisopropylbenzeneacetonitrile

In a flask equipped with a mechanical stirrer and reflux condenser is placed 29 parts of 4-bromo-2,5-diisopropylbenzyl chloride and 50 parts of N-methylpyrrolidone. Cuprous cyanide (22 parts) is added with good stirring, and the flask is rapidly heated to 200°C and kept at 205°–210° for 20 min. The flask is cooled, the contents transferred to a beaker, and ice and water are added. The mixture is stirred in a Waring blender, collected on a filter and washed with cold water. The thick paste is suspended in water, and 100 parts of methylene chloride is added. Eleven grams of chlorine is slowly passed in under the surface at 15°C; the methylene chloride solution is separated, washed twice with dilute hydrochloric acid, then with 5% sodium bicarbonate solution, and with water. The solution is dried, filtered and evaporated. The residue is recrystallized from an ether-pentane mixture at −20° to yield 9.6 parts of the product, mp 88°–89°C.

The following compounds are made by appropriate substitution in the above procedure.

TABLE XXVI

| Starting Material | Product |
| --- | --- |
| 4-bromo-2,5-di-sec-butylbenzyl chloride | 2,5-di-sec-butyl-4-cyanobenzeneacetonitrile |
| 4-bromo-5-isobutyl-2-isopropylbenzyl chloride | 4-cyano-5-isobutyl-2-isopropylbenzeneacetonitrile |
| 5-bromo-4-isobutyl-2-isopropylbenzyl chloride | 5-cyano-4-isobutyl-2-isopropylbenzeneacetonitrile |
| 4-bromo-2-isobutyl-5-propylbenzyl chloride | 4-cyano-2-isobutyl-5-propylbenzeneacetonitrile |
| 4-bromo-2-sec-butyl-5-isobutylbenzyl chloride | 2-sec-butyl-4-cyano-5-isobutylbenzeneacetonitrile |
| 5-bromo-2-sec-butyl-4-isobutylbenzyl chloride | 2-sec-butyl-5-cyano-4-isobutylbenzeneacetonitrile |
| 4-bromo-5-ethyl-2-isobutylbenzyl chloride | 4-cyano-5-ethyl-2-isobutylbenzeneacetonitrile |
| 4-bromo-2,5-di-sec-butylbenzyl chloride | 2,5-di-sec-butyl-4-cyanobenzeneacetonitrile |
| 5-bromo-2-tert-butyl-4-isobutylbenzyl chloride | 2-tert-butyl-5-cyano-4-isobutylbenzeneacetonitrile |
| 5-bromo-2,4-diisopropylbenzyl chloride | 5-cyano-2,4-diisopropylbenzeneacetonitrile |
| 4-bromo-2,5-diisobutylbenzyl chloride | 4-cyano-2,5-diisobutylbenzeneacetonitrile, b.p. 140–147°C/O. 1mm |
| 5-bromo-2-isobutyl-4-isopropylbenzyl chloride | 5-cyano-2-isobutyl-4-isopropylbenzeneacetonitrile |
| 4-bromo-5-isobutyl-2-propylbenzyl chloride | 4-cyano-5-isobutyl-2-propylbenzeneacetonitrile |
| 5-bromo-4-isobutyl-2-propylbenzyl chloride | 5-cyano-4-isobutyl-2-propylbenzeneacetonitrile |
| 4-bromo-5-sec-butyl-2-isobutylbenzyl chloride | 5-sec-butyl-4-cyano-2-isobutylbenzeneacetonitrile |
| 5-bromo-4-sec-butyl-2-isobutylbenzyl chloride | 4-sec-butyl-5-cyano-2-isobutylbenzeneacetonitrile |
| 4-bromo-2-ethyl-5-isobutylbenzyl chloride | 4-cyano-2-ethyl-5-isobutylbenzeneacetonitrile |
| 4-bromo-5-tert-butyl-2-isopropylbenzyl chloride | 5-tert-butyl-4-cyano-2-isopropylbenzeneacetonitrile |
| 5-bromo-4-tert-butyl-2-isopropylbenzyl chloride | 4-tert-butyl-5-cyano-2-isopropylbenzeneacetonitrile |
| 5-bromo-2-fluoro-3,6-diisobutylbenzyl chloride | 5-cyano-2-fluoro-3,6-diisobutylbenzeneacetonitrile |
| 5-bromo-3-fluoro-2,6-diisopropylbenzyl chloride | 5-cyano-3-fluoro-2,6-diisopropylbenzeneacetonitrile |
| 5-bromo-6-(1,2-dimethylpropyl)-3-ethyl-2-fluorobenzyl chloride | 5-cyano-6-(1,2-dimethylpropyl)-3-ethyl-2-fluorobenzeneacetonitrile |
| 3-bromo-5-tert-butyl-2-methylbenzyl chloride | 5-tert-butyl-3-cyano-2-methylbenzeneacetonitrile |
| 4-bromo-2-ethyl-5-(1,1,2-trimethylpropyl)benzyl chloride | 4-cyano-2-ethyl-5-(1,1,2-trimethylpropyl)benzeneacetonitrile |
| 4-bromo-2-propyl-5-(1,1,2,2-tetramethylpropyl)-benzyl chloride | 4-cyano-2-propyl-5-(1,1,2,2-tetramethylpropyl)-benzeneacetonitrile |
| 5-bromo-4-ethyl-2-tert-pentylbenzyl chloride | 5-cyano-4-ethyl-2-tert-pentylbenzeneacetonitrile |
| 5-bromo-2-methyl-4-(1,1,2-trimethylpropyl)benzyl chloride | 5-cyano-2-methyl-4-(1,1,2-trimethylpropyl)benzeneacetonitrile |
| 3-bromo-5-tert-butyl-2-ethylbenzyl chloride | 5-tert-butyl-3-cyano-2-ethylbenzeneacetonitrile, m.p. 135–137°C |

The procedure for the preparation of Example 22 is used to prepare the following compounds, but exactly 2 moles of cuprous cyanide are used per mole of the benzyl chloride.

TABLE XXVII

| Starting Material | Product |
| --- | --- |
| 2,4-dibromo-3,6-dipropylbenzyl chloride | 2-bromo-4-cyano-3,6-dipropylbenzeneacetonitrile |
| 2,4-dibromo-6-isobutyl-3-isopropylbenzyl chloride | 2-bromo-4-cayno-3-isopropyl-6-isobutylbenzeneacetonitrile |
| 2,4-dibromo-3,6-diisobutylbenzyl chloride | 2-bromo-4-cyano-3,6-diisobutylbenzeneacetonitrile |
| 4-bromo-2-chloro-6-ethyl-3-isobutylbenzyl chloride | 2-chloro-4-cyano-6-ethyl-3-isobutylbenzeneacetonitrile |
| 4-bromo-2-chloro-3-(1,2-dimethylpropyl)-6-propylbenzyl chloride | 2-chloro-4-cyano-3-(1,2-dimethylpropyl)-6-propylbenzeneacetonitrile |
| 4-bromo-2-chloro-3,6-diisopropylbenzyl chloride | 2-chloro-4-cyano-3,6-diisopropylbenzeneacetonitrile |

When one treats bromobenzyl chloride mixtures with cuprous cyanide in the above manner, mixtures of cyanobenzeneacetonitriles are obtained. These can be separated by fractional crystallization or chromatography, but the mixtures themselves are useful in the herbicidal methods and compositions of this invention. The following are examples of conversion to cyanobenzeneacetonitrile mixtures.

TABLE XXVIII

| Starting Material | Product |
| --- | --- |
| 4-bromo-5-tert-butyl-2-ethylbenzyl chloride and 3-bromo-5-tert-butyl-2-ethylbenzyl chloride | 5-tert-butyl-4-cyano-2-ethylbenzeneacetonitrile and 5-tert-butyl-3-cyano-2-ethylbenzeneacetonitrile |
| 4-bromo-5-sec-butyl-2-ethylbenzyl chloride and 3-bromo-5-sec-butyl-2-ethylbenzyl chloride | 5-sec-butyl-4-cyano-2-ethylbenzeneacetonitrile and 5-sec-butyl-3-cyano-2-ethylbenzeneacetonitrile |
| 4-bromo-5-(1,2-dimethylpropyl)-2-ethylbenzyl chloride and 3-bromo-5-(1,2-dimethylpropyl)-2-ethylbenzyl chloride | 4-cyano-5-(1,2-dimethylpropyl)-2-ethylbenzeneacetonitrile and 3-cyano-5-(1,2-dimethylpropyl)-2-ethylbenzeneacetonitrile |
| 4-bromo-5-(1,2-dimethylpropyl)-2-propylbenzyl chloride and 3-bromo-5-(1,2-dimethylpropyl)-2-propylbenzyl chloride | 4-cyano-5-(1,2-dimethylpropyl)-2-propylbenzeneacetonitrile and 3-cyano-5-(1,2-dimethylpropyl)-2-propylbenzeneacetonitrile |
| 4-bromo-5-(1,2-dimethylpropyl)-2-isobutylbenzyl chloride and 3-bromo-5-(1,2-dimethylpropyl)-2-isobutylbenzyl chloride | 4-cyano-5-(1,2-dimethylpropyl)-2-isobutylbenzeneacetonitrile and 3-cyano-5-(1,2-dimethylpropyl)-2-isobutylbenzeneacetonitrile |
| 4-bromo-5-tert-butyl-2-isobutylbenzyl chloride and 3-bromo-5-tert-butyl-2-isobutylbenzyl chloride | 5-tert-butyl-4-cyano-2-isobutylbenzeneacetonitrile and 5-tert-butyl-3-cyano-2-isobutylbenzeneacetonitrile |
| 4-bromo-2-ethyl-5-tert-pentylbenzyl chloride and 3-bromo-2-ethyl-5-tert-pentylbenzyl chloride | 4-cyano-2-ethyl-5-tert-pentylbenzeneacetonitrile and 3-cyano-2-ethyl-5-tert-pentylbenzeneacetonitrile |
| 3-bromo-2,5-di-tert-butylbenzyl chloride and 4-bromo-2,5-di-tert-butylbenzyl chloride | 2,5-di-tert-butyl-3-cyanobenzeneacetonitrile and 2,5-di-tert-butyl-4-cyanobenzeneacetonitrile |
| 3-bromo-5-tert-butyl-2-ethylbenzyl chloride and 4-bromo-5-tert-butyl-2-ethylbenzyl chloride | 5-tert-butyl-3-cyano-2-ethylbenzeneacetonitrile and 5-tert-butyl-4-cyano-2-ethylbenzeneacetonitrile |
| 3-bromo-5-sec-butyl-2-ethylbenzyl chloride and 4-bromo-5-sec-butyl-2-ethylbenzyl chloride | 5-sec-butyl-3-cyano-2-ethylbenzeneacetonitrile and 5-sec-butyl-4-cyano-2-ethylbenzeneacetonitrile |
| 3-bromo-5-(1,2-dimethylpropyl)-2-ethylbenzyl chloride and 4-bromo-2-(1,2-dimethylpropyl)-5-ethylbenzyl chloride | 3-cyano-5-(1,2-dimethylpropyl)-2-ethylbenzeneacetonitrile and 4-cyano-2-(1,2-dimethylpropyl)-5-ethyhlbenzeneacetonitrile |
| 3-bromo-5-(1,2-dimethylpropyl)-2-propylbenzyl chloride and 4-bromo-2-(1,2-dimethylpropyl)-5-propylbenzyl chloride | 3-cyano-5-(1,2-dimethylpropyl)-2-propylbenzeneacetonitrile and 4-cyano-2-(1,2-dimethylpropyl)-5-propylbenzeneacetonitrile |
| 3-bromo-5-(1,2-dimethylpropyl)-2-isobutylbenzyl chloride and 4-bromo-2-(1,2-dimethylpropyl)-5-isobutylbenzyl chloride | 3-cyano-5-(1,2-dimethylpropyl)-2-isobutylbenzeneacetonitrile and 4-cyano-2-(1,2-dimethylpropyl)-5-isobutylbenzeneacetonitrile |
| 3-bromo-5-tert-butyl-2-isobutylbenzyl chloride and 4-bromo-2-tert-butyl-5-isobutylbenzyl chloride | 5-tert-butyl-3-cyano-2-isobutylbenzeneacetonitrile and 2-tert-butyl-4-cyano-5-isobutylbenzeneacetonitrile |
| 3-bromo-2-ethyl-5-tert-pentylbenzyl chloride and 4-bromo-5-ethyl-2-tert-pentylbenzyl chloride | 3-cyano-2-ethyl-5-tert-pentylbenzeneacetonitrile and 4-cyano-5-ethyl-2-tert-pentylbenzeneacetonitrile |
| 3-bromo-2-methyl-5-(1,1,2,2-tetramethylpropyl)-benzyl chloride and 4-bromo-5-methyl-2-(1,1,2,2-tetramethylpropyl)benzyl chloride | 3-cyano-2-methyl-5-(1,1,2,2-tetramethylpropyl)-benzeneacetonitrile and 4-cyano-5-methyl-2-(1,1,2,2-tetramethylpropyl)benzeneacetonitrile |
| 3-bromo-2-ethyl-5-(1,1,2-trimethylpropyl)benzyl chloride and 4-bromo-5-ethyl-2-(1,1,2-trimethylpropyl)benzyl chloride | 3-cyano-2-ethyl-5-(1,1,2-trimethylpropyl)benzeneacetonitrile and 4-cyano-5-ethyl-2-(1,1,2-trimethylpropyl)benzeneacetonitrile |
| 5-bromo-2,4-diethylbenzyl chloride and 3-bromo-2,4-diethylbenzyl chloride | 5-cyano-2,4-diethylbenzeneacetonitrile and 3-cyano-2,4-diethylbenzeneacetonitrile |
| 5-bromo-2,4-diisobutylbenzyl chloride and 3-bromo-2,4-diisobutylbenzyl chloride | 5-cyano-2,4-diisobutylbenzeneacetonitrile and 3-cyano-2,4-diisobutylbenzeneacetonitrile |
| 5-bromo-4-isobutyl-2-propylbenzyl chloride and 3-bromo-4-isobutyl-2-propylbenzyl chloride | 5-cyano-4-isobutyl-2-propylbenzeneacetonitrile and 3-cyano-4-isobutyl-2-propylbenzeneacetonitrile |
| 3-bromo-2,6-dipropylbenzyl chloride and 4-bromo-2,6-dipropylbenzyl chloride | 3-cyano-2,6-dipropylbenzeneacetonitrile and 4-cyano-2,6-dipropylbenzeneacetonitrile |
| 3-bromo-2,6-diisobutylbenzyl chloride and 4-bromo-2,6-diisobutylbenzyl chloride | 3-cyano-2,6-diisobutylbenzeneacetonitrile and 4-cyano-2,6-diisobutylbenzeneacetonitrile |
| 3-bromo-2,4-diethylbenzyl chloride and 4-bromo-3,5-diethylbenzyl chloride | 3-cyano-2,4-diethylbenzeneacetonitrile and 4-cyano-3,5-diethylbenzeneacetonitrile |
| 3-bromo-2,4-diisobutylbenzyl chloride and 4-bromo-3,5-diisobutylbenzyl chloride | 3-cyano-2,4-diisobutylbenzeneacetonitrile and 4-cyano-3,5-diisobutylbenzeneacetonitrile |

EXAMPLE 23

Part A

4-Cyano-2,5-diisopropyl-α-methylbenzeneacetonitrile

A mixture of 4-cyano-2,5-diisopropylbenzeneacetonitrile (22.6 parts), 4.8 parts of a 50% sodium hydride suspension in mineral oil, and 14.2 parts of methyl iodide in 300 parts tetrahydrofuran is stirred and heated at 50° for two hours. The reaction mixture is cooled and the tetrahydrofuran stripped under reduced pressure. The solid is washed with pentane and water and dried to give 4-cyano-2,5-diisopropyl-α-methylbenzeneacetonitrile.

Part B

4-Cyano-2,5-diisopropyl-α,α-dimethylbenzeneacetonitrile

When the amounts of sodium hydride and methyl iodide are doubled, and the reacton is carried out the same way, 4-cyano-2,5-diisopropyl-α,α-dimethylbenzeneacetonitrile is obtained.

By the use of Method A, the following compounds are made:

TABLE XXIX

| Starting Material | Product |
| --- | --- |
| 3-cyano-2-isobutyl-5-tert-pentylbenzeneacetonitrile | 3-cyano-2-isobutyl-α-methyl-5-tert-pentylbenzeneacetronitrile |
| 5-cyano-2,4-diisopropyl-3-nitrobenzeneacetonitrile | 5-cyano-2,4-diisopropyl-α-methyl-3-nitrobenzene- |

TABLE XXIX-continued

| Starting Material | Product |
|---|---|
| 5-cyano-2,4,6-triethylbenzeneacetonitrile | acetonitrile<br>5-cyano-2,4,6-triethyl-α-methylbenzeneacetonitrile |

By the use of Method B, the following compounds are made:

TABLE XXX

| Starting Material | Product |
|---|---|
| 5-tert-butyl-3-cyano-2-isopropylbenzeneacetonitrile | 5-tert-butyl-3-cyano-2-isopropyl-α,α-dimethyl-benzeneacetonitrile |
| 3-cyano-2,4,6-triisopropylbenzeneacetonitrile | 3-cyano-2,4,6-triisopropyl-α,α-dimethylbenzene-acetonitrile |
| 5-sec-butyl-4-cyano-2-nitrobenzeneacetonitrile | 5-sec-butyl-4-cyano-α,α-dimethyl-α-nitrobenzene-acetonitrile |

EXAMPLE 24

2,6-Dichloro-4-cyano-3,5-diisopropylbenzeneacetonitrile

To a stirred solution of 18 parts of 4-bromo-2,6-dichloro-3,5-diisopropylbenzyl chloride in 40 parts of N-methylpyrrolidinone is added 11 parts of cuprous cyanide. The flask is rapidly heated to 200°C and kept at 205°–210°C for 1½ hours. After cooling the mixture to room temperature, the contents are poured into ice water. The suspension is stirred vigorously in a blender, filtered and washed with cold water. The cake is suspended in a mixture of 200 parts of water and 100 parts of methylene chloride. Chlorine (5½ parts) is slowly passed in under the surface at 15°C; the methylene chloride solution is separated, washed twice with dilute hydrochloric acid, then with 5% sodium bicarbonate solution, and with water. The solution is dried, filtered and evaporated. The residue is crystallized from a benzenehexane mixture to give the title compound.

The following compounds are made by appropriate substitution in the above procedure.

TABLE XXXI

| Starting Material | Product |
|---|---|
| 3-bromo-2,5-dichloro-4,6-diisopropylbenzyl chloride | 2,5-dichloro-3-cyano-4,6-diisopropylbenzeneacetonitrile |
| 5-bromo-2,4-dichloro-3,6-diisopropylbenzyl chloride | 2,4-dichloro-5-cyano-3,6-diisopropylbenzeneacetonitrile |
| 5-bromo-3,4-dichloro-2,6-diisopropylbenzyl chloride | 3,4-dichloro-5-cyano-2,6-diisopropylbenzeneacetonitrile |
| 4-bromo-3,5-dichloro-2,6-diisopropylbenzyl chloride | 3,5-dichloro-4-cyano-2,6-diisopropylbenzeneacetonitrile |
| 4-bromo-2,5-dichloro-3,6-diisopropylbenzyl chloride | 2,5-dichloro-4-cyano-3,6-diisopropylbenzeneacetonitrile |
| 5-bromo-2,3-dichloro-4,6-diisopropybenzyl chloride | 2,3-dichloro-5-cyano-4,6-diisopropylbenzeneacetonitrile |
| 4-bromo-3-chloro-2,6-diisopropylbenzyl chloride | 3-chloro-4-cyano-2,6-diisopropylbenzeneacetonitrile |
| 4-bromo-3-chloro-2,5-diisopropylbenzyl chloride | 3-chloro-4-cyano-2,5-diisopropylbenzeneacetonitrile |
| 3-bromo-2-chloro-4,6-diisopropylbenzyl chloride | 2-chloro-3-cyano-4,6-diisopropylbenzeneacetonitrile |
| 3-bromo-4-chloro-2,5-diisopropylbenzyl chloride | 4-chloro-3-cyano-2,5-diisopropylbenzeneacetonitrile |
| 5-bromo-2-chloro-3,6-diisopropylbenzyl chloride | 2-chloro-5-cyano-3,6-diisopropylbenzeneacetonitrile |
| 3-bromo-6-chloro-2,4-diisopropylbenzyl chloride | 6-chloro-3-cyano-2,4-diisopropylbenzeneacetonitrile |
| 4-bromo-2-chloro-3,5-diisopropylbenzyl chloride | 2-chloro-4-cyano-3,5-diisopropylbenzeneacetonitrile |
| 4-bromo-2-chloro-3,6-diisopropylbenzyl chloride | 2-chloro-4-cyano-3,6-diisopropylbenzeneacetonitrile |
| 3-bromo-2,4-di-tert-buty-5-chlorobenzyl chloride | 2,4-di-tert-5-chloro-3-cyanobenzeneacetonitrile |
| 5-bromo-4-tert-butyl-3-chloro-2-ethylbenzyl chloride | 4-tert-butyl-3-chloro-5-cyano-2-ethylbenzeneacetonitrile |
| 2-sec-butyl-5-bromo-3-chloro-6-ethylbenzyl chloride | 2-sec-butyl-3-chloro-5-cyano-6-ethylbenzeneacetonitrile |
| 3-bromo-4-chloro-2,6-diisobutylbenzyl chloride | 4-chloro-3-cyano-2,6-diisobutylbenzeneacetonitrile |
| 2,5-dibromo-3,6-diisopropylbenzyl chloride | 2-bromo-5-cyano-3,6-diisopropylbenzeneacetonitile |
| 2,5-dibromo-3,6-di-sec-butylbenzyl chloride | 2-bromo-5-cyano-3,6-di-sec-butylbenzeneacetonitrile |
| 3,6-dibromo-2,4-di-tert-butylbenzyl chloride | 6-bromo-2,4-di-tert-butyl-3-cyanobenzeneacetonitrile |
| 4-bromo-2-tert-butyl-3-chloro-5-isopropyl-benzyl chloride | 2-tert-butyl-3-chloro-4-cyano-5-isopropylbenzene-acetonitrile |
| 4-bromo-2-sec-butyl-3-chloro-5-isopropyl-benzyl chloride | 2-sec-butyl-3-chloro-4-cyano-5-isopropylbenzeneacetonitrile |
| 4-bromo-3-chloro-2-isobutyl-5-isopropylbenzyl chloride | 3-chloro-4-cyano-2-isobutyl-5-isopropylbenzeneacetonitrile |
| 4-bromo-2,5-di-sec-butyl-3-chlorobenzyl chloride | 2,5-di-sec-butyl-3-chloro-4-cyanobenzeneacetonitrile |
| 4-bromo-3-chloro-2,5-diisobutylbenzyl chloride | 3-chloro-4-cyano-2,5-diisobutylbenzeneacetonitrile |
| 4-bromo-2-tert-butyl-3-chloro-5-isobutylbenzyl chloride | 2-tert-butyl-3-chloro-4-cyano-5-isobutylbenzene-acetonitrile |
| 4-bromo-2-tert-butyl-3-chloro-5-ethylbenzyl chloride | 2-tert-butyl-3-chloro-4-cyano-5-ethylbenzeneacetonitrile |

Alkylbenzenes can be nitrated in the same manner as described in Example 10, except that the temperature is maintained at 0°C. When the indicated alkylbenzenes are nitrated, the resulting nitro compounds can be used for the preparation of the corresponding anilines:

TABLE XXXII

| Starting Material | Product |
| --- | --- |
| p-diisobutylbenzene | 1,4-diisobutyl-2-nitrobenzene |
| m-diisopropylbenzene | 2,4-diisopropyl-1-nitrobenzene |
| p-(1,2-dimethylpropyl)ethylbenzene | 4-(1,2-dimethylpropyl)-1-ethyl-2-nitrobenzene |
| p-di-sec-butylbenzene | 2,5-di-sec-butylnitrobenzene |
| p-dipropylbenzene | 1-nitro-2,5-dipropylbenzene |
| p-diisopropylbenzene | 2,5-diisopropylnitrobenzene |
| p-isobutylcumene | 2-isobutyl-5-isopropylnitrobenzene |
| p-tert-butylcumene | 5-tert-butyl-2-isopropylnitrobenzene |
| p-sec-butylcumene | 5-sec-butyl-2-isopropylnitrobenzene |
| p-tert-pentylcumene | 2-isopropyl-1-nitro-5-tert-pentylbenzene |

EXAMPLE 25

2,5-Diisobutylaniline

A solution of 22.5 parts of 1,4-diisobutyl-2-nitrobenzene in 75 parts of ethanol is hydrogenated in the presence of 0.4 part platinum oxide catalyst in a Parr hydrogenation apparatus until 0.3 molar equivalents of hydrogen are consumed. The catalyst is filtered off; the ethanol is removed; and 2,5-diisobutylaniline is recovered.

By replacing 1,4-diisobutyl-2-nitrobenzene with the following nitro compounds, these anilines are obtained:

TABLE XXXIII

| Starting Material | Product |
| --- | --- |
| 2,4-diisopropylnitrobenzene | 2,4-diisopropylaniline |
| 4-(1,2-dimethylpropyl)-1-ethyl-2-nitrobenzene | 5-1,2-dimethylpropyl)-2-ethylaniline |
| 1-ethyl-2-nitro-4-(1,1,2,2-tetramethyl)benzene | 2-ethyl-5-(1,1,2,2-tetramethyl)aniline |
| 2,5-di-sec-butylnitrobenzene | 2,5-di-sec-butylaniline |
| 1-nitro-2,5-dipropylbenzene | 2,5-dipropylaniline |
| 2,5-diisopropylnitrobenzene | 2,5-diisopropylaniline |
| 2-isobutyl-5-isopropylnitrobenzene | 2-isobutyl-5-ispropylaniline |
| 5-tert-butyl-2-isopropylnitrobenzene | 5-tert-butyl-2-isopropylaniline |

EXAMPLE 26

2,6-Diethylacetanilide

A solution of 74.5 parts of 2,6-diethylaniline in 200 parts of dimethylformamide is treated with 56 parts of acetic anhydride at 10°C. The mixture is stirred at 40° for one hour, poured into ice and water and stirred. The solid 2,6-diethylacetanilide is filtered, washed with water and dried.

EXAMPLE 27

2,6-Diethyl-4-nitroaniline

A solution of 58 parts of 2,6-diethylacetanilide in 100 parts of glacial acetic acid and 184 parts of concentrated sulfuric acid is treated at 10° with a mixture of 19.5 parts by volume of concentrated nitric acid and 13 parts by volume of concentrated sulfuric acid. After addition is completed, the mixture is stirred at 25°C for 1 hour. It is then poured into water and ice, and the solid filtered, washed with water and dried. The 2,6-diethyl-4-nitroacetanilide (30 parts) is treated with 150 parts by volume of refluxing 70% sulfuric acid solution for one hour, and the mixture poured onto ice and made basic with 5N sodium hydroxide solution. The solid 2,6-diethyl-4-nitroaniline is filtered, washed with water and recrystallized from methyl alcohol-water.

EXAMPLE 28

3,5-Diethylnitrobenzene

A solution of 19.4 parts of 2,6-diethyl-4-nitroaniline in 40 parts by volume of concentrated hydrochloric acid is diluted with 80 parts of water and added to 100 parts of ice. A solution of 7 parts of sodium nitrite in 15 parts of water is added and the filtered diazonium solution treated with 150 parts by volume of 50% hypophosphorous acid and kept cold for 24 hours. The 3,5-diethylnitrobenzene which separates is extracted with ether and distilled, b.p. 190°/20mm.

The following dialkylnitrobenzenes are made from the appropriate dialkylnitroanilines by the above procedure.

TABLE XXXIV

| Starting Material | Product |
| --- | --- |
| 4-nitro-2,6-dipropylaniline | 1-nitro-3,5-dipropylbenzene |
| 2,6-diisopropyl-4-nitroaniline | 3,5-diisopropylnitrobenzene |
| 2,6-diisobutyl-4-nitroaniline | 3,5-diisobutylnitrobenzene |
| 2-ethyl-6-isopropyl-4-nitroaniline | 3-ethyl-5-isopropylnitrobenzene |
| 2-isobutyl-4-nitro-6-propylaniline | 3-isobutyl-1-nitro-5-propylbenzene |
| 2,6-di-sec-butyl-4-nitroaniline | 3,5-di-sec-butylnitrobenzene |
| 2-sec-butyl-6-isopropyl-4-nitroaniline | 3-sec-butyl-5-isopropylnitrobenzene |
| 2,6-di-tert-butyl-4-nitroaniline | 3,5-di-tert-butylnitrobenzene |

EXAMPLE 29

2,6-Diethyl-4-nitrobenzyl Chloride and 2,4-Diethyl-6-nitrobenzyl Chloride 3,5-Diethylnitrobenzene (10 parts) is dissolved in 29 parts of chloromethylmethyl ether, and 10 parts of 60% fuming sulfuric acid is added slowly with stirring. After standing for 5 minutes, the dark hot mixture is diluted with water and the precipitate is filtered and dried. Distillation under reduced pressure first gives the starting material and then a mixture of 2,6-diethyl-4-nitrobenzyl chloride and 2,4-diethyl-6-nitrobenzyl chloride. These are separated by chromatography on Florosil or alumina and fractional crystallization.

The following dialkylnitrobenzyl chlorides are made from the appropriate dialkylnitrobenzenes by the above procedure.

TABLE XXXV

| Starting Material | Product |
|---|---|
| 1-nitro-3,5-dipropylbenzene | 4-nitro-2,6-dipropylbenzyl chloride |
| | 6-nitro-2,4-dipropylbenzyl chloride |
| 3,5-diisopropylnitrobenzene | 2,6-diisopropyl-4-nitrobenzyl chloride |
| | 2,4-diisopropyl-6-nitrobenzyl chloride |
| 3,5-diisobutylnitrobenzene | 2,6-diisobutyl-4-nitrobenzyl chloride |
| | 2,4-diisobutyl-6-nitrobenzyl chloride |
| 3-isobutyl-1-nitro-5-propylbenzene | 2-isobutyl-4-nitro-6-propylbenzyl chloride |
| | 4-isobutyl-6-nitro-2-propylbenzyl chloride |
| 3-ethyl-5-isopropylnitrobenzene | 2-ethyl-6-isopropyl-4-nitrobenzyl chloride |
| | 2-ethyl-4-isopropyl-6-nitrobenzyl chloride |
| 3,5-di-sec-butylnitrobenzene | 2,6-di-sec-butyl-4-nitrobenzyl chloride |
| | 2,4-di-sec-butyl-6-nitrobenzyl chloride |
| 3,5-di-tert-butylnitrobenzene | 2,6-di-tert-butyl-4-nitrobenzyl chloride |
| | 2,4-di-tert-butyl-6-nitrobenzyl-chloride |
| 3-sec-butyl-5-isopropylnitrobenzene | 2-sec-butyl-6-isopropyl-4-nitrobenzyl chloride |
| | 4-sec-butyl-2-isopropyl-6-nitrobenzyl chloride |

EXAMPLE 30

3-Cyano-2,6-diethyl-4-nitrobenzene acetonitrile 2,6-Diethyl-4-nitrobenzyl chloride is brominated to give 3-bromo-2,6-diethyl-4-nitrobenzyl chloride by the procedure used to prepare 4-bromo-2-isobutyl-5-isopropylbenzyl chloride. 3-Bromo-2,6-diethyl-4-nitrobenzyl chloride is then converted to 3-cyano-2,6-diethyl-4-nitrobenzeneacetonitrile with cuprous cyanide by the procedure used to prepare 4-cyano-2,5-diisopropylbenzeneacetonitrile.

The following 2,6-dialkyl-3-cyano-4-nitrobenzeneacetonitriles are made from the appropriate 2,6-dialkyl-4-nitrobenzyl chlorides using the above procedure.

EXAMPLE 31

3-Cyano-2,4-diethyl-6-nitrobenzeneacetonitrile and 5-Cyano-2,4-diethyl-6-nitrobenzeneacetonitrile 2,4-Diethyl-6-nitrobenzyl chloride is brominated by the procedure used to prepare 4-bromo-2-isobutyl-5-isopropylbenzyl chloride to form a mixture containing 3-bromo-2,4-diethyl-6-nitrobenzyl chloride and 5-bromo-2,4-diethyl-6-nitrobenzyl chloride. This mixture is treated with cuprous cyanide by the method used to prepare 4-cyano-2,5-diisopropylbenzeneacetonitrile to give a mixture containing 3-cyano-2,4-diethyl-6-nitrobenzeneacetonitrile and 5-cyano-2,4-diethyl-6-nitrobenzeneacetonitrile. These compounds can be separated by fractional crystallization or chromatography, but the mixture itself is useful in the herbicidal methods and compositions of this invention.

The following 2,4-dialkyl-3 (or 5)-cyano-6-nitrobenzeneacetonitriles are made from the appropriate 2,4-dialkyl-6-nitrobenzyl chlorides by the above procedure.

TABLE XXXVI

| Starting Material | Product |
|---|---|
| 4-nitro-2,6-dipropylbenzyl chloride | 3-cyano-4-nitro-2,6-dipropylbenzeneacetonitrile |
| 2,6-diisopropyl-4-nitrobenzyl chloride | 3-cyano-2,6-diisopropyl-4-nitrobenzeneacetonitrile |
| 2,6-diisobutyl-4-nitrobenzyl chloride | 3-cyano-2,6-diisobutyl-4-nitrobenzeneacetonitrile |
| 2-isobutyl-4-nitro-6-propylbenzyl chloride | 3-cyano-2-isobutyl-4-nitro-6-propylbenzeneacetonitrile |
| 2-ethyl-6-isopropyl-4-nitrobenzyl chloride | 3-cyano-2-ethyl-6-isopropyl-4-nitrobenzeneacetonitrile |
| 2,6-di-sec-butyl-4-nitrobenzyl chloride | 2,6-di-sec-butyl-3-cyano-4-nitrobenzeneacetonitrile |
| 2,6-di-tert-butyl-4-nitrobenzyl chloride | 2,6-di-tert-butyl-3-cyano-4-nitrobenzeneacetonitrile |
| 2-sec-butyl-6-isopropyl-4-nitrobenzyl chloride | 2-sec-butyl-5-cyano-6-isopropyl-4-nitrobenzeacetonitrile |

TABLE XXXVII

| Starting Material | Product |
|---|---|
| 6-nitro-2,4-dipropylbenzyl chloride | 3-cyano-6-nitro-2,4-dipropylbenzeneacetonitrile |
| | 5-cyano-6-nitro-2,4-dipropylbenzeneacetonitrile |
| 2,4-diisopropyl-6-nitrobenzyl chloride | 3-cyano-2,4-diisopropyl-6-nitrobenzeneacetonitrile |
| | 5-cyano-2,4-diisopropyl-6-nitrobenzeneacetonitrile |
| 2,4-diisobutyl-6-nitrobenzyl chloride | 3-cyano-2,4-diisobutyl-6-nitrobenzeneacetonitrile |
| | 5-cyano-2,4-diisobutyl-6-nitrobenzeneacetonitrile |
| 2,4-di-sec-butyl-6-nitrobenzyl chloride | 2,4-di-sec-butyl-3-cyano-6-nitrobenzeneacetonitrile |
| | 2,4-di-sec-butyl-5-cyano-6-nitrobenzeneacetonitrile |
| 2,4-di-tert-butyl-6-nitrobenzyl chloride | 2,4-di-tert-butyl-3-cyano-6-nitrobenzeneacetonitrile |
| | 2,4-di-tert-butyl-5-cyano-6-nitrobenzeneacetonitrile |
| 4-sec-butyl-2-isopropyl-6-nitrobenzyl chloride | 4-sec-butyl-3-cyano-2-isopropyl-6-nitrobenzeneacetonitrile |
| | 4-sec-butyl-5-cyano-2-isopropyl-6-nitrobenzeneacetonitrile |

EXAMPLE 32

4-Cyano-2,5-diisobutyl-3-nitrobenzeneacetonitrile 2,5-Diisobutylnitrobenzene is treated with chloromethylmethyl ether in the presence of 60% fuming sulfuric acid by the procedure of Example 29 to yield 2,5-diisobutyl-3-nitrobenzyl chloride. This is brominated by the procedure (of Example 11) to form 4-bromo-2,5-diisobutyl-3-nitrobenzyl chloride and 6-bromo-2,5-diisobutyl-3-nitrobenzyl chloride. This mixture is separated by fractional crystallization or chromatography and the 4-bromo-2,5-diisobutyl-3-nitrobenzyl chloride is treated with cuprous cyanide by the procedure of Example 22 to give 4-cyano-2,5-diisobutyl-3-nitrobenzeneacetonitrile.

The following compounds are made by appropriate substitution in the preceding procedures.

TABLE XXXIX

| Starting Material | Product |
| --- | --- |
| 2,4-di-sec-butyl-5-cyanobenzeneacetonitrile | 2,4-di-sec-butyl-5-cyano-3-nitrobenzeneacetonitrile |
| 4-sec-butyl-2-tert-butyl-5-cyanobenzeneacetonitrile | 4-sec-butyl-2-tert-butyl-5-cyano-nitrobenzene acetonitrile |
| 4-tert-butyl-5-cyano-2-ethylbenzeneacetonitrile | 4-tert-butyl-5-cyano-2-ethyl-3-nitrobenzeneacetonitrile |
| 4-cyano-2,5-diisobutylbenzeneacetonitrile | 4-cyano-2,5-diisobutyl-6-nitrobenzeneacetonitrile |
| 3-cyano-4-ethyl-2-isopropylbenzeneacetonitrile | 3-cyano-4-ethyl-2-isopropyl-5-nitrobenzeneacetonitrile |
| 5-cyano-2-(1,2-dimethylpropyl)-4-isopropylbenzene-acetonitrile | 5-cyano-2-(1,2-dimethylpropyl)-4-isopropyl-3-nitro-benzeneacetonitrile |
| 4-tert-butyl-5-cyano-2-isobutylbenzeneacetonitrile | 4-tert-butyl-5-cyano-2-isobutyl-3-nitrobenzeneacetonitrile |

When one nitrates mixtures of cyanobenzeneacetonitriles, mixtures of nitrocyanobenzeneacetonitriles are obtained. These can be separated by fractional crystallization or chromatography, but the mixtures themselves are useful in the herbicidal methods and compositions of this invention. The following are examples of the preparation of nitrocyanobenzeneacetonitrile mixtures.

TABLE XXXX

| Starting Material | Product |
| --- | --- |
| 3-cyano-2,6-diisobutylbenzeneacetonitrile and 4-cyano-2,6-diisobutylbenzeneacetonitrile | 3-cyano-2,6-diisobutyl-5-nitrobenzeneacetonitrile and 4-cyano-2,6-diisobutyl-3-nitrobenzeneacetonitrile |
| 3-cyano-2,4-diethylbenzeneacetonitrile and 4-cyano-3,5-diethylbenzeneacetonitrile | 3-cyano-2,4-diethyl-5-nitrobenzeneacetonitrile and 4-cyano-3,5-diethyl-2-nitrobenzeneacetonitrile |
| 3-cyano-2-ethyl-5-neopentylbenzeneacetonitrile and 4-cyano-5-ethyl-2-neopentylbenzene-acetonitrile | 3-cyano-2-ethyl-5-neopentyl-6-nitrobenzeneacetonitrile, 3-cyano-2-ethyl-5-neopentyl-4-nitro-benzeneacetonitrile, and 4-cyano-5-ethyl-2-neopentyl-6-nitrobenzeneacetonitrile |

TABLE XXXVIII

| Starting Material | Product |
| --- | --- |
| 2,5-di-sec-butylnitrobenzene | 2,5-di-sec-butyl-4-cyano-3-nitrobenzeneacetonitrile |
| 1-nitro-2,5-dipropylbenzene | 4-cyano-3-nitro-2,5-dipropylbenzeneacetonitrile |
| 2,5-diisopropylnitrobenzene | 4-cyano-2,5-diisopropyl-3-nitrobenzeneacetonitrile |
| 2-isobutyl-5-isopropylnitrobenzene | 4-cyano-2-isobutyl-5-isopropyl-3-nitrobenzeneacetonitrile |
| 2-tert-butyl-2-isopropylnitrobenzene | 5-tert-butyl-4-cyano-2-isopropyl-3-nitrobenzeneacetonitrile |
| 5-sec-butyl-2-isopropylnitrobenzene | 5-sec-butyl-4-cyano-2-isopropyl-3-nitrobenzeneacetonitrile |
| 2-isopropyl-1-nitro-5-tert-pentylbenzene | 4-cyano-2-isopropyl-3-nitro-5-tert-pentylbenzene-acetonitrile |

EXAMPLE 33

5-Cyano-2,4-diisobutyl-3-nitrobenzeneacetonitrile

A round bottom flask is charged with 25 parts of 98% sulfuric acid and 25 parts of 20% fuming sulfuric acid and cooled to 0°; then, 20 parts of 90% fuming nitric acid is added. Twenty parts of 5-cyano-2,4-diisobutyl-benzeneacetonitrile is added in portions, and the mixture is warmed to 50° with stirring. After two hours, the solution is poured onto ice and the precipitate of 5-cyano-2,4-diisobutyl-3-nitrobenzeneacetonitrile is collected and dried.

In a similar manner, using starting materials prepared by previously described procedures one can prepare the following:

Where a secondary or tertiary alkyl group, i.e. isopropyl group, is activated by appropriate substitution (electron-donating groups), the nitration results in displacement of the alkyl group by nitro group. This is shown in the following table, wherein the starting materials are prepared by previously described procedures.

TABLE XXXXI

| Starting Material | Product |
| --- | --- |
| 4-cyano-2,5-diisopropylbenzeneacetonitrile | 4-cyano-5-isopropyl-2-nitrobenzeneacetonitrile |
| 2,5-di-sec-butyl-4-cyanobenzeneacetonitrile | 5-sec-butyl-4-cyano-2-nitrobenzeneacetonitrile |

TABLE XXXXI-continued

| Starting Material | Product |
| --- | --- |
| 4-cyano-2,5-di-tert-pentylbenzeneacetonitrile | 4-cyano-2-nitro-5-tert-pentylbenzeneacetonitrile |
| 4-cyano-2,6-diisopropylbenzeneacetonitrile | 4-cyano-2-isopropyl-6-nitrobenzeneacetonitrile |
| 2,6-di-sec-butyl-4-cyanobenzeneacetonitrile | 2-sec-butyl-4-cyano-6-nitrobenzeneacetonitrile |
| 2-sec-butyl-4-cyano-6-propylbenzeneacetonitrile | 4-cyano-6-nitro-2-propylbenzeneacetonitrile |
| 2-sec-butyl-4-cyano-6-(1,2-dimethylpropyl)-benzeneacetonitrile | 4-cyano-2-(1,2-dimethylpropyl)-6-nitrobenzeneacetonitrile |
| 2-sec-butyl-6-tert-butyl-4-cyanobenzeneacetonitrile | 2-tert-butyl-4-cyano-6-nitrobenzeneacetonitrile |
| 4-cyano-3,5-diisopropylbenzeneacetonitrile | 4-cyano-3-isopropyl-5-nitrobenzeneacetonitrile |
| 3,5-di-sec-butyl-4-cyanobenzeneacetonitrile | 3-sec-butyl-4-cyano-5-nitrobenzeneacetonitrile |
| 3-sec-butyl-4-cyano-5-propylbenzeneacetonitrile | 4-cyano-3-nitro-5-propylbenzeneacetonitrile |
| 3-sec-butyl-5-tert-butyl-4-cyanobenzeneacetonitrile | 3-tert-butyl-4-cyano-5-nitrobenzeneacetonitrile |

The following halocyanodialkylbenzeneacetonitriles are prepared by the nitration method of Example 10.

TABLE XXXXII

| Starting Material | Product |
| --- | --- |
| 3-chloro-4-cyano-2,5-diethylbenzeneacetonitrile | 5-chloro-4-cyano-3,6-diethyl-2-nitrobenzeneacetonitrile |
| 3-chloro-4-cyano-2,5-dipropylbenzeneacetonitrile | 5-chloro-4-cyano-2-nitro-3,6-dipropylbenzeneacetonitrile |
| 3-bromo-4-cyano-2,5-dipropylbenzeneacetonitrile | 5-bromo-4-cyano-2-nitro-3,6-dipropylbenzeneacetonitrile |
| 3-chloro-4-cyano-2,5-diisobutylbenzeneacetonitrile | 5-chloro-4-cyano-3,6-diisobutyl-2-nitrobenzeneacetonitrile |
| 3-bromo-4-cyano-2,5-diisobutylbenzeneacetonitrile | 5-bromo-4-cyano-3,6-diisobutyl-2-nitrobenzeneacetonitrile |
| 2,5-di-tert-butyl-3-chloro-4-cyanobenzeneacetonitrile | 3,6-di-tert-butyl-5-chloro-4-cyano-2-nitrobenzeneacetonitrile |
| 3-chloro-4-cyano-5-isobutyl-2-methylbenzeneacetonitrile | 5-chloro-4-cyano-3-isobutyl-6-methyl-2-nitrobenzeneacetonitrile |
| 3-chloro-4-cyano-2-isobutyl-5-methylbenzeneacetonitrile | 5-chloro-4-cyano-6-isobutyl-3-methyl-2-nitrobenzeneacetonitrile |
| 5-tert-butyl-3-chloro-4-cyano-2-ethylbenzeneacetonitrile | 3-tert-butyl-5-chloro-4-cyano-6-ethyl-2-nitrobenzeneacetonitrile |
| 5-tert-butyl-3-chloro-4-cyao-2-propylbenzeneacetonitrile | 3-tert-butyl-5-chloro-4-cyano-2-nitro-6-propylbenzeneacetonitrile |
| 2-tert-butyl-3-chloro-4-cyano-5-propylbenzeneacetonitrile | 6-tert-butyl-5-chloro-4-cyano-2-nitro-3-propylbenzeneacetonitrile |
| 2-tert-butyl-3-chloro-4-cyano-5-isopropylbenzeneacetonitrile | 6-tert-butyl-5-chloro-4-cyano-3-isopropyl-2-nitrobenzeneacetonitrile |
| 5-sec-butyl-2-tert-butyl-3-chloro-4-cyanobenzeneacetonitrile | 3-sec-butyl-6-tert-butyl-5-chloro-4-cyano-2-nitrobenzeneacetonitrile |
| 5-sec-butyl-3-chloro-4-cyano-2-isobutylbenzeneacetonitrile | 3-sec-butyl-5-chloro-4-cyano-6-isobutyl-2-nitrobenzeneacetonitrile |
| 3-chloro-4-cyano-2-isobutyl-5-isopropylbenzeneacetonitrile | 5-chloro-4-cyano-6-isobutyl-3-isopropyl-2-nitrobenzeneacetonitrile |
| 2-chloro-4-cyano-3,5-diethylbenzeneacetonitrile | 2-chloro-4-cyano-3,5-diethyl-6-nitrobenzeneacetonitrile |
| 2-chloro-4-cyano-3,5-dipropylbenzeneacetonitrile | 2-chloro-4-cyano-6-nitro-3,5-dipropylbenzeneacetonitrile |
| 2-chloro-4-cyano-3,5-diisopropylbenzeneacetonitrile | 2-chloro-4-cyano-3,5-diisopropyl-6-nitrobenzeneacetonitrile |
| 2-chloro-4-cyano-3,5-diisobutylbenzeneacetonitrile | 2-chloro-4-cyano-3,5-diisobutyl-6-nitrobenzeneacetonitrile |
| 3,5-di-sec-butyl-2-chloro-4-cyanobenzeneacetonitrile | 3,5-di-sec-butyl-2-chloro-4-cyano-6-nitrobenzeneacetonitrile |
| 2-bromo-3,5-di-sec-butyl-4-cyanobenzeneacetonitrile | 2-bromo-3,5-di-sec-butyl-4-cyano-6-nitrobenzeneacetonitrile |
| 2-bromo-4-cyano-3,5-diisobutylbenzeneacetonitrile | 2-bromo-4-cyano-3,5-diisobutyl-6-nitrobenzeneacetonitrile |
| 2-bromo-3,5-di-tert-butyl-4-cyanobenzeneacetonitrile | 2-bromo-3,5-di-tert-butyl-4-cyano-6-nitrobenzeneacetonitrile |
| 3,5-di-tert-butyl-2-chloro-4-cyanobenzeneacetonitrile | 3,5-di-tert-butyl-2-chloro-4-cyano-6-nitrobenzeneacetonitrile |
| 5-tert-butyl-2-chloro-4-cyano-3-ethylbenzeneacetonitrile | 5-tert-butyl-2-chloro-4-cyano-3-ethyl-6-nitrobenzeneacetonitrile |
| 5-tert-butyl-2-chloro-4-cyano-3-propylbenzeneacetonitrile | 5-tert-butyl-2-chloro-4-cyano-6-nitro-3-propylbenzeneacetonitrile |
| 5-tert-butyl-2-chloro-4-cyano-3-isopropylbenzeneacetonitrile | 5-tert-butyl-2-chloro-4-cyano-3-isopropyl-6-nitrobenzeneacetonitrile |
| 5-tert-butyl-2-chloro-4-cyano-3-isobutylbenzeneacetonitrile | 5-tert-butyl-2-chloro-4-cyano-3-isobutyl-6-nitrobenzeneacetonitrile |
| 3-sec-butyl-5-tert-butyl-2-chloro-4-cyanobenzeneacetonitrile | 3-sec-butyl-5-tert-butyl-2-chloro-4-cyano-6-nitrobenzeneacetonitrile |
| 2-bromo-5-tert-butyl-4-cyano-3-ethylbenzeneacetonitrile | 2-bromo-5-tert-butyl-4-cyano-3-ethyl-6-nitrobenzeneacetonitrile |
| 2-bromo-4-cyano-3-isobutyl-5-isopropylbenzeneacetonitrile | 2-bromo-4-cyano-3-isobutyl-5-isopropyl-6-nitrobenzeneacetonitrile |
| 2-chloro-4-cyano-3-isobutyl-5-isopropylbenzeneacetonitrile | 2-chloro-4-cyano-3-isobutyl-5-isopropyl-6-nitrobenzeneacetonitrile |
| 5-sec-butyl-2-chloro-4-cyano-3-isobutylbenzeneacetonitrile | 5-sec-butyl-2-chloro-4-cyano-3-isobutyl-6-nitrobenzeneacetonitrile |
| 2-bromo-5-sec-butyl-4-cyano-3-isobutylbenzeneacetonitrile | 2-bromo-5-sec-butyl-4-cyano-3-isobutyl-6-nitrobenzeneacetonitrile |
| 5-sec-butyl-2-chloro-4-cyano-3-isopropylbenzeneacetonitrile | 5-sec-butyl-2-chloro-4-cyano-3-isopropyl-6-nitrobenzeneacetonitrile |
| 2-chloro-3-cyano-4,6-diethylbenzeneacetonitrile | 2-chloro-3-cyano-4,6-diethyl-5-nitrobenzeneacetonitrile |
| 2-bromo-3-cyano-4,6-diethylbenzeneacetonitrile | 2-bromo-3-cyano-4,6-diethyl-5-nitrobenzeneaceto- |

TABLE XXXXII-continued

| Starting Material | Product |
|---|---|
| | nitrile |
| 2-bromo-3-cyano-4,6-dipropylbenzeneacetonitrile | 2-bromo-3-cyano-5-nitro-4,6-dipropylbenzeneacetonitrile |
| 2-chloro-3-cyano-4,6-dipropylbenzeneacetonitrile | 2-chloro-3-cyano-5-nitro-4,6-dipropylbenzeneacetonitrile |
| 2-chloro-3-cyano-4,6-diisobutylbenzeneacetonitrile | 2-chloro-3-cyano-4,6-diisobutyl-5-nitrobenzeneacetonitrile |
| 2-bromo-3-cyano-4,6-diisobutylbenzeneacetonitrile | 2-bromo-3-cyano-4,6-diisobutyl-5-nitrobenzeneacetonitrile |
| 2-bromo-4,6-di-tert-butyl-3-cyanobenzeneacetonitrile | 2-bromo-4,6-di-tert-butyl-3-cyano-5-nitrobenzeneacetonitrile |
| 4,6-di-tert-butyl-2-chloro-3-cyanobenzeneacetonitrile | 4,6-di-tert-butyl-2-chloro-3-cyano-5-nitrobenzeneacetonitrile |
| 6-tert-butyl-2-chloro-3-cyano-4-ethylbenzeneacetonitrile | 6-tert-butyl-2-chloro-3-cyano-4-ethyl-5-nitrobenzeneacetonitrile |
| 2-bromo-6-tert-butyl-3-cyano-4-propylbenzeneacetonitrile | 2-bromo-6-tert-butyl-3-cyano-5-nitro-4-propylbenzeneacetonitrile |
| 2-bromo-6-tert-butyl-3-cyano-4-isopropylbenzeneacetonitrile | 2-bromo-6-tert-butyl-3-cyano-4-isopropyl-5-nitrobenzeneacetonitrile |
| 6-tert-butyl-2-chloro-3-cyano-4-isobutylbenzeneacetonitrile | 6-tert-butyl-2-chloro-3-cyano-4-isobutyl-5-nitrobenzeneacetonitrile |
| 6-tert-butyl-4-sec-butyl-2-chloro-3-cyanobenzeneacetonitrile | 6-tert-butyl-4-sec-butyl-2-chloro-3-cyano-5-nitrobenzeneacetonitrile |
| 2-bromo-4-sec-butyl-6-tert-butyl-3-cyanobenzeneacetonitrile | 2-bromo-4-sec-butyl-6-tert-butyl-3-cyano-5-nitrobenzeneacetonitrile |
| 2-bromo-6-sec-butyl-4-tert-butyl-3-cyanobenzeneacetonitrile | 2-bromo-6-sec-butyl-4-tert-butyl-3-cyano-5-nitrobenzeneacetonitrile |
| 6-sec-butyl-4-tert-butyl-2-chloro-3-cyanobenzeneacetonitrile | 6-sec-butyl-4-tert-butyl-2-chloro-3-cyano-5-nitrobenzeneacetonitrile |
| 4-tert-butyl-2-chloro-3-cyano-6-isobutylbenzeneacetonitrile | 4-tert-butyl-2-chloro-3-cyano-6-isobutyl-5-nitrobenzeneacetonitrile |
| 2-bromo-3-cyano-6-isobutyl-4-isopropylbenzeneacetonitrile | 2-bromo-3-cyano-6-isobutyl-4-isopropyl-5-nitrobenzeneacetonitrile |
| 4-sec-butyl-2-chloro-3-cyano-6-propylbenzeneacetonitrile | 4-sec-butyl-2-chloro-3-cyano-5-nitro-6-propylbenzeneacetonitrile |
| 5-bromo-3-cyano-2,4-diethylbenzeneacetonitrile | 5-bromo-3-cyano-2,4-diethyl-6-nitrobenzeneacetonitrile |
| 5-chloro-3-cyano-2,4-dipropylbenzeneacetonitrile | 5-chloro-3-cyano-6-nitro-2,4-dipropylbenzeneacetonitrile |
| 5-bromo-3-cyano-2,4-diisopropylbenzeneacetonitrile | 5-bromo-3-cyano-2,4-diisopropyl-6-nitrobenzeneacetonitrile |
| 5-chloro-3-cyano-2,4-diisopropylbenzeneacetonitrile | 5-chloro-3-cyano-2,4-diisopropyl-6-nitrobenzeneacetonitrile |
| 5-bromo-3-cyano-2,4-diisobutylbenzeneacetonitrile | 5-bromo-3-cyano-2,4-diisobutyl-6-nitrobenzeneacetonitrile |
| 5-chloro-3-cyano-2,4-diisobutylbenzeneacetonitrile | 5-chloro-3-cyano-2,4-diisobutyl-6-nitrobenzeneacetonitrile |
| 2,4-di-sec-butyl-5-chloro-3-cyanobenzeneacetonitrile | 2,4-di-sec-butyl-5-chloro-3-cyano-6-nitrobenzeneacetonitrile |
| 5-bromo-2,4-di-sec-butyl-3-cyanobenzeneacetonitrile | 5-bromo-2,4-di-sec-butyl-3-cyano-6-nitrobenzeneacetonitrile |
| 5-bromo-2,4-di-tert-butyl-3-cyanobenzeneacetonitrile | 5-bromo-2,4-di-tert-butyl-3-cyano-6-nitrobenzeneacetonitrile |
| 2,4-di-tert-butyl-5-chloro-3-cyanobenzeneacetonitrile | 2,4-di-tert-butyl-5-chloro-3-cyano-6-nitrobenzeneacetonitrile |
| 2-tert-butyl-5-chloro-3-cyano-4-ethylbenzeneacetonitrile | 2-tert-butyl-5-chloro-3-cyano-4-ethyl-6-nitrobenzeneacetonitrile |
| 4-tert-butyl-5-chloro-3-cyano-2-ethylbenzeneacetonitrile | 4-tert-butyl-5-chloro-3-cyano-2-ethyl-6-nitrobenzeneacetonitrile |
| 4-tert-butyl-5-chloro-3-cyano-2-propylbenzeneacetonitrile | 4-tert-butyl-5-chloro-3-cyano-6-nitro-2-propylbenzeneacetonitrile |
| 4-tert-butyl-5-chloro-3-cyano-2-isopropylbenzeneacetonitrile | 4-tert-butyl-5-chloro-3-cyano-2-isopropyl-6-nitrobenzeneacetonitrile |
| 4-tert-butyl-5-chloro-3-cyano-2-isobutylbenzeneacetonitrile | 4-tert-butyl-5-chloro-3-cyano-2-isobutyl-6-nitrobenzeneacetonitrile |
| 2-tert-butyl-4-sec-butyl-5-chloro-3-cyanobenzeneacetonitrile | 2-tert-butyl-4-sec-butyl-5-chloro-3-cyano-6-nitrobenzeneacetonitrile |
| 4-sec-butyl-5-chloro-3-cyano-2-ispropylbenzeneacetonitrile | 4-sec-butyl-5-chloro-3-cyano-2-isopropyl-6-nitrobenzeneacetonitrile |
| 5-bromo-3-cyano-2-isobutyl-4-isopropylbenzeneacetonitrile | 5-bromo-3-cyano-2-isobutyl-4-isopropyl-6-nitrobenzeneacetonitrile |
| 5-bromo-3-cyano-4-isobutyl-2-isopropylbenzeneacetonitrile | 5-bromo-3-cyano-4-isobutyl-2-isopropyl-6-nitrobenzeneacetonitrile |
| 4-sec-butyl-5-chloro-3-cyano-2-isobutylbenzeneacetonitrile | 4-sec-butyl-5-chloro-3-cyano-2-isobutyl-6-nitrobenzeneacetonitrile |
| 4-chloro-3-cyano-2,6-diethylbenzeneacetonitrile | 4-chloro-3-cyano-2,6-diethyl-5-nitrobenzeneacetonitrile |
| 4-bromo-3-cyano-2,6-diethylbenzeneacetonitrile | 4-bromo-3-cyano-2,6-diethyl-5-nitrobenzeneacetonitrile |
| 4-bromo-3-cyano-2,6-dipropylbenzeneacetonitrile | 4-bromo-3-cyano-5-nitro-2,6-dipropylbenzeneacetonitrile |
| 4-chloro-3-cyano-2,6-dipropylbenzeneacetonitrile | 4-chloro-3-cyano-5-nitro-2,6-dipropylbenzeneacetonitrile |
| 4-chloro-3-cyano-2,6-diisobutylbenzeneacetonitrile | 4-chloro-3-cyano-2,6-diisobutyl-5-nitrobenzeneacetonitrile |
| 4-bromo-3-cyano-2,6-diisobutylbenzeneacetonitrile | 4-bromo-3-cyano-2,6-diisobutyl-5-nitrobenzeneacetonitrile |
| 4-bromo-2,6-di-tert-butyl-3-cyanobenzeneacetonitrile | 4-bromo-2,6-di-tert-butyl-3-cyano-5-nitrobenzeneacetonitrile |
| 4-chloro-3-cyano-2-ethyl-6-propylbenzeneacetonitrile | 4-chloro-3-cyano-2-ethyl-5-nitro-6-propylbenzeneacetonitrile |

TABLE XXXXII-continued

| Starting Material | Product |
|---|---|
| 4-bromo-2-tert-butyl-3-cyano-6-ethylbenzeneacetonitrile | 4-bromo-2-tert-butyl-3-cyano-6-ethyl-5-nitrobenzeneacetonitrile |
| 2-tert-butyl-4-chloro-3-cyano-6-isobutylbenzeneacetonitrile | 2-tert-butyl-4-chloro-3-cyano-6-isobutyl-5-nitrobenzeneacetonitrile |
| 2-tert-butyl-4-chloro-3-cyano-6-propylbenzeneacetonitrile | 2-tert-butyl-4-chloro-3-cyano-5-nitro-6-propylbenzeneacetonitrile |
| 4-bromo-2-tert-butyl-3-cyano-6-propylbenzeneacetonitrile | 4-bromo-2-tert-butyl-3-cyano-5-nitro-6-propylbenzeneacetonitrile |
| 4-bromo-2-tert-butyl-3-cyano-6-isobutylbenzeneacetonitrile | 4-bromo-2-tert-butyl-3-cyano-6-isobutyl-5-nitrobenzeneacetonitrile |
| 4-chloro-3-cyano-2,5-diethylbenzeneacetonitrile | 4-chloro-3-cyano-2,5-diethyl-6-nitrobenzeneacetonitrile |
| 4-bromo-3-cyano-2,5-dipropylbenzeneacetonitrile | 4-bromo-3-cyano-6-nitro-2,5-dipropylbenzeneacetonitrile |
| 4-bromo-3-cyano-2,5-diisobutylbenzeneacetonitrile | 4-bromo-3-cyano-2,5-diisobutyl-6-nitrobenzeneacetonitrile |
| 4-chloro-3-cyano-2,5-diisobutylbenzeneacetonitrile | 4-chloro-3-cyano-2,5-diisobutyl-6-nitrobenzeneacetonitrile |
| 2,5-di-tert-butyl-4-chloro-3-cyanobenzeneacetonitrile | 2,5-di-tert-butyl-4-chloro-3-cyano-6-nitrobenzeneacetonitrile |
| 4-bromo-2,5-di-tert-butyl-3-cyanobenzeneacetonitrile | 4-bromo-2,5-di-tert-butyl-3-cyano-6-nitrobenzeneacetonitrile |
| 4-chloro-3-cyano-2-ethyl-5-isobutylbenzeneacetonitrile | 4-chloro-3-cyano-2-ethyl-5-isobutyl-6-nitrobenzeneacetonitrile |
| 4-bromo-5-tert-butyl-3-cyano-2-isopropylbenzeneacetonitrile | 4-bromo-5-tert-butyl-3-cyano-2-isopropyl-6-nitrobenzeneacetonitrile |
| 4-bromo-5-tert-butyl-3-cyano-2-isobutylbenzeneacetonitrile | 4-bromo-5-tert-butyl-3-cyano-2-isobutyl-6-nitrobenzeneacetonitrile |
| 5-tert-butyl-4-chloro-3-cyano-2-propylbenzeneacetonitrile | 5-tert-butyl-4-chloro-3-cyano-6-nitro-2-propylbenzeneacetonitrile |
| 2-tert-butyl-4-chloro-3-cyano-5-propylbenzeneacetonitrile | 2-tert-butyl-4-chloro-3-cyano-6-nitro-5-propylbenzeneacetonitrile |
| 5-tert-butyl-2-sec-butyl-4-chloro-3-cyanobenzeneacetonitrile | 5-tert-butyl-2-sec-butyl-4-chloro-3-cyano-6-nitrobenzeneacetonitrile |
| 4-bromo-2-sec-butyl-3-cyano-5-isobutylbenzeneacetonitrile | 4-bromo-2-sec-butyl-3-cyano-5-isobutyl-6-nitrobenzeneacetonitrile |
| 4-chloro-3-cyano-2-ethyl-5-tert-pentylbenzeneacetonitrile | 4-chloro-3-cyano-2-ethyl-6-nitro-5-tert-pentylbenzeneacetonitrile |
| 4-chloro-3-cyano-5-(1,2-dimethylpropyl)-2-ethylbenzeneacetonitrile | 4-chloro-3-cyano-5-(1,2-dimethylpropyl)-2-ethyl-6-nitrobenzeneacetonitrile |
| 6-chloro-3-cyano-2,4-diethylbenzeneacetonitrile | 6-chloro-3-cyano-2,4-diethyl-5-nitrobenzeneacetonitrile |
| 6-bromo-3-cyano-2,4-diethylbenzeneacetonitrile | 6-bromo-3-cyano-2,4-diethyl-5-nitrobenzeneacetonitrile |
| 6-bromo-3-cyano-2,4-dipropylbenzeneacetonitrile | 6-bromo-3-cyano-5-nitro-2,4-dipropylbenzeneacetonitrile |
| 6-chloro-3-cyano-2,4-dipropylbenzeneacetonitrile | 6-chloro-3-cyano-5-nitro-2,4-dipropylbenzeneacetonitrile |
| 6-chloro-3-cyano-2,4-diisopropylbenzeneacetonitrile | 6-chloro-3-cyano-2,4-diisopropyl-5-nitrobenzeneacetonitrile |
| 6-bromo-3-cyano-2,4-diisopropylbenzeneacetonitrile | 6-bromo-3-cyano-2,4-diisopropyl-5-nitrobenzeneacetonitrile |
| 6-bromo-3-cyano-2,4-diisobutylbenzeneacetonitrile | 6-bromo-3-cyano-2,4-diisobutyl-5-nitrobenzeneacetonitrile |
| 6-chloro-3-cyano-2,4-diisobutylbenzeneacetonitrile | 6-chloro-3-cyano-2,4-diisobutyl-5-nitrobenzeneacetonitrile |
| 2,4-di-sec-butyl-6-chloro-3-cyanobenzeneacetonitrile | 2,4-di-sec-butyl-6-chloro-3-cyano-5-nitrobenzeneacetonitrile |
| 6-bromo-2,4-di-sec-butyl-3-cyanobenzeneacetonitrile | 6-bromo-2,4-di-sec-butyl-3-cyano-5-nitrobenzeneacetonitrile |
| 6-bromo-2,4-di-tert-butyl-3-cyanobenzeneacetonitrile | 6-bromo-2,4-di-tert-butyl-3-cyano-5-nitrobenzeneacetonitrile |
| 2,4-di-tert-butyl-6-chloro-3-cyanobenzeneacetonitrile | 2,4-di-tert-butyl-6-chloro-3-cyano-5-nitrobenzeneacetonitrile |
| 2-tert-butyl-6-chloro-3-cyano-4-ethylbenzeneacetonitrile | 2-tert-butyl-6-chloro-3-cyano-4-ethyl-5-nitrobenzeneacetonitrile |
| 2-tert-butyl-6-chloro-3-cyano-4-isobutylbenzeneacetonitrile | 2-tert-butyl-6-chloro-3-cyano-4-isobutyl-5-nitrobenzeneacetonitrile |
| 2-tert-butyl-6-chloro-3-cyano-4-ispropylbenzeneacetonitrile | 2-tert-butyl-6-chloro-3-cyano-4-isopropyl-5-nitrobenzeneacetonitrile |
| 4-sec-butyl-2-tert-butyl-6-chloro-3-cyanobenzeneacetonitrile | 4-sec-butyl-2-tert-butyl-6-chloro-3-cyano-5-nitrobenzeneacetonitrile |
| 6-bromo-2-sec-butyl-4-tert-butyl-3-cyanobenzeneacetonitrile | 6-bromo-2-sec-butyl-4-tert-butyl-3-cyano-5-nitrobenzeneacetonitrile |
| 6-bromo-4-tert-butyl-3-cyano-2-isobutylbenzeneacetonitrile | 6-bromo-4-tert-butyl-3-cyano-2-isobutyl-5-nitrobenzeneacetonitrile |
| 6-bromo-2-tert-butyl-3-cyano-4-isobutylbenzeneacetonitrile | 6-bromo-2-tert-butyl-3-cyano-4-isobutyl-5-nitrobenzeneacetonitrile |
| 6-chloro-3-cyano-2-isobutyl-4-isopropylbenzeneacetonitrile | 6-chloro-3-cyano-2-isobutyl-4-isopropyl-5-nitrobenzeneacetonitrile |
| 6-chloro-3-cyano-4-isobutyl-2-isopropylbenzeneacetonitrile | 6-chloro-3-cyano-4-isobutyl-2-isopropyl-5-nitrobenzeneacetonitrile |
| 4-sec-butyl-6-chloro-3-cyano-2-isobutylbenzeneacetonitrile | 4-sec-butyl-6-chloro-3-cyano-2-isobutyl-5-nitrobenzeneacetonitrile |

EXAMPLE 34

3-Bromo-2,4,6-triisopropylbenzyl Chloride

To a solution of 25 parts of 2,4,6-triisopropylbenzyl chloride (Organic Reactions, Vol. I, p. 68) in 150 parts of carbon tetrachloride is added 1 part of iron powder. The mixture is cooled and maintained at 15°–20°C, and then a solution of 16 parts bromine in 15 parts carbon tetrachloride is added dropwise during two hours. The resulting solution is washed with dilute sodium bicarbonate solution and water. It is dried with magnesium sulfate and stripped of solvent in vacuo giving 3-bromo-2,4,6-triisopropylbenzyl chloride, b.p. 111°C. (0.05 mm.)

The following compounds are made by appropriate substitution in the above procedure.

TABLE XXXXIII

| Starting Material | Product |
| --- | --- |
| 2,4,6-tripropylbenzyl chloride | 3-bromo-2,4,6-tripropylbenzyl chloride |
| 4-tert-butyl-2,6-dimethylbenzyl chloride | 3-bromo-4-tert-butyl-2,6-dimethylbenzyl chloride |
| 4-tert-butyl-2,6-diisopropylbenzyl chloride | 3-bromo-tert-butyl-2,6-diisopropylbenzyl chloride |
| 4-isopropyl-2,6-dimethylbenzyl chloride | 3-bromo-4-isopropyl-2,6-dimethylbenzyl chloride |
| 2,6-diisopropyl-4-methylbenzyl chloride | 3-bromo-2,6-diisopropyl-4-methylbenzyl chloride |
| 2,4,6-triisopropylbenzyl chloride | 3-chloro-2,4,6-triisopropylbenzyl chloride |

The procedure of Example 34 is used to prepare the following compounds, but two equivalents of bromine are used per equivalent of substituted benzyl chloride.

TABLE XXXXIV

| Starting Material | Product |
| --- | --- |
| 2,4,6-triisopropylbenzyl chloride | 3,5-dibromo-2,4,6-triisopropylbenzyl chloride |
| 4-tert-butyl-2,6-dimethylbenzyl chloride | 3,5-dibromo-4-tert-butyl-2,6-dimethylbenzyl chloride |
| 4-tert-butyl-2,6-diisopropylbenzyl chloride | 3,5-dibromo-4-tert-butyl-2,6-diisopropylbenzyl chloride |
| 4-isopropyl-2,6-dimethylbenzyl chloride | 3,5-dibromo-4-isopropyl-2,6-dimethylbenzyl chloride |
| 2,6-diisopropyl-4-methylbenzyl chloride | 3,5-dibromo-2,6-diisopropyl-4-methylbenzyl chloride |
| 2,4,6-triisopropylbenzyl chloride | 3,5-dichloro-2,4,6-triisopropylbenzyl chloride |

EXAMPLE 35

3-Cyano-2,4,6-triisopropylbenzeneacetonitrile

In a flask equipped with a mechanical stirrer and reflux condenser is placed 33 parts of 3-bromo-2,4,6-triisopropylbenzyl chloride and 75 parts N-methylpyrrolidinone. Then 20 parts cuprous cyanide is added with good stirring and the flask is rapidly heated to 200°C and kept at 205°–210°C for 30 min. The flask is cooled, and the contents are poured onto ice and water. The mixture is stirred vigorously, filtered and washed with cold water. The thick paste is suspended in water and 200 parts methylene chloride is added. Ten parts of chlorine is slowly passed in under the surface at 15°C; the methylene chloride solution is separated, washed twice with dilute hydrochloric acid, then with 5% sodium bicarbonate solution and with water. The solution is dried, filtered and evaporated to yield 3-cyano-2,4,6-triisopropylbenzeneacetonitrile, m.p. 98°–101 °C.

The following compounds are made by appropriate substitution in the above procedure.

TABLE XXXXV

| Starting Material | Product |
| --- | --- |
| 3-bromo-2,4,6-tripropylbenzyl chloride | 3-cyano-2,4,6-tripropylbenzeneacetonitrile |
| 3-bromo-4-tert-butyl-2,6-dimethylbenzyl chloride | 4-tert-butyl-3-cyano-2,6-dimethylbenzeneacetonitrile |
| 3-bromo-4-tert-butyl-2,6-diisopropylbenzyl chloride | 4-tert-butyl-3-cyano-2,6-diisopropylbenzeneacetonitrile |
| 3-bromo-4-isopropyl-2,6-dimethylbenzyl chloride | 3-cyano-4-isopropyl-2,6-dimethylbenzeneacetonitrile |
| 3-bromo-2,6-diisopropyl-4-methylbenzyl chloride | 3-cyano-2,6-diisopropyl-4-methylbenzeneacetonitrile |
| 3-bromo-2,4,6-triethylbenzyl chloride | 3-cyano-2,4,6-triethylbenzeneacetonitrile |
| 3-chloro-2,4,6-triisopropylbenzyl chloride | 3-cyano-2,4,6-triisopropylbenzeneacetonitile |

The procedure of Example 35 is used to prepare the following compounds, but two equivalents of cuprous cyanaide are used per equivalent of benzyl chloride.

TABLE XXXXVI

| Starting Material | Product |
| --- | --- |
| 3,5-dibromo-2,4,6-triisopropylbenzyl chloride | 3-bromo-5-cyano-2,4,6-triisopropylbenzeneacetonitrile |
| 3,5-dibromo-4-tert-butyl-2,6-dimethylbenzyl chloride | 3-bromo-4-tert-butyl-5-cyano-2,6-dimethylbenzeneacetonitrile |
| 3,5-dibromo-4-tert-butyl-2,6-diisopropylbenzyl chloride | 3-bromo-4-tert-butyl-5-cyano-2,6-diisopropylbenzeneacetonitrile |
| 3,5-dibromo-4-isopropyl-2,6-dimethylbenzyl chloride | 3-bromo-5-cyano-4-isopropyl-2,6-dimethylbenzeneacetonitrile |

TABLE XXXXVI-continued

| Starting Material | Product |
| --- | --- |
| 3,5-dibromo-2,6-diisopropyl-4-methylbenzyl chloride | 3-bromo-5-cyano-2,6-diisopropyl-4-methylbenzeneacetonitrile |
| 3,5-dibromo-2,4,6-triethylbenzyl chloride | 3-bromo-5-cyano-2,4,6-triethylbenzeneacetonitrile |
| 3-bromo-5-chloro-2,4,6-triisopropylbenzyl chloride | 5-chloro-3-cyano-2,4,6-triisopropylbenzeneacetonitrile |

Compositions

The compounds of Formula (1) can be formulated for herbicidal use in conventional ways. The formulations can be wettable powders, dusts, suspensions in water and/or organic solvents, solutions, emulsifiables, high-strength compositions, pellets, or granules. The other herbicides listed above can be tank-mixed with the compounds of Formula (1) in the form of finished formulations or they can be combined to give single formulations for reasons of convenience. The formulations will include inert carrier materials and/or surfactants which serve as wetting, emulsifying and/or dispersing agents. Anionic or nonionic surfactants are preferred; lists of suitable surfactants can be found in "Detergents and Emulsifiers Annual" (1971) by John W. McCutcheon, Inc. The formulations will contain about 2 to 99% by weight, of active compound or compounds, up to about 20% by weight of a surfactant, and/or up to about 98% by weight of inert solid or liquid carrier. For dusts, 2 to 25% of active compound can be used, for granules or pellets 5–50%, for solutions or suspensions 10–50%, for wettable powders 20–90%, and highstrength compositions 90–99%. In some instances the surfactant can be used at up to 5 times the amount of active ingredient to improve the effectiveness of the active compound. This amount of surfactant is most conveniently applied as a tank-mix with the active component.

Organic liquids suitable for preparation of solutions, suspensions, and emulsifiable concentrates containing the compounds of Formula (1) include alcohols, glycols, mono- and dialkyl ethers of ethylene glycol and diethylene glycol, ketones, esters, sulfamides, amides, paraffinic hydrocarbons, aromatic hydrocarbons, and halogenated hydrocarbons. Liquids containing hydroxy or amino groups may react in storage with halomethyl aromatic compounds, so for best stability this combination should be avoided. At normal levels surfactants containing a small proportion of hydroxyl groups (e.g., polyethylene glycol ethers) react surprisingly little. Choice of a liquid is dictated by the reactivity, the solubility of the active compound to be used and whether a suspension or solution is desired. In general, compounds of Formula (1) are insufficiently soluble in water to permit aqueous solution formulations.

Solid, inert carrier materials suitable for wettable powders, pellets and granules include natural clays, synthetic fine silicas, and other materials commonly used for this purpose.

Further information concerning the preparation of herbicidal formulations can be found in U.S. Pat. No. 3,235,357 and in the following sections A through D.

A. WETTABLE POWDERS

Wettable powders are water-dispersible compositions containing the active material, an inert solid extender, and one or more surfactants to provide rapid wetting and prevent heavy flocculation when suspended in water.

The inert extenders which are preferred for use in the wettable powders of this invention containing the active compounds are of mineral origin.

The classes of extenders suitable for the wettable powder formulations of this invention are the natural clays, diatomaceous earth, and synthetic mineral fillers derived from silica and silicate. Most preferred fillers for this invention are kaolinites, attapulgite clay, montmorillonite clays, synthetic silicas, synthetic magnesium silicate and calcium sulfate dihydrate.

Suitable surfactants for use in such compositions are those listed by J. W. McCutcheon in "Detergents and Emulsifiers" 1971 Annual. Among the more preferred surfactants are the non-ionic and anionic type, and those most suitable for the preparation of the dry, wettable products of this invention are solid forms of compounds known to the art as wetters and dispersants. Occasionally a liquid, non-ionic compound classified primarily as an emulsifier may serve as both wetter and dispersant.

Most preferred wetting agents are alkylbenzene and alkylnaphthalene sulfonates, sulfated fatty alcohols, amines or acid amides, long-chain acid esters of sodium isethionate, esters of sodium sulfosuccinate, sulfated or sulfonated fatty acid esters, petroleum sulfonates, sulfonated vegetable oils, and ditertiary acetylenic glycols. Preferred dispersants are methyl cellulose, polyvinyl alcohol, lignin sulfonates, polymeric alkylnaphthalene sulfonates, sodium naphthalenesulfonate, polymethylene bisnaphthalenesulfonate, and sodium N-methyl-N-(long-chain acid) taurates.

Wetting and dispersing agents in these preferred wettable powder compositions of this invention are usually present at concentrations of from about 0.25 weight percent to 5 weight percent. The inert extender then completes the formulation. Where needed, 0.1 weight percent to 1.0 weight percent of the extender may be replaced by a corrosion inhibitor or an antifoaming agent or both.

Thus, wettable powder formulations of the invention will contain from about 20 to 90 weight percent active material, from 0.5 to 3.0 weight percent wetting agent, from 0.25 to 5.0 weight percent dispersant, and from 9.25 to 79.25 weight percent inert extender, as these terms are described above.

Wettable powders can conveniently be produced by blending the ingredients in conventional blenders, followed by grinding the mixture one or more times in a hammer mill, pin mill, fluid energy mill or the like. Particle size classifiers may be used to remove over-size material for further grinding. It is usually desirable to reblend after milling and to sift out flakes and debris before packaging.

B. HIGH-STRENGTH COMPOSITIONS AND AQUEOUS AND OIL SUSPENSION CONCENTRATES

High-strength compositions generally consist of 90 to 99% active ingredient and 1.0 to 10% of a solid inert absorptive diluent of a liquid or solid surfactant such as those described by McCutcheon in "Detergents and Emulsifiers" 1971 Annual. Such high-strength compositions can often be used in a manner similar to the wettable powders but they are also suitable for further formulation.

The aqueous suspension concentrates are prepared by mixing together and sandgrinding an aqueous slurry of water-insoluble active ingredient in the presence of dispersing agents. Thus there is obtained a concentrated slurry of very finely divided particles in which the active ingredient is substantially all below 10 microns in size. This concentrated aqueous suspension is characterized by its extremely small particle size so that upon diluting and spraying, a very uniform coverage is obtained.

These aqueous suspension concentrates will contain from 10 to 50% of active ingredient, from 45 to 70% water with the remainder made up of surfactants, corrosion inhibitors, and suspending agents.

Suspensions in organic liquids can be prepared in a similar manner such as by replacing the water with mineral oil.

C. SOLUTIONS AND EMULSIFIABLE OILS

Emulsifiable oils are usually solutions of active material in non-water miscible solvents together with a surfactant. Omission of the surfactant gives a solution which can be applied by low volume techniques or diluted with weed oils.

For the compounds of this invention, emulsifiable oils can be made by mixing the active ingredient with a solvent and surfactant. Suitable solvents for the compounds of this invention are aromatic hydrocarbons including many weed oils, chlorinated solvents, and non-water miscible ethers, esters, or ketones. Suitable surfactants are those anionic or non-ionic agents known to the art as emulsifying agents. Such compounds can be found listed in "Detergents and Emulsifiers" 1971 Annual by John W. McCutcheon, Inc.

Emulsifying agents most suitable for the emulsifiable oil compositions of this invention are long-chain alkyl or mercaptan polyethoxy alcohols, alkylaryl polyethoxy alcohols, sorbitan fatty acid esters, polyoxyethylene ethers with sorbitan fatty acid esters, polyethylene glycol esters with fatty or rosin acids, fatty alkylol amide condensates, calcium and amine salts of fatty alcohol sulfates, oil soluble petroleum sulfonates or, preferably, mixtures of these emulsifying agents. Such emulsifying agents will comprise from about 1 to 10 weight percent of the total composition. As described above, however, up to 5 parts of emulsifying agent for each part of active compound can be used.

Thus, emulsifiable oil compositions of the present invention will consist of from about 10 to 50 weight percent active material, about 40 to 89 weight percent solvent, and about 1 to 10 weight percent emulsifier, as these terms are defined and used above.

In some instances the oil solution may be intended merely for extension with other oils, such as weed oils or for low volume application. In this instance the emulsifying agents may be omitted and may be replaced by additional solvent.

D. GRANULES AND PELLETS

Granules and pellets are physically stable, particulate compositions containing the active compounds which adhere to or are distributed through a basic matrix of a coherent, inert carrier with macroscopic dimensions. In order to aid leaching of te active ingredient from the granule or pellet, a surfactant can be present.

For the compounds of this invention, the inert carrier is preferably of mineral origin, and the surfactant is a compound known to the art as a wetting agent. Such compounds are listed by J. W. McCutcheon in "Detergents and Emulsifiers" 1971 Annual.

Suitable carriers are natural clays, some pyrophyllites and vermiculite. Suitable wetting agents are anionic or non-ionic.

For the granule compositions of this invention, most suitable carriers are of two types. The first are porous, absorptive, preformed granules, such as preformed and screened granular attapulgite or heat expanded, granular, screened vermiculite. On either of these, a solution of the active agent can be sprayed and will be absorbed at concentrations up to 25 weight percent of the total weight. The second, which are also suitable for pellets, are initially powdered kaolin clays, hydrated attapulgite, or bentonite clays in the form of sodium, calcium or magnesium bentonites. Water-soluble salts, such as sodium salts, may also be present to aid in the disintegration of granules or pellets in the presence of moisture. These ingredients are blended with the active components to give mixtures that are granulated or pelleted, followed by drying, to yield formulations with the active component distributed uniformly throughout the mass. Such granules and pellets can also be made with up to 50 weight percent active component, but more frequently a concentration of about 10 weight percent is desired for optimum distribution. The granular compositions of this invention are most useful in a size range of 15–80 mesh (1.3–0.18 mm).

The best surfactants for the granular compositions of this invention depend upon the type of granule used. When preformed granules are sprayed with active material in liquid form the most suitable surfactants are non-ionic, liquid wetters miscible with the solvent. These are compounds more generally known to the art as emulsifiers, and comprise alkylaryl polyether alcohols, alkyl polyether alcohols, polyoxyethylene sorbitan fatty acid esters, polyethylene glycol esters with fatty or rosin acids, fatty alkylol amide condensates, oil soluble petroleum or vegetable oil sulfonates, or mixtures of these. Such agents will usually comprise up to about 5 weight percent of the total composition.

When the active ingredient is first mixed with a powdered carrier and subsequently granulated, or pelleted, liquid non-ionic wetters can still be used, but it is usually preferable to incorporate at the mixing stage one of the solid, powdered anionic wetting or dispersing agents such as those previously listed for the wettable powders. Such agents will comprise from about 0 to 2 weight percent of the total composition.

Thus, the preferred granular or pelleted formulations of this invention comprise about 5 to 30 weight percent active material, about 0 to 5 weight percent surfactant, and about 65 to 95 weight percent inert mineral carrier, as these terms are used herein.

Some preferred herbicidal compositions and methods of this invention are illustrated by the following examples, wherein all parts, proportions, and percentages are by weight unless indicated otherwise.

EXAMPLE A

| | |
|---|---|
| 4-cyano-2,5-diisopropylbenzeneacetonitrile | 51% |
| sodium N-methyl N-oleoyl taurate | 3% |
| sodium lignin sulfonate | 2% |
| synthetic silica | 44% |

The above ingredients are blended, hammer-milled to pass an 0.25 mm screen, air-milled in a fluid-energy mill, and reblended.

Two kilograms of the above formulation and one-half kilogram of 80% wettable linuron are suspended in 200 liters of water and applied preemergence to a hectare of soybeans planted in Butlertown silt loam soil. Compared with the results obtained on a control plot on which no herbicide is used, this treatment controls all weeds present without injury to the crop and it produces an excellent yield.

EXAMPLE B

| | |
|---|---|
| 2-sec-butyl-5-cyano-4-neopentyl-benzeneacetonitrile | 25% |
| diatomaceous earth | 63% |
| methylated cellulose | 1% |
| dioctyl sodium sulfosuccinate | 1% |
| synthetic silica | 10% |

The above ingredients are blended, hammer-milled to pass an 0.25 mm screen and reblended.

4-tert-Butyl-3-cyanobenzeneacetonitrile can be formulated in like manner.

Eight kilograms of this formulation plus 1.25 kilograms of atrazine formulated as an 80% wettable powder are suspended in 250 liters of water and applied pre-emergence to a hectare of corn planted in Flanagan silt loam soil. The treatment gives excellent control of a wide spectrum of both broadleaves and grasses without injury to the corn. The corn produces an excellent yield.

EXAMPLE C

| | |
|---|---|
| 4-cyano-5-isopropyl-2-nitrobenzene-acetonitrile | 25% |
| xylene | 65% |
| blend of nonylphenoxy polyethylene glycol ethers and alkylaryl-sulfonates | 10% |

The above ingredients are agitated in a blender with warming until a homogeneous solution results.

4-Cyano-2,5-diisopropylbenzeneacetonitrile can be formulated in like manner.

Sixteen kilograms of the above formulation are emulsified in 200 liters of water and applied preemergence to a hectare of corn planted in Norfolk sandy loam soil. The treatment controls a number of weeds, particularly weedy grasses, and the corn grown without competition produces an excellent yield.

EXAMPLE D

| | |
|---|---|
| 5-tert-butyl-4-cyano-2-ethylbenzene-acetonitrile | 33% |
| isophorone | 27% |
| aromatic naphtha | 30% |
| polyethylene glycol laurate | 5% |

EXAMPLE D-continued

| | |
|---|---|
| oil soluble calcium alkylarylsulfonate | 5% |

The above ingredients are homogenized by stirring in a blender.

4-Bromo-5-tert-butyl-2-ethylbenzyl chloride can be formulated in like manner.

Nine kilograms of the above formulation are suspended in 50 liters of water and applied preemergence by aircraft to a hectare of wheat. Several weedy grasses are controlled, allowing the wheat to grow and produce an excellent yield without weed competition.

EXAMPLE E

| | |
|---|---|
| 4-Cyano-2,5-diisopropylbenzene-acetonitrile | 20% |
| trimethylnonyl polyethylene glycol ether | 40% |
| xylene | 20% |
| isophorone | 20% |

The above ingredients are warmed in a blender with stirring until a homogeneous solution results.

Ten kilograms of the above formulation are suspended in 400 liters of water and applied pre-emergence (behind the planter) to corn planted in Webster silt loam soil. The treatment controls many grassy weeds while the crop grows unhindered and produces an excellent yield.

EXAMPLE F

| | |
|---|---|
| 4-Cyano-2,5-diisopropylbenzene-acetonitrile | 5% |
| attapulgite granules (15–30 mesh 0.53 – app. 1.25 mm) | 90% |
| dimethylformamide | 5% |

A 50% solution of the active ingredient in dimethyl formamide is prepared by warming the two materials with stirring. This solution is then sprayed on the granules which are tumbled in a blender. The granules so prepared are suitable for application without removal of solvent.

4-Bromo-2,5-diisopropylbenzyl chloride and 4-tert-butyl-3-cyanobenzeneacetonitrile can be formulated in like manner.

Fifty kilograms of these granules are distributed pre-emergence over a hectare of cotton planted in silt loam soil. One kilogram of diuron 80% wettable powder is applied as a spray in water at the same time the granules are distributed. This treatment controls a wide variety of weeds without injury to the cotton, which grows and produces an excellent yield of high-quality lint.

EXAMPLE G

| | |
|---|---|
| 4-cyano-5-isopropyl-2-nitrobenzene-acetonitrile | 10.0% |
| 3-(3,4-dichlorophenyl)-1-methoxy-1-methylurea | 2.5% |
| calcium lignin sulfonate plus wood sugars | 15.0% |
| kaolinite clay | 61.5% |
| sodium sulfate | 10.0% |
| sodium lauryl sulfate | 1.0% |

The above ingredients are ground to pass a 0.3 mm screen, blended, moistened with water, extruded and cut into pellets. After drying, these pellets can be applied directly or they can be further subdivided into 30–60 mesh (0.25–0.59 mm) granules for more uniform application. All compounds of this invention can be formulated in like manner.

Forty kilograms of the above granules are distributed behind the planter to a hectare of soybeans being planted in silt loam soil containing 3% organic matter. The treatment controls all weeds present, both broadleaves and grasses, without damage to the crop, which grows without weed competition and produces an excellent yield.

EXAMPLE H

| | |
|---|---|
| 3-bromo-5-tert-butyl-2-ethylbenzyl chloride | 16.5% |
| 4-bromo-6-tert-butyl-3-ethylbenzyl chloride | 16.5% |
| isophorone | 27.0% |
| aromatic naphtha | 30.0% |
| polyethylene glycol laurate | 5.0% |
| oil-soluble calcium alkylaryl-sulfonate | 5.0% |

The above ingredients are homogenized by stirring in a blender.

Twenty-five kilograms of the above formulation are suspended in 200 liters of water and applied pre-emergence to a hectare of corn. Several weedy grasses are controlled, allowing the corn to grow and produce an excellent yield without weed competition.

EXAMPLE I

| | |
|---|---|
| 4-cyano-2,5-diisopropylbenzene-acetonitrile | 98% |
| trimethylnonyl polyethylene glycol ether | 2% |

The above ingredients are blended, hammer-milled to pass an 0.25 mm screen and reblended. This composition can be used directly or as a source of active for other formulations.

Three kilograms of the above formulation and one kilogram of fluometuron are tank-mixed in 400 liters of water and sprayed preemergence on a hectare of cotton planted in Commerce silt loam soil. The cotton emerges to a good stand and grows vigorously without competition from crabgrass (Digitaria spp.), srangletop (Leptochloa spp.), barnyardgrass (*Echinochloa crusgalli* (L.) Beauv.), pigweed (Amaranthus spp.), seedling Johnsongrass (*Sorghum halepense* (L.) Pers.), goosegrass (*Eleusine indica* (L.) Gaertn.), ragweed (*Ambrosia artemisiifolia* L.), spotted spurge (*Euphorbia maculata* L.) or other weeds controlled by the treatment. To obtain similar results, tank mixes are made of the above formulation with one of several other herbicides including diuron at 0.8 kilogram, monuron at 1 kilogram, prometryne at 2 kilograms, norea at 2 kilograms and chloropropham at 4 kilograms per hectare.

EXAMPLE J

| | |
|---|---|
| 4-tert-butyl-3-cyanobenzene-acetonitrile | 35% |
| octylphenyl polyethylene glycol ether | 2% |
| dimethylformamide | 63% |

The above ingredients are stirred together to produce a solution suitable for low-volume application.

The above formulation without dilution is applied by airplane to recently planted spring wheat at the rate of 15 liters per hectare to control downy bromegrass (*Bromus tectorum* L.) and other annual grasses which reduce wheat yields if allowed to compete with the wheat.

EXAMPLE K

| Aqueous Suspension | |
|---|---|
| 4-tert-butyl-4-cyano-2-ethylbenzene-acetonitrile | 15.0% |
| 5-tert-butyl-3-cyano-2-ethylbenzene-acetonitrile | 15.0% |
| hydrated attapulgite | 2.0% |
| calcium lignin sulfonate | 15.0% |
| sodium carbonate | 2.0% |
| sodium pentachlorophenate | 0.7% |
| water | 50.3% |

All the above ingredients except the water are blended and ground to pass a 20-mesh screen. The water is then added, and the mixture is sandground until the solid particles are smaller than 10 microns.

Twenty kilograms of the above formulation are mixed in 450 liters of water with mechanical agitation and sprayed preemergence on a hectare of soybeans planted in Gallion fine sandy loam. The soybeans emerge to a good stand and grow vigorously to maturity unencumbered by weeds such as barnyardgrass, pigweed, foxtail (Sectaria spp.), crabgrass and fall panicum (*Panicum dichotomiflorum* Michx.) which are controlled by the treatment.

EXAMPLE L

| Mixtures | |
|---|---|
| 4-tert-butyl-3-cyanobenzene-acetonitrile | 30% |
| S-ethyl hexahydro-1-H-azepine-1-carbothioate (molinate) | 15% |
| chlorobenzene | 50% |
| blend of oil-soluble calcium alkyl-arylsulfonates with alkyl aryl polyethylene glycol ethers | 5% |

The above ingredients are stirred with warming in a blender until a homogeneous, emulsifiable solution is formed.

Twenty liters of the above emulsifiable formulation are mixed with 350 liters of water and sprayed on a hectare of Perry clay soil. The treatment is incorporated into the surface two or three inches by double disking the area before drilling rice seeds and several days before flooding. The rice grows well and produces a good yield without competition from weeds such as sprangletop (Leptochloa spp.), barnyardgrass, junglerice (*Echinochloa colonum* (L.) Link), ducksalad (*Heteranthera limosa* (Sw.) Willd.), dayflower (*Commelina communis* L.) and broadleaf signalgrass (*Brachiaria platyphylla* (Griseb.) Nash) which are controlled by the herbicide treatment.

EXAMPLE M

| | |
|---|---|
| 5-sec-butyl-4-cyano-α,α-dimethyl-2-nitrobenzeneacetonitrile | 10% |
| "Ordram" 63 (molinate)* | 6% |
| attapulgite granules (24–48 mesh) | 73% |
| dimethylformamide | 11% |

*S-ethyl hexahydro-1-H-azepine-1-carbothioate

The active ingredients are dissolved in the dimethylformamide with warming, and the solution is sprayed on the granules which are tumbled in a mixer. The granules are then screened to remove fines and packaged.

Fifty kilograms of the above granules are spread uniformly by helicopter on a hectare of flooded, water-seeded rice after the rice and weeds have started to grow but before the weeds are more than 4 inches tall. Good control of barnyardgrass, junglerice and ducksalad is obtained. The rice matures and produces good grain yields.

EXAMPLE N

| | |
|---|---|
| 2,4-di-sec-butyl-5-cyano-3-nitro-benzeneacetonitrile | 60% |
| 3-(p-cumenyl)-1,1-dimethylurea | 15% |
| sodium alkylnaphthalenesulfonate | 2% |
| sodium N-methyl-N-oleyl taurate | 3% |
| diatomaceous earth | 20% |

The above ingredients are blended and hammer milled to a particle size essentially below 50 microns and reblended.

Eight kilograms of the above wettable powder are dispersed with mechanical agitation in 400 liters of water and sprayed preemergence on a hectare of dry-seeded rice planted in Crowley silt loam soil. Pigweed, junglerice, and hemp sesbania (*Sesbania exaltata* (Raf.) Cory) are controlled while the rice grows vigorously to maturity giving an excellent yield of grain.

EXAMPLE O

| | |
|---|---|
| 4-cyano-2,5-diisopropylbenzene-acetonitrile | 50% |
| 4-chloro-4-ethylamino-6-isopropylamino-s-triazine (Atrazine) | 25% |
| attapulgite clay | 22% |
| sodium lignin sulfonate | 2% |
| dioctyl sodium sulfosuccinate | 1% |

The above ingredients are blended, hammer-milled to a particle size essentially below 50 microns and reblended.

Four kilograms of the above formulation are dispersed in 450 liters of water and sprayed uniformly on a hectare of hybrid field corn before the weeds and corn have emerged. The sprayed area remains free of weeds including crabgrass, goosegrass, seedling Johnsongrass, foxtail, pigweed and ragweed. The corn grows vigorously and produces a high yield of grain.

EXAMPLE P

| | |
|---|---|
| 4-cyano-2,5-diisopropylbenzene-acetonitrile | 30% |
| 3-(3,4-dichlorophenyl)-1-methoxy-1-methylurea (linuron) | 30% |
| sodium alkylnaphthalenesulfonate | 2% |
| sodium N-methyl-N-oleyl taurate | 3% |
| finely divided synthetic silica | 2% |
| diatomaceous earth | 33% |

The above ingredients are blended, hammer-milled to pass a 50 mesh screen and reblended.

Carrots planted in Sassafras sandy loam soil are treated preemergence with the above formulation at four kilograms per hectare to control such weeds as crabgrass, goosegrass, spotted spurge, pigweed, ragweed, lambsquarters (*Chenopodium album* L.) and foxtail. An excellent yield of high quality carrots results.

EXAMPLE Q

| | |
|---|---|
| 10% granular formulation of "Amiben"* | 33% |
| 5% granular formulation of Example F | 67% |

*3-amino-2,5-dichlorobenzoic acid

The above granules are tumbled in a mixer and packaged.

A field planted to squash, pumpkins and lima beans is treated preemergence with the above granular mixture to control such troublesome weeds as crabgrass, foxtail, fall panicum, barnyardgrass, pigweed and ragweed. The granules are applied uniformly over the area at the rate of 100 kilograms per hectare. The crops produce good yields without competition with the weeds controlled.

EXAMPLE R

| | |
|---|---|
| formulation of Example E | 75% |
| 2,4-D, butyl ester, emulsifiable formulation | 25% |

The above ingredients are blended to form a homogeneous, emulsifiable concentrate.

Twenty-five liters of the above emulsifiable concentrate are dispersed in 400 liters of water and sprayed in early spring on a hectare of Kentucky bluegrass (*Poa pratensis* L.) turf to control crabgrass, foxtail, dandelions (*Taraxacum officinale* Weber) and plantain (Plantago spp.). An attractive bluegrass lawn results.

EXAMPLE S

| | |
|---|---|
| formulation of Example E | 70% |
| "Stam" F-34* | 30% |

*Commercial formulation combining 3 lbs/gal of 3,4-dichloropropionanilide

The above formulations are blended to yield an emulsifiable concentrate.

Rice is drill-planted in Crowley silt loam soil. With rice and weeds in the early postemergence stage, thirty liters of the above formulation are mixed in 300 liters of water and sprayed uniformly on a hectare of rice. Four days later the rice is flooded to a depth of about 4 inches. The rice grows vigorously to maturity without competition from barnyardgrass (*Echinochloa crusgalli* (L.) Beauv.), signalgrass (Brachiaria spp.), sprangletop (Leptochloa spp.), ducksalad (*Heteranthera limosa*) and dayflower (*Commelina communis* L.) which are controlled.

EXAMPLE T

| | |
|---|---|
| 4-cyano-2,5-diisopropylbenzene-acetonitrile | 25% |
| 3(3,4-dichlorophenyl)-1,1-di-methylurea (diuron) | 25% |
| sodium N-methyl N-oleoyl taurate | 3% |
| sodium alkylnaphthalenesulfonate | 2% |
| diatomaceous earth | 45% |

The above ingredients are blended, hammer-milled to a particle size essentially below 50 microns and reblended.

Ten kilograms of the above formulation are dispersed with continuous bypass agitation in 400 liters of water and sprayed on a hectare of established Kentucky bluegrass in Western Oregon to control weedy annual grasses and broadleaf weeds.

EXAMPLE U

| | |
|---|---|
| 4-tert-butyl-3-cyanobenzene-acetonitrile | 15% |
| 3(3,4-dichlorophenyl)-1,1-di-methylurea (diuron) | 15% |
| paraffinic hydrocarbon oil | 61% |
| polyoxyethylene sorbitol heptaoleate | 8% |
| synthetic fine silica | 1% |

The ingredients are combined and sand-milled to produce particles essentially all below 5 microns. For application, the product can be extended with either oils or water. An emulsion is formed in the latter.

Fifty liters of the above formulation are added to a 2000 liter spray tank filled with water and provided with continuous bypass agitation. The emulsion is sprayed on a 30 millimeter band behind the press wheel of a cotton planter at a volume rate of 400 liters per treated hectare. Good control of crabgrass, pigweed, ragweed, seedling Johnsongrass, goosegrass, barnyardgrass and signalgrass is obtained. The cotton grows to maturity producing a good yield of seed cotton.

In the following composition claims, the term "consisting essentially of" means that in addition to the recited components the composition also may contain other components which do not adversely affect its effectiveness for the intended use.

I claim:

1. A compound having the formula

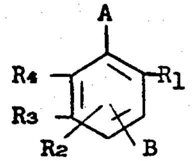

, wherein

A and B are different, one being a Z group and the other being a $CR_5R_6Z$ radical; wherein $R_5$ and $R_6$ are each independently hydrogen or methyl, and Z is the cyano group; and each of $R_1$, $R_2$, $R_3$, and $R_4$ independently is hydrogen, a $C_1$–$C_7$ alkyl, a halogen, or the nitro group;

provided that:

a. at most two of $R_1$, $R_2$, $R_3$, and $R_4$ are nitro groups;

b. at most two of $R_1$, $R_2$, $R_3$, and $R_4$ are halogens;

c. at least one of $R_1$, $R_2$, $R_3$, and $R_4$ is hydrogen or halogen;

d. at least one of $R_1$, $R_2$, $R_3$, and $R_4$ is a $C_2$–$C_7$ alkyl;

e. no nitro groups are ortho to each other;

f. no alkyl groups are ortho to each other;

g. each alkyl group has at most three carbon atoms in a straight chain from the point of attachment to the aromatic ring.

2. A compound of claim 1 wherein each of $R_2$, $R_4$, $R_5$, and $R_6$ is hydrogen; $R_1$ and $R_3$ are each independently a $C_2$-$C_5$ alkyl, chlorine, bromine, or the nitro group.

3. A compound of claim 2 wherein $R_1$ is a $C_3$-$C_5$ alkyl or the nitro group, and $R_3$ is a $C_3$-$C_5$alkyl.

4. 4-Cyano-2,5-diisopropylbenzeneacetonitrile, the compound of claim 3 wherein each of $R_1$ and $R_3$ is an isopropyl group.

* * * * *